US012658325B2

(12) United States Patent
Bollella et al.

(10) Patent No.:     US 12,658,325 B2
(45) Date of Patent:     Jun. 16, 2026

(54) DIAGNOSTIC PATCHES AND BRACELETS FOR PROMOTING PERSONAL AND COMMUNITY HEALTH INCLUDING RELATED PROCESSES, METHODS, AND SYSTEMS

(71) Applicant: LIFE PATCH INTERNATIONAL, Irvine, CA (US)

(72) Inventors: Donald Bollella, Irvine, CA (US); Ramoncito M. Valencia, Irvine, CA (US); Romilda Olszewski Bollella, Irvine, CA (US)

( * ) Notice: Subject to any disclaimer, the term of this patent is extended or adjusted under 35 U.S.C. 154(b) by 208 days.

(21) Appl. No.: 17/885,306

(22) Filed: Aug. 10, 2022

(65) Prior Publication Data

US 2023/0178252 A1     Jun. 8, 2023

Related U.S. Application Data

(63) Continuation of application No. PCT/US2021/017679, filed on Feb. 11, 2021.

(Continued)

(51) Int. Cl.
*G16H 50/70*     (2018.01)
*A61B 5/00*     (2006.01)
(Continued)

(52) U.S. Cl.
CPC ........... *G16H 50/70* (2018.01); *A61B 5/0008* (2013.01); *A61B 5/01* (2013.01); *A61B 5/681* (2013.01);
(Continued)

(58) Field of Classification Search
CPC ...... G16H 50/70; G16H 10/60; A61B 5/0008; A61B 5/01; A61B 5/681; A61B 5/6833;
(Continued)

(56) References Cited

U.S. PATENT DOCUMENTS 9,968,296 B2 *   5/2018   Lee ......................... A61B 5/165
10,265,017 B1 *   4/2019   Myslinski ................ A61B 5/07
(Continued)

FOREIGN PATENT DOCUMENTS

CN     109636694 A     4/2019
CN     111765988 A     10/2020
(Continued)

OTHER PUBLICATIONS

International Search Report dated Aug. 3, 2021 for PCT/US2021/017679.
Written Opinion dated Aug. 3, 2021 for PCT/US2021/017679.

*Primary Examiner* — Daryl C Pope
(74) *Attorney, Agent, or Firm* — Chang & Hale LLP

(57)     ABSTRACT

Diagnostic patches and bracelets for promoting personal and community health including related processes, methods, and systems are directed to fever patches and fever bracelets for school and university health and wellness including mitigation of the spread of infectious diseases and contact tracing during an epidemic or pandemic. Other populations addressed by these methods include nursing homes, office buildings, and factories as well as the general citizenry of entire cities, counties, states, and even countries at large. Further apparatus and devices include disease detection patches and disease detection bracelets for identifying the onset of an infection and for detecting the present of antibodies to such infectious diseases. Related mitigation and contact methods for several different addressed groups and large populations are also provided for these disease detection patches and bracelets.

6 Claims, 59 Drawing Sheets

Related U.S. Application Data

(60) Provisional application No. 63/050,029, filed on Jul. 9, 2020, provisional application No. 63/042,677, filed on Jun. 23, 2020, provisional application No. 63/029,622, filed on May 25, 2020, provisional application No. 63/023,512, filed on May 12, 2020, provisional application No. 63/019,295, filed on May 2, 2020, provisional application No. 62/977,691, filed on Feb. 17, 2020, provisional application No. 62/976,295, filed on Feb. 13, 2020, provisional application No. 62/972,654, filed on Feb. 11, 2020, provisional application No. 62/972,657, filed on Feb. 11, 2020.

(51) Int. Cl.
  *A61B 5/01* (2006.01)
  *G16H 10/60* (2018.01)

(52) U.S. Cl.
  CPC ............ *A61B 5/6833* (2013.01); *A61B 5/746* (2013.01); *G16H 10/60* (2018.01)

(58) Field of Classification Search
  CPC ....... A61B 5/746; A61B 5/024; A61B 5/0816; Y02A 90/10; G06Q 50/265; G06Q 50/22; G06Q 50/26; G06K 19/0717; G06K 19/07762
  See application file for complete search history.

(56) References Cited

U.S. PATENT DOCUMENTS

| | | |
|---|---|---|
| 2016/0302733 A1 | 10/2016 | Lee |
| 2017/0270262 A1 | 9/2017 | Noh et al. |

FOREIGN PATENT DOCUMENTS

| | | |
|---|---|---|
| KR | 10-2012-0065540 A | 6/2012 |
| KR | 10-2016-0040670 A | 4/2016 |
| WO | 2019-140224 A2 | 7/2019 |

* cited by examiner

STUDENT PATCH OR BRACELET WIRELESSLY CONNECTABLE TO PARENTS PHONE VIA, WIFI AND SCHOOL INTERNET

100

106

106

106

106

106

106

106

SCHOOL

HEALTH AND WELLNESS STATION

102

CDC

STATE HEALTH

LOCAL HEALTH

SCHOOL MEDICAL SERVER

104

126

NON-INVASIVE FEVER PATCH

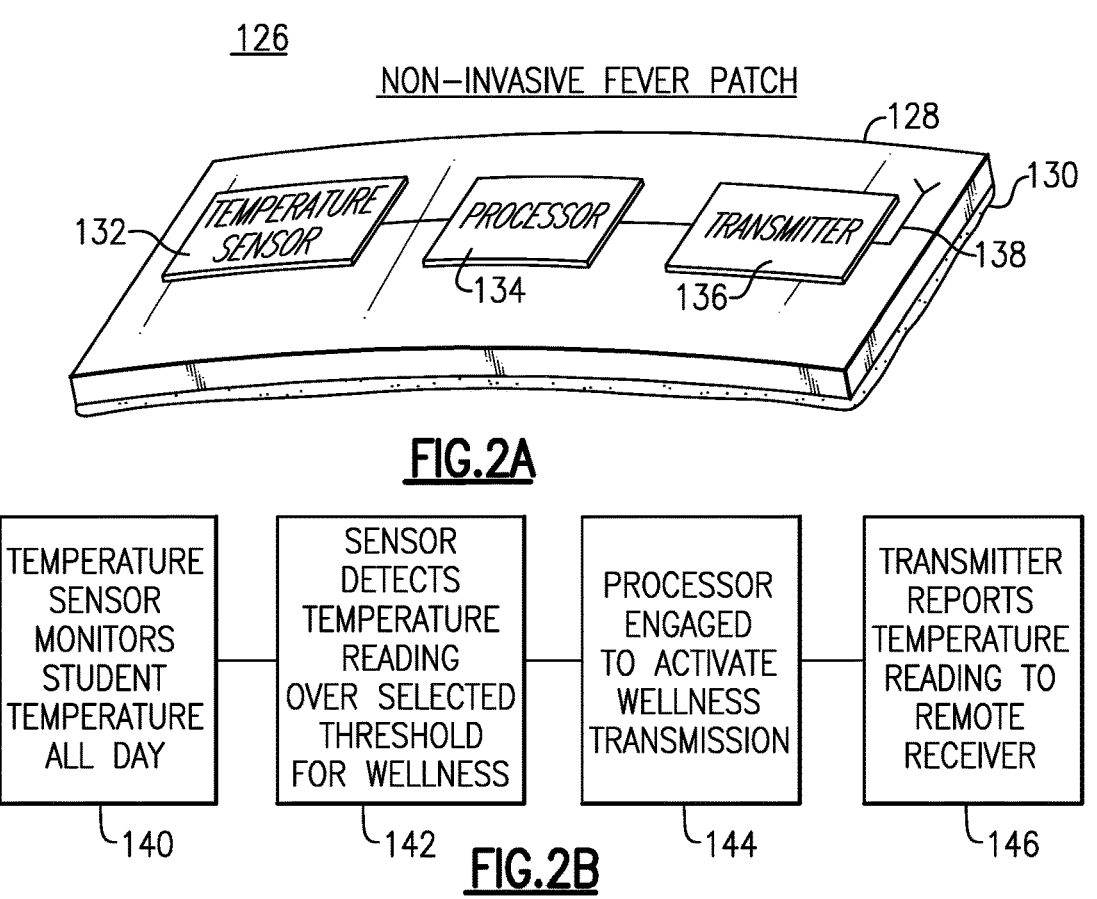

FIG.2A

| TEMPERATURE SENSOR MONITORS STUDENT TEMPERATURE ALL DAY | SENSOR DETECTS TEMPERATURE READING OVER SELECTED THRESHOLD FOR WELLNESS | PROCESSOR ENGAGED TO ACTIVATE WELLNESS TRANSMISSION | TRANSMITTER REPORTS TEMPERATURE READING TO REMOTE RECEIVER |
|---|---|---|---|
| 140 | 142 | 144 | 146 |

FIG.2B

PATCH CONFIGURATIONS TO PROMOTE
SOCIAL ACCEPTANCE AND COMMUNITY SERVICE

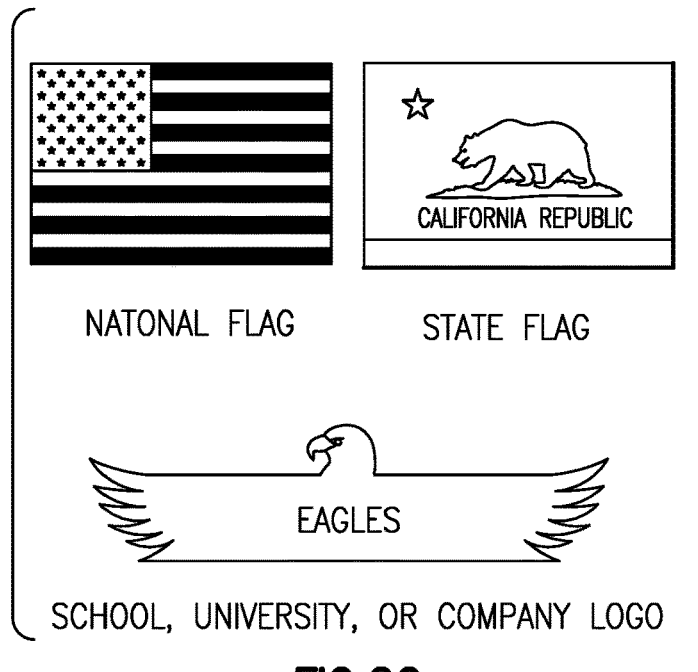

NATONAL FLAG          STATE FLAG

EAGLES

SCHOOL, UNIVERSITY, OR COMPANY LOGO

FIG.2C

NON—INVASIVE DISEASE DETECTION

170

174

170

148a

172

148b

174

176

STUDENT SNEEZES OR COUGHS ON TO SURFACE PAD

178

ASSAY PROCESSING CARTRIDGE CONDUCTS TEST FOR PATHOGENS ON DROPLETS

180

RESULTS POSITIVE OR NEGATIVE ARE DETERMINED FOR SPECIFIC TEST

182

TRANSMITTER REPORTS ASSAY RESULTS TO REMOTE RECEIVER

COUGH OR SNEEZE PAD
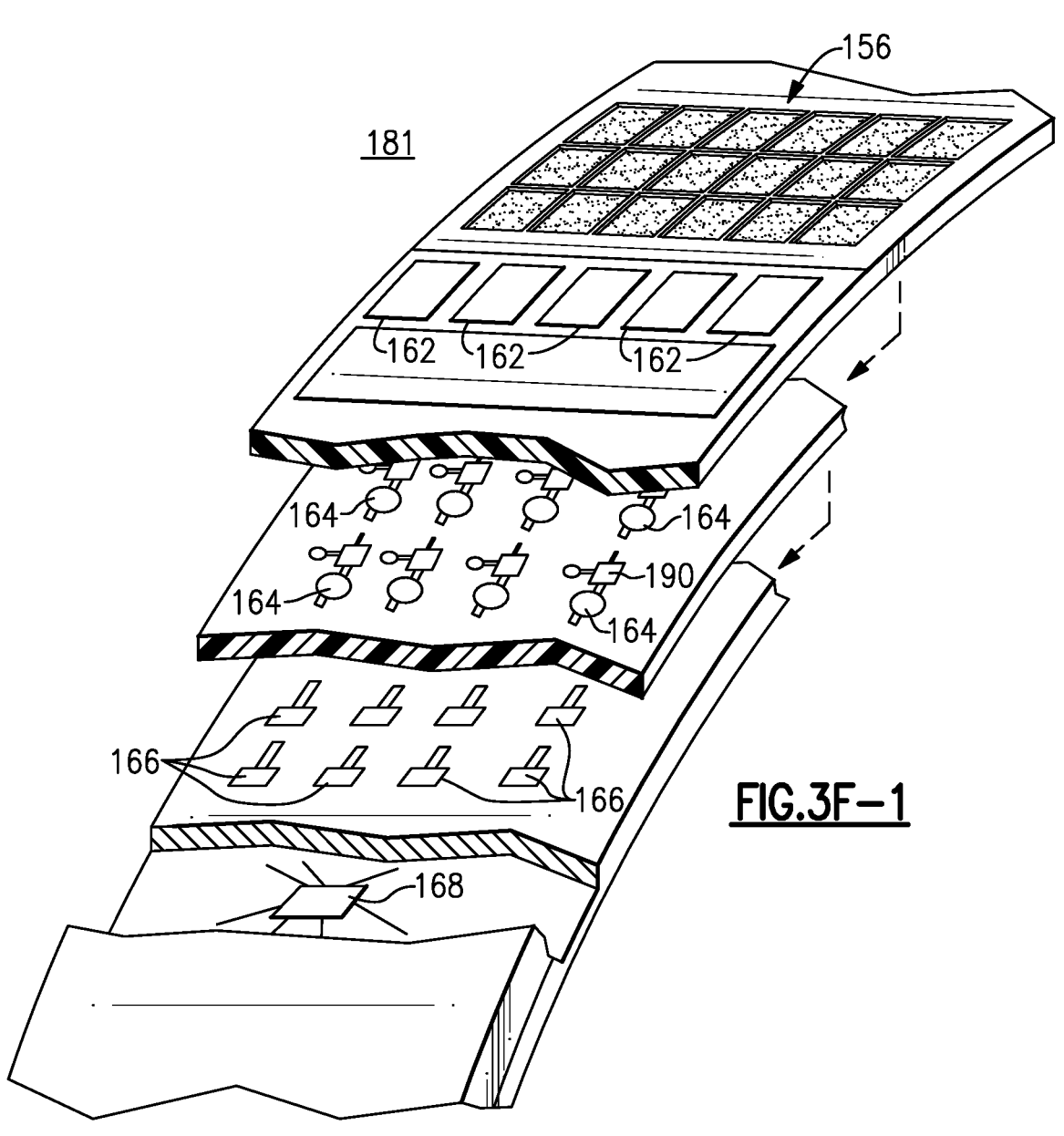
FIG.3F—1

FINGER—WIPE PAD
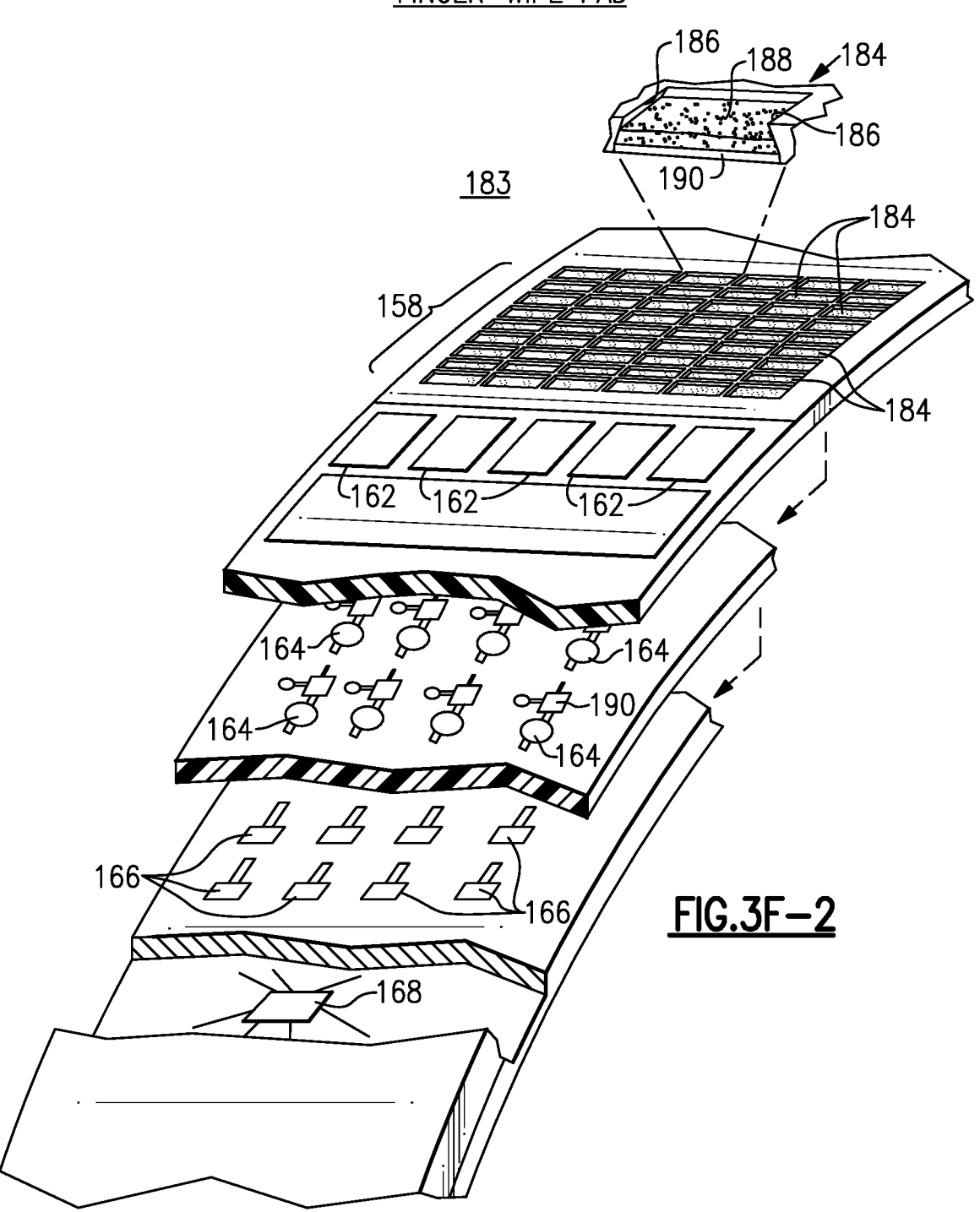
FIG.3F—2

APPLY FINGER-WIPE
PATCH TO LOCATION
ON BODY OR ON
PERSONAL ITEM

NON-INVASIVE BRACELET – DISEASE DETECTION

ILLNESS SIGNAL AUTOMATICALLY SENT TO AUTHORIZED SECOND PARTY SO AS TO PROVIDE ASSISTANCE TO BRACELET USER

207a

203

155

TRANSMIT ELECTRONICS

206

CENTRAL PROCESSING UNIT (CPU)

150

SURFACE PAD

ASSAY PROCESSING

152

203

204

203

202

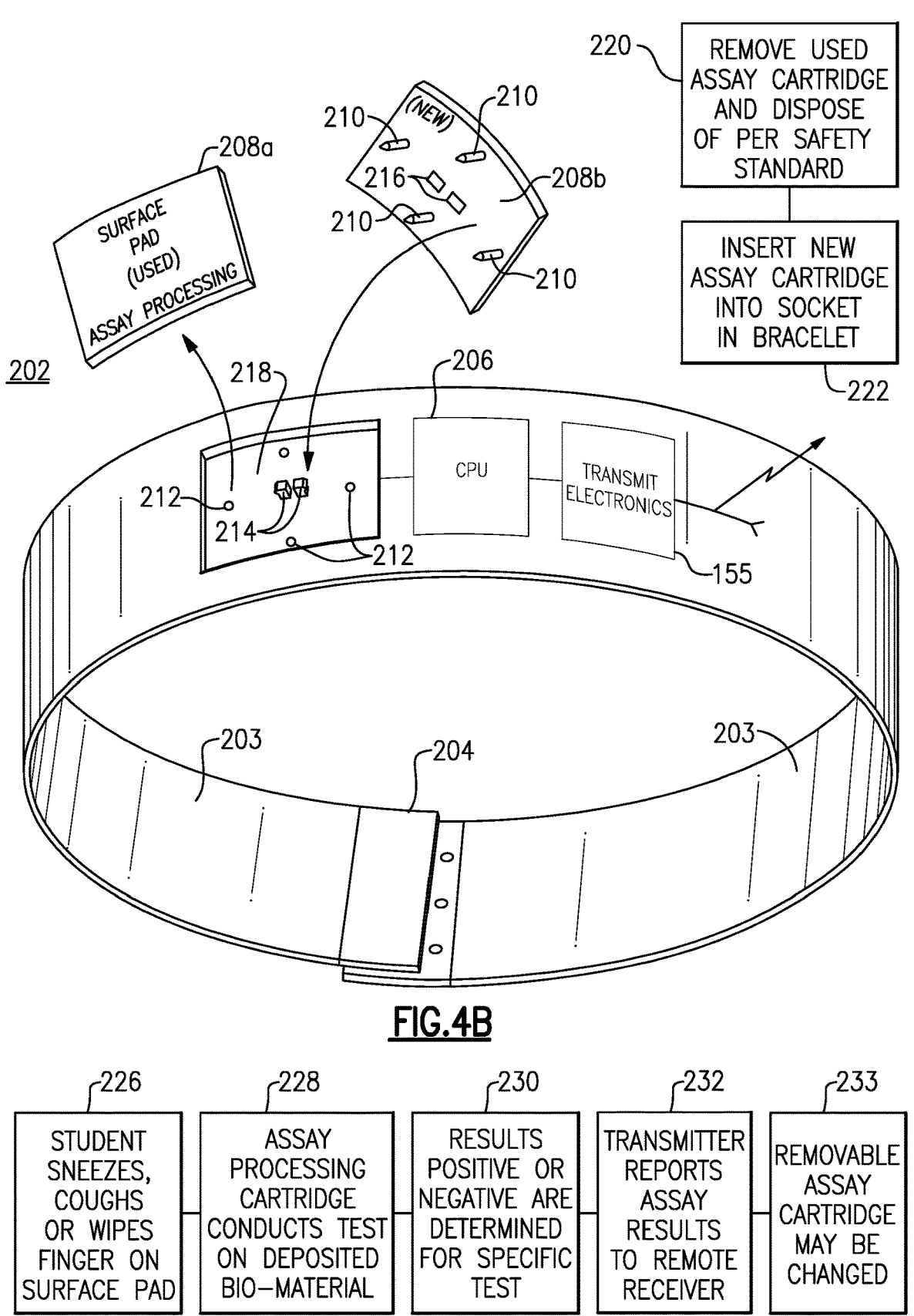

220 — REMOVE USED ASSAY CARTRIDGE AND DISPOSE OF PER SAFETY STANDARD

INSERT NEW ASSAY CARTRIDGE INTO SOCKET IN BRACELET — 222

208a — SURFACE PAD (USED) ASSAY PROCESSING

202

(NEW)

210  210  216  208b  210  210

218  206

212  214  212

CPU  TRANSMIT ELECTRONICS — 155

| 226 | 228 | 230 | 232 | 233 |
|---|---|---|---|---|
| STUDENT SNEEZES, COUGHS OR WIPES FINGER ON SURFACE PAD | ASSAY PROCESSING CARTRIDGE CONDUCTS TEST ON DEPOSITED BIO-MATERIAL | RESULTS POSITIVE OR NEGATIVE ARE DETERMINED FOR SPECIFIC TEST | TRANSMITTER REPORTS ASSAY RESULTS TO REMOTE RECEIVER | REMOVABLE ASSAY CARTRIDGE MAY BE CHANGED |

FIG.4D

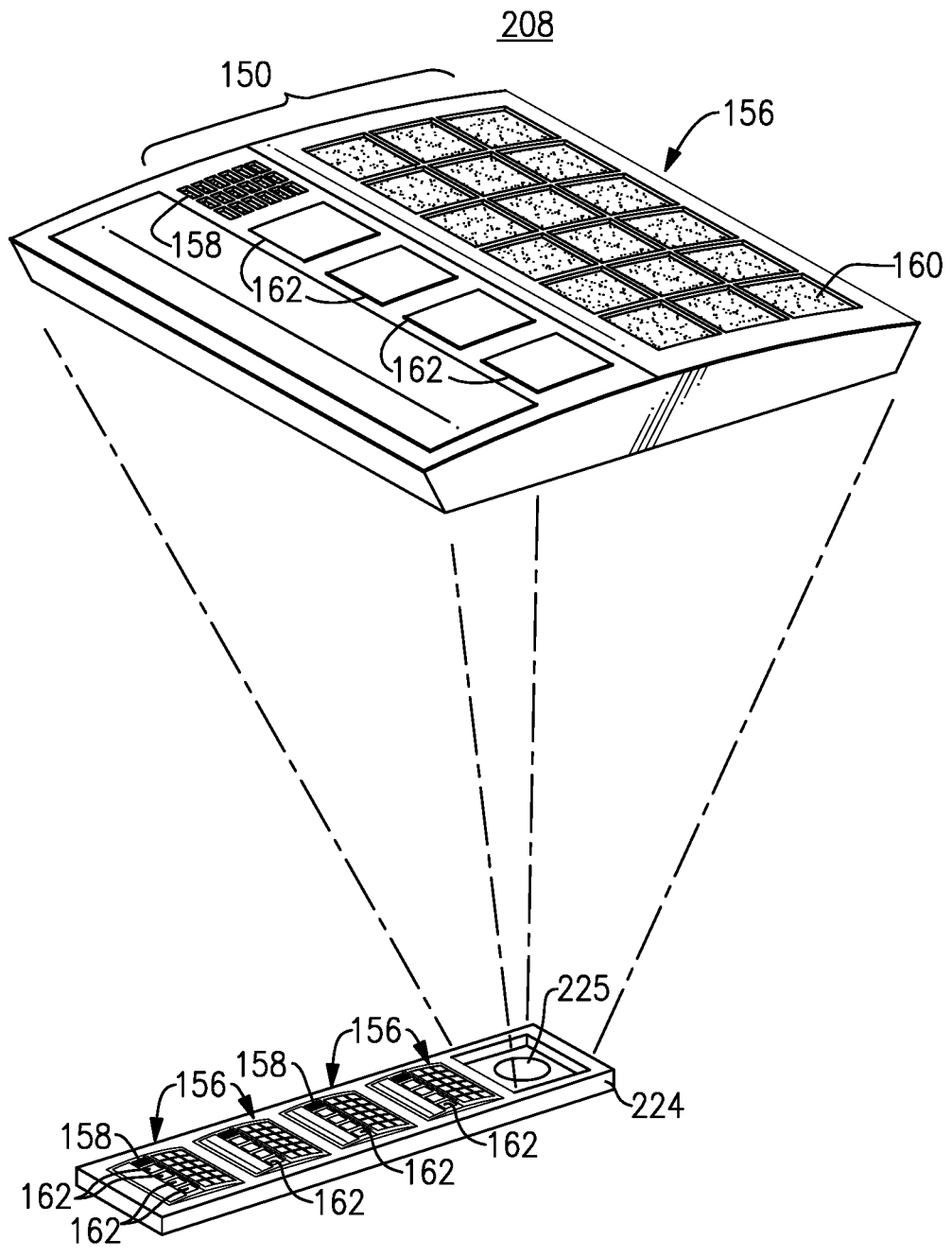
FIG.4C—1

NON-INVASIVE BRACELET – FEVER DETECTION

FEVER SIGNAL AUTOMATICALLY SENT TO AUTHORIZED SECOND PARTY SO AS TO PROVIDE ASSISTANCE TO BRACELET USER

TRANSMIT ELECTRONICS

PROCESSOR

TEMPERATURE SENSOR

NON-INVASIVE BRACELET – FEVER DETECTION

234b

207b

FEVER SIGNAL AUTOMATICALLY SENT TO AUTHORIZED SECOND PARTY SO AS TO PROVIDE ASSISTANCE TO BRACELET USER

"FEVER" "DETECTED"

235

203

155

TRANSMIT ELECTRONICS

134

PROCESSOR

132

TEMPERATURE SENSOR

203

203

204

MANDATORY USE CASE SCENARIO I
FEVER PATCH

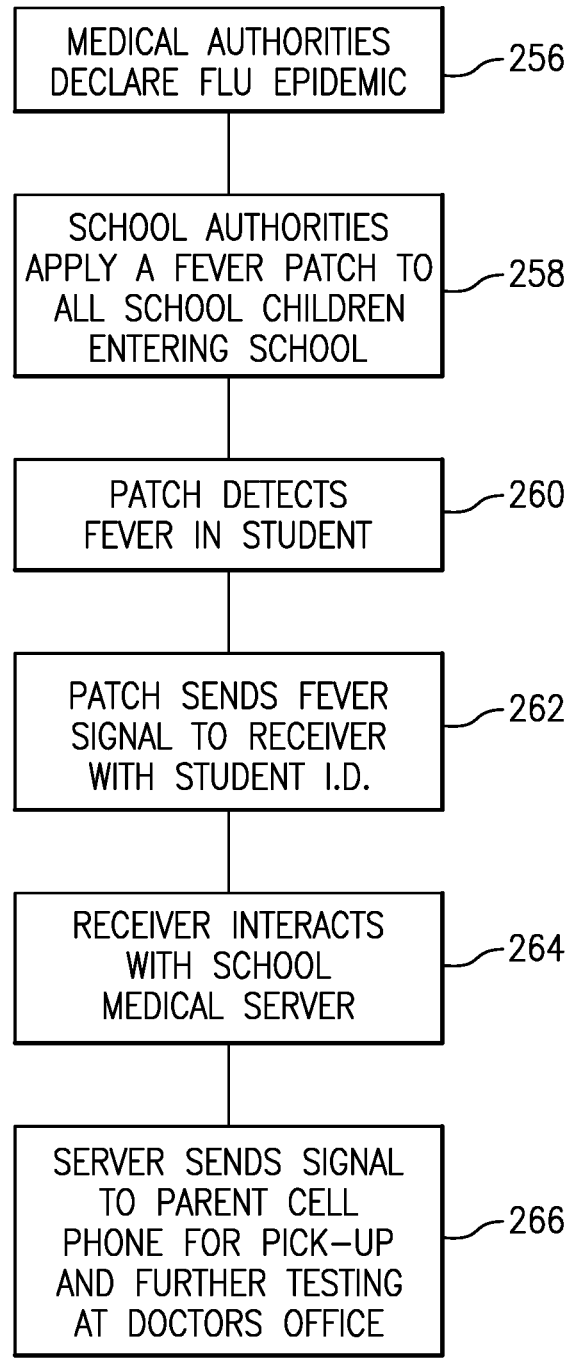

MEDICAL AUTHORITIES
DECLARE FLU EPIDEMIC — 256

SCHOOL AUTHORITIES
APPLY A FEVER PATCH TO
ALL SCHOOL CHILDREN
ENTERING SCHOOL — 258

PATCH DETECTS
FEVER IN STUDENT — 260

PATCH SENDS FEVER
SIGNAL TO RECEIVER
WITH STUDENT I.D. — 262

RECEIVER INTERACTS
WITH SCHOOL
MEDICAL SERVER — 264

SERVER SENDS SIGNAL
TO PARENT CELL
PHONE FOR PICK-UP
AND FURTHER TESTING
AT DOCTORS OFFICE — 266

FIG.7A

MANDATORY USE CASE SCENARIO II
DISEASE DETECTION PATCH

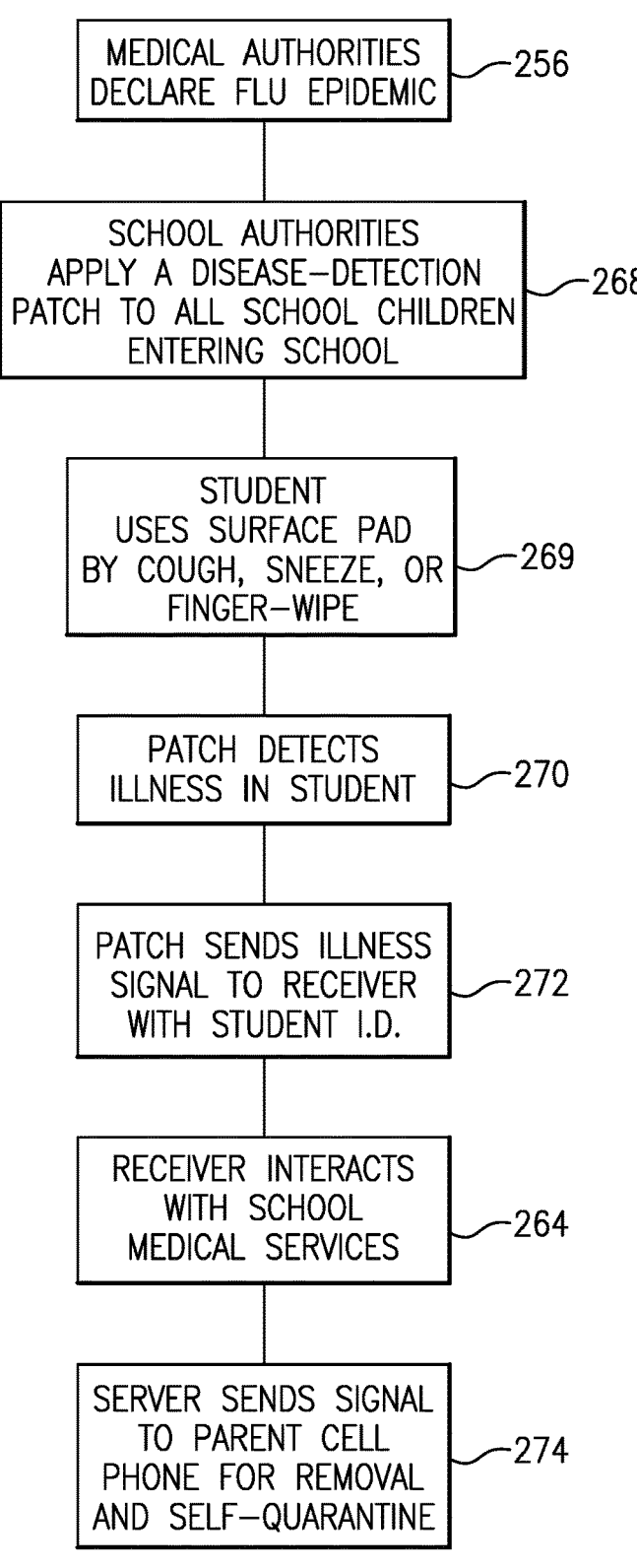

MEDICAL AUTHORITIES
DECLARE FLU EPIDEMIC —256

SCHOOL AUTHORITIES
APPLY A DISEASE—DETECTION
PATCH TO ALL SCHOOL CHILDREN
ENTERING SCHOOL —268

STUDENT
USES SURFACE PAD
BY COUGH, SNEEZE, OR
FINGER—WIPE —269

PATCH DETECTS
ILLNESS IN STUDENT —270

PATCH SENDS ILLNESS
SIGNAL TO RECEIVER
WITH STUDENT I.D. —272

RECEIVER INTERACTS
WITH SCHOOL
MEDICAL SERVICES —264

SERVER SENDS SIGNAL
TO PARENT CELL
PHONE FOR REMOVAL
AND SELF—QUARANTINE —274

FIG.7B

VOLUNTARY USE CASE SCENARIO I
FEVER PATCH

VOLUNTARY USE CASE SCENARIO I
FEVER BRACELET (SHORT RANGE)

VOLUNTARY USE CASE SCENARIO I
FEVER BRACELET (LONG RANGE)

VOLUNTARY USE CASE SCENARIO II
DISEASE DETECTION AT SCHOOL

VOLUNTARY USE CASE SCENARIO III
UNIVERSITY APPLICATION

340

SOCIAL DISTANCING – FEVER PATCH OR BRACELET

346

350a

KEEP SAFE DISTANCING

353a

136

TRANSMITTER

348a

134

PROCESSOR

132

FEVER DETECTION – TEMPERATURE SENSOR

PERSON ONE

352

RECEIVER

353b

6 FEET
2 METERS

350b

MOBILE PHONE

348b

FEVER DETECTION DEVICE

PERSON TWO

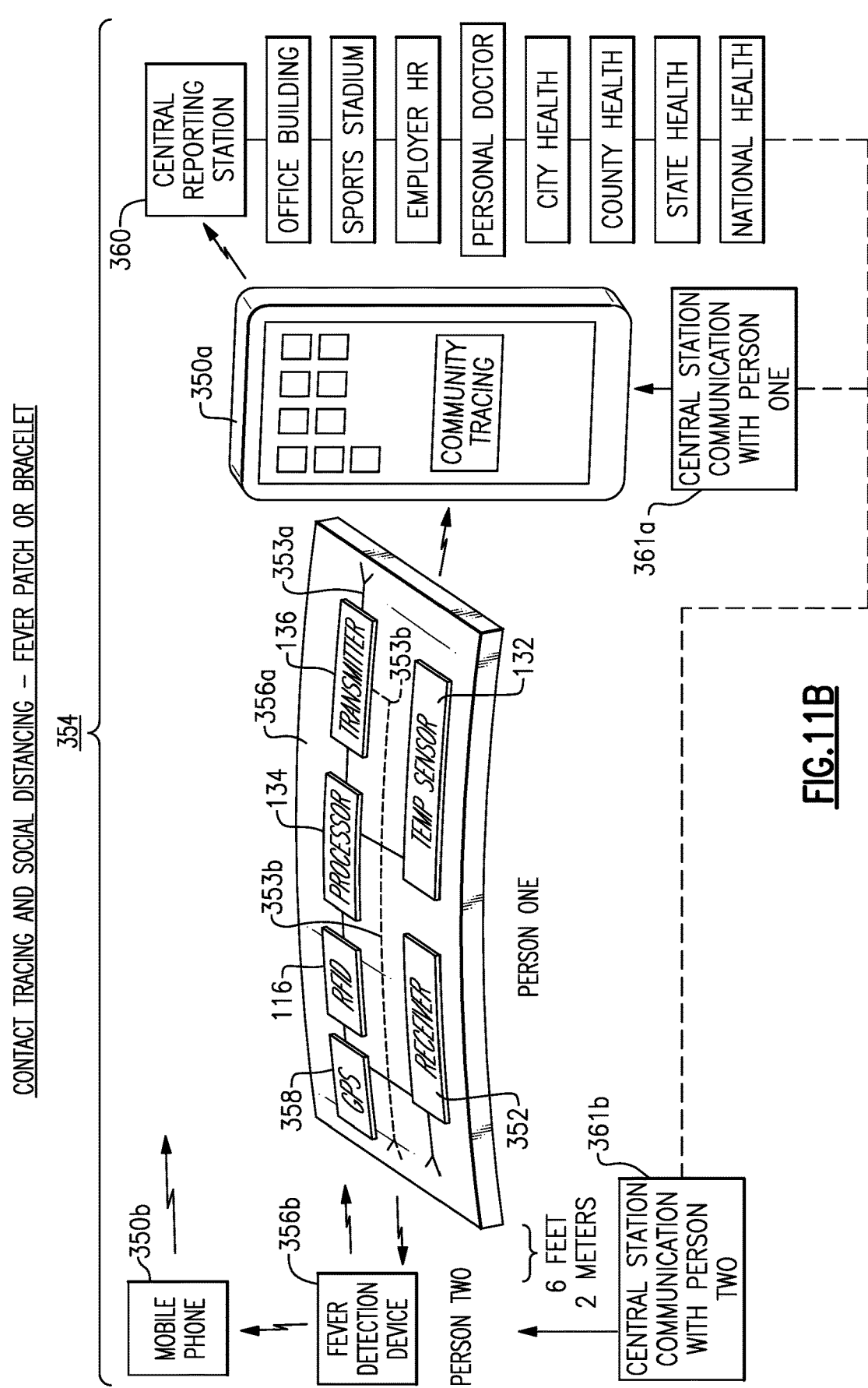

CONTACT TRACING AND SOCIAL DISTANCING – FEVER PATCH OR BRACELET

354

360

CENTRAL REPORTING STATION

OFFICE BUILDING

SPORTS STADIUM

EMPLOYER HR

PERSONAL DOCTOR

CITY HEALTH

COUNTY HEALTH

STATE HEALTH

NATIONAL HEALTH

350a

COMMUNITY TRACING

361a

CENTRAL STATION COMMUNICATION WITH PERSON ONE

353a

136　TRANSMITTER

356a

353b　TEMP SENSOR

132

134　PROCESSOR

353b

116　RFID

358　GPS

RECEIVER

352

PERSON ONE

350b　MOBILE PHONE

356b　FEVER DETECTION DEVICE

PERSON TWO

6 FEET
2 METERS

361b　CENTRAL STATION COMMUNICATION WITH PERSON TWO

FIG.11B

SOCIAL DISTANCING – DISEASE DETECTION PATCH OR BRACELET

CONTACT TRACING AND SOCIAL DISTANCING – DISEASE DETECTION
PATCH OR BRACELET
368

SELF TESTING AND REPORTING
WORKING POPULATION
<u>372</u>

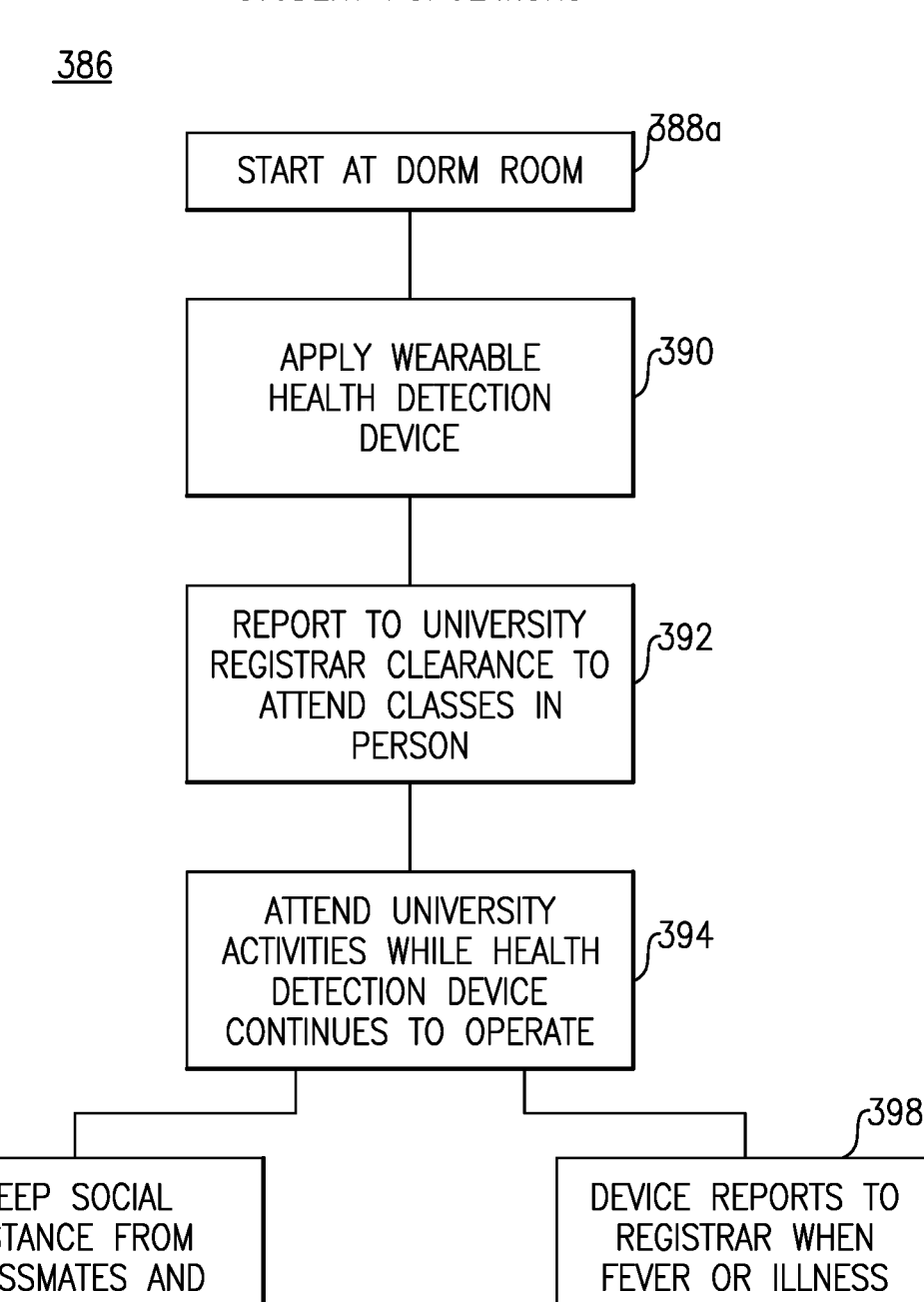

SELF TESTING AND REPORTING
STUDENT POPULATIONS

386

START AT DORM ROOM  388a

APPLY WEARABLE
HEALTH DETECTION
DEVICE  390

REPORT TO UNIVERSITY
REGISTRAR CLEARANCE TO
ATTEND CLASSES IN
PERSON  392

ATTEND UNIVERSITY
ACTIVITIES WHILE HEALTH
DETECTION DEVICE
CONTINUES TO OPERATE  394

396  KEEP SOCIAL
DISTANCE FROM
CLASSMATES AND
PROFESSORS

398  DEVICE REPORTS TO
REGISTRAR WHEN
FEVER OR ILLNESS
DETECTED

FIG.13B

<u>406</u>          FLUIDIC DIAGNOSTIC PATCH — FLOW—THROUGH

BLOOD
FLOW IN

BLOOD
OUT

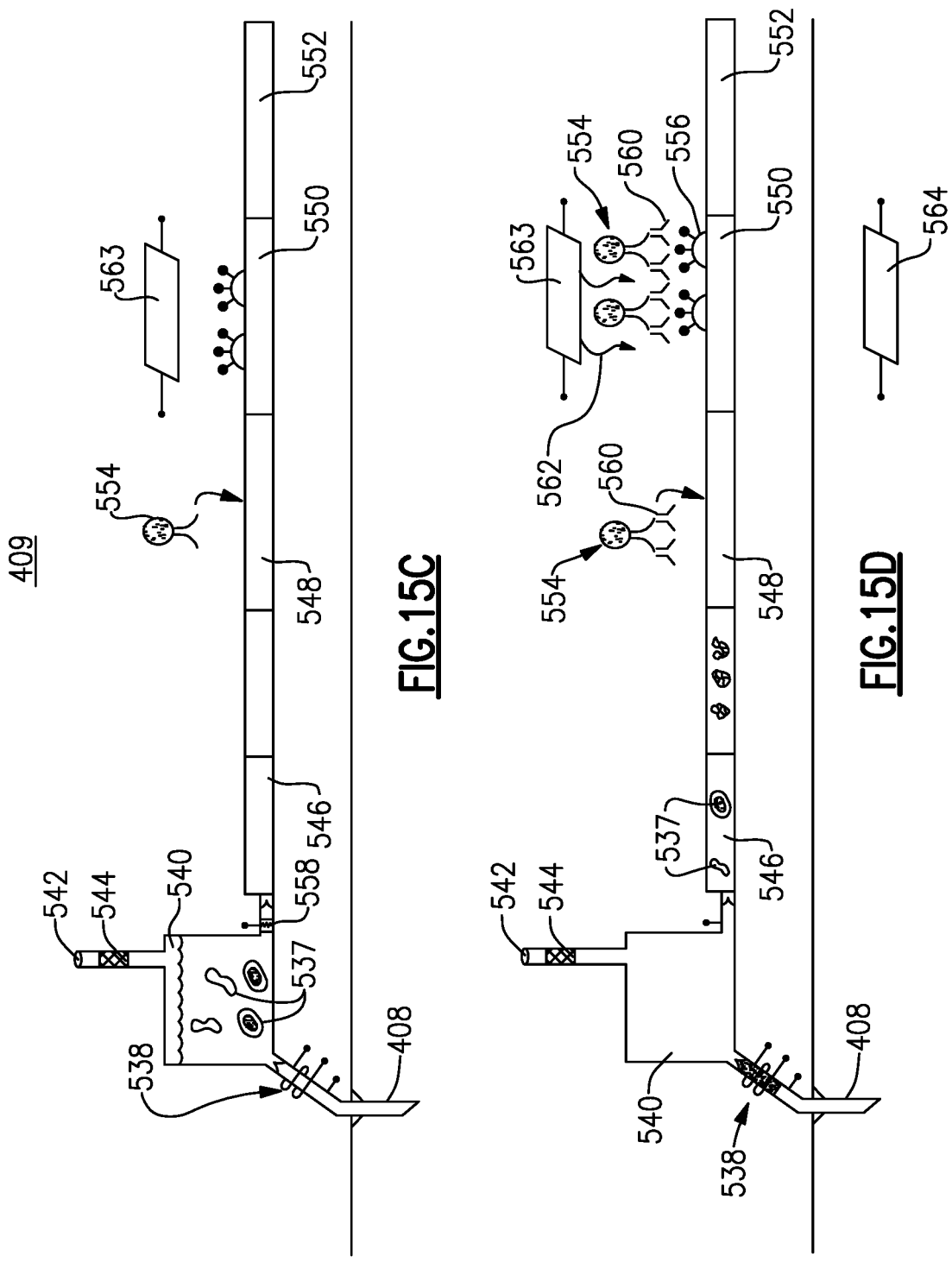

FLUIDIC DIAGNOSTIC PATCH — ABSORPTION TYPE

SWEAT ABSORPTION

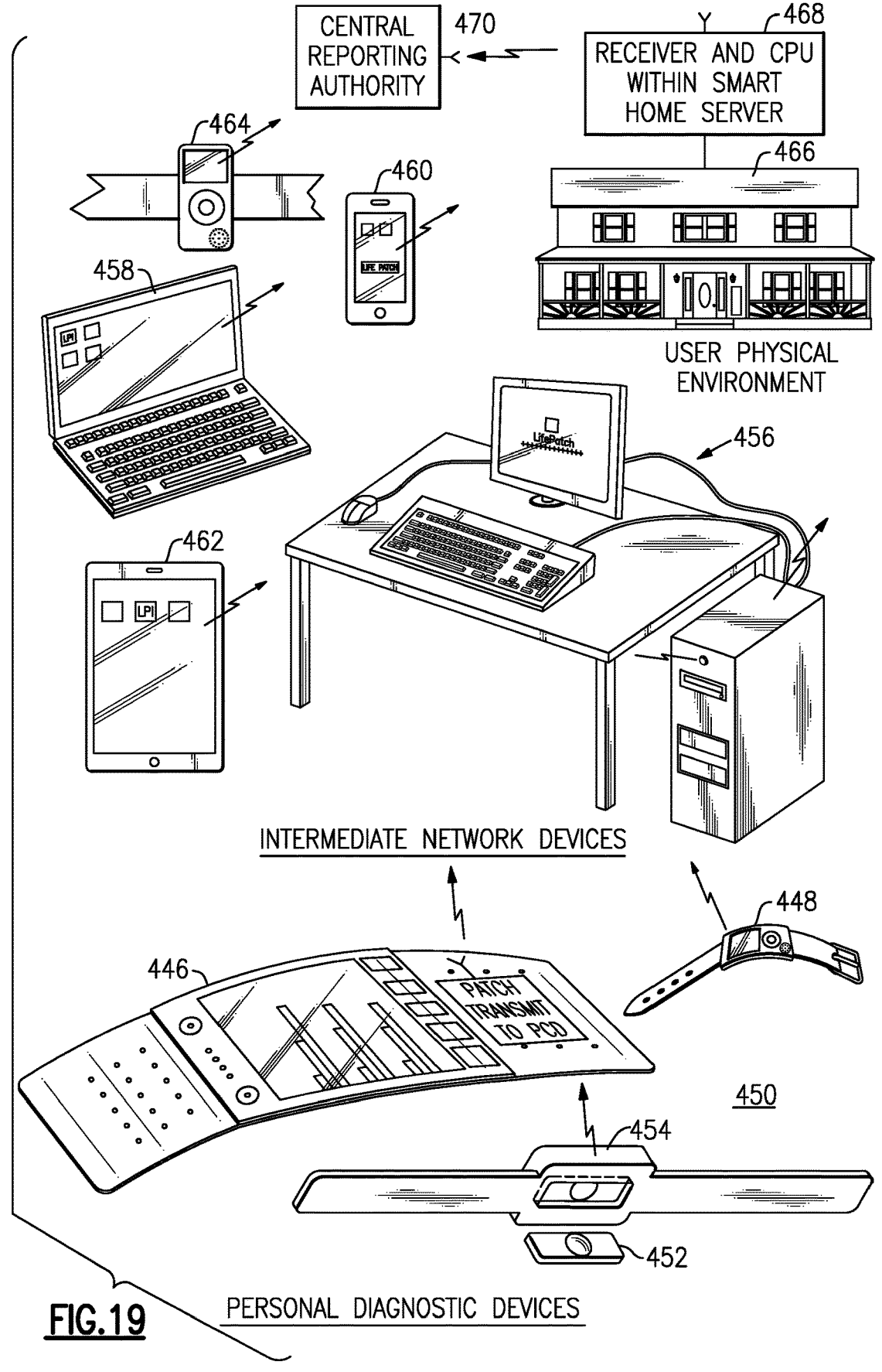
CENTRAL REPORTING AUTHORITY — 470
RECEIVER AND CPU WITHIN SMART HOME SERVER — 468
— 466
USER PHYSICAL ENVIRONMENT
— 464
— 460
458 —
— 462
— 456
LifePatch
INTERMEDIATE NETWORK DEVICES
— 448
446 —
PATCH TRANSMIT TO PCD
450
— 454
— 452
FIG.19     PERSONAL DIAGNOSTIC DEVICES

NEW YORK CITY — 18.7 MILLION

LONDON — 8.9 MILLION

SHANGHAI — 24.28 MILLION

476a

MITIGATION AND CONTACT TRACING I

MITIGATION AND CONTACT TRACING II

MITIGATION AND CONTACT TRACING III

DIAGNOSTIC PATCHES AND BRACELETS FOR PROMOTING PERSONAL AND COMMUNITY HEALTH INCLUDING RELATED PROCESSES, METHODS, AND SYSTEMS

CROSS-REFERENCE TO RELATED APPLICATIONS

This application relates to and/or references commonly assigned U.S. Provisional Application Ser. No. 62/891,279 filed Aug. 24, 2019 titled Bio-Patch Having Artificial Capillaries To Provide Continuous Blood Flow; U.S. Provisional Application Ser. No. 62/972,657 filed Feb. 11, 2020 titled Wearable Patches for Babies; U.S. Provisional Application Ser. No. 62/972,654 filed Feb. 11, 2020 titled Wearable Patches for Sports; U.S. Provisional Application Ser. No. 62/976,295 filed Feb. 13, 2020 titled Wearable Patches for Children; U.S. Provisional Application Ser. No. 62/977,691 filed Feb. 17, 2020 titled Artificial Skin Interface And Related Bio-Patches; and U.S. Provisional Applications 63/019,295 filed May 2, 2020; 63/023,512 filed May 12, 2020; 63/029,622 filed May 25, 2020; 63/042,677 filed Jun. 23, 2020; and 63/050,029 filed Jul. 9, 2020 with each thereof as hereto similarly titled Diagnostic Patches And Bracelets For Promoting Personal And Community Health Including Related Processes, Methods, And Systems, all of which being commonly assigned are herein incorporated by reference.

INCORPORATION BY REFERENCE

The documents attached to our prior filing hereof as Appendices 1, 2, and 3 as provided in U.S. Provisional Application Ser. No. 63/023,512 filed May 12, 2020 similarly titled Diagnostic Patches And Bracelets For Promoting Personal And Community Health Including Related Processes, Methods, And Systems are expressly hereinto incorporated by reference in their respective entireties, and their corresponding disclosures are to be considered part of the specification of the present application. And thus with more particularity, referenced Appendices 1, 2, and 3 as filed in 63/023,512 are as follows:

Appendix 1 of said 63/023,512 is a copy of the above-mentioned commonly-assigned U.S. Provisional Application Ser. No. 62/976,295 filed Feb. 13, 2020 titled Wearable Patches for Children, which includes a copy of U.S. Provisional Application Ser. No. 62/972,657 filed Feb. 11, 2020 titled Wearable Patches for Babies and a copy of U.S. Pat. No. 9,133,024 as two of its own appendices.

Appendix 2 of said 63/023,512 is a copy of the above-mentioned commonly-assigned U.S. Provisional Application Ser. No. 62/977,691 filed Feb. 17, 2020 titled Artificial Skin Interface And Related Bio-Patches, with its own appendix which is a copy of the foregoing U.S. Pat. No. 9,133,024.

Appendix 3 of said 63/023,512 is a copy of the above-mentioned commonly-assigned U.S. Provisional Application Ser. No. 62/972,654 filed Feb. 11, 2020 titled Wearable Patches for Sports, with its own appendix which is a copy of the foregoing U.S. Pat. No. 9,133,024.

BACKGROUND OF THE INVENTION

1. Field of the Invention

This invention relates in general to health and wellness and, in particular, to personal diagnostic devices and information networks. More specifically, but without restriction to the particular embodiments hereinafter described in accordance with the best modes of practice, this invention relates to health and wellness patches and bracelets for children and adults including related diagnostic and statistical processes, methods, and systems for maintaining personal and community health and wellness, as well as private and public networks for communicating information regarding personal and community health and wellness conditions.

2. General Discussion and Related Art

Health and wellness of individuals and organized communities have been a concern since the dawn of time. From the first recorded pandemic in world history which is believe to be the Antonine Plague of 165-180 AD with an estimated loss of five million lives, to the Bubonic Plague of 1347-1351 with 200 million deaths, to the Spanish Flu of 1917-1918 with an estimated 40-50 million lost lives worldwide, to HIV/AIDS beginning in 1981 with currently an estimated 25-35 million lost lives, to the more recent outbreaks such as SARS, Swine Flu, MERS, Ebola, and COVID-19, and to the annual recurring common cold and flu season, organized society has been struggling with containment and mitigation by simple methods of hand washing and social distancing to the more recent technologically advanced developments of modern anti-viral drugs, therapeutics, and vaccines which can all but completely eradicate a targeted pathogen from continued existence.

The present inventions disclosed herein take advantage of the widespread use and global extent of the Internet and the now ubiquitous personal use of smart phones worldwide as well as certain well-known implementing technologies that have placed these devices and networks in continuous daily use by hundreds of millions of people worldwide. The present inventions disclosed herein further build upon the advances disclosed in commonly assigned U.S. Pat. No. 9,133,024 issued on Sep. 15, 2015 titled Personal Diagnostic Devices Including Related Methods and Systems.

The inventors hereof believe that nature provides pre-signals to the onset of disease with one such being fever and that there exist an untold number of additional such pre-signals or symptoms yet to be discovered. These pre-signals may be both external-environmental and body-internal, and when body-internal may exist and/or present at the bio-molecular level or even bio-atomic level. Thus when referring to such like hereinafter, the terms "bio-molecular pre-signal" and "bio-atomic pre-signal" may be employed accordingly as regards the detection thereof and the diagnosis of disease correlated thereto. As such, some of the inventions hereof are associated with such known pre-signals as fever and detecting the possible presence or confirmed presence of pathogens including viruses and bacterium as well as currently known biological indicators resulting therefrom. Thus as such, the inventors hereof provide these inventions as herein directed, described, and disclosed to improved personal and community conditions, and also further provide all such as a platform to be applied and/or adapted to any such health and wellness pre-signals, symptoms, and/or bio-indicators to be discovered hereafter.

BRIEF DESCRIPTION OF THE DRAWING FIGURES

Various aspects of the present inventions together with additional features contributing thereto and advantages accruing therefrom will be apparent from the following description of the preferred embodiments of these inventions which are shown in the accompanying drawing figures with like reference numerals indicating like components throughout, wherein.

Figure 3A:
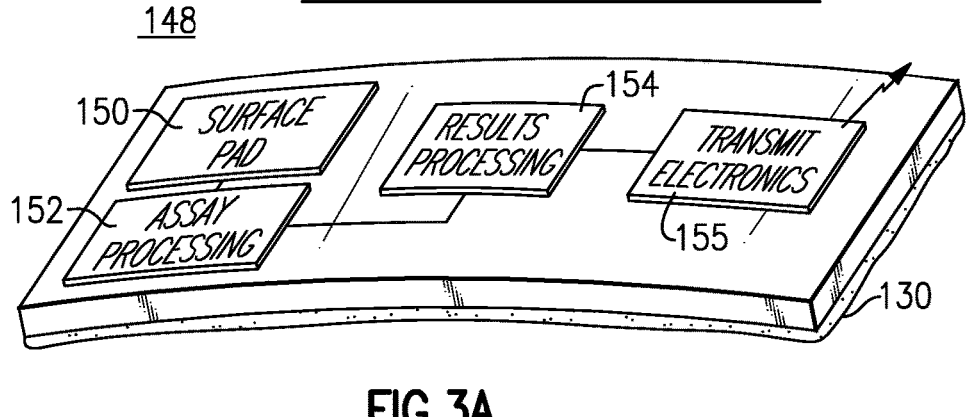
Figure 3B:
Figures 3C, 3D, 3E:
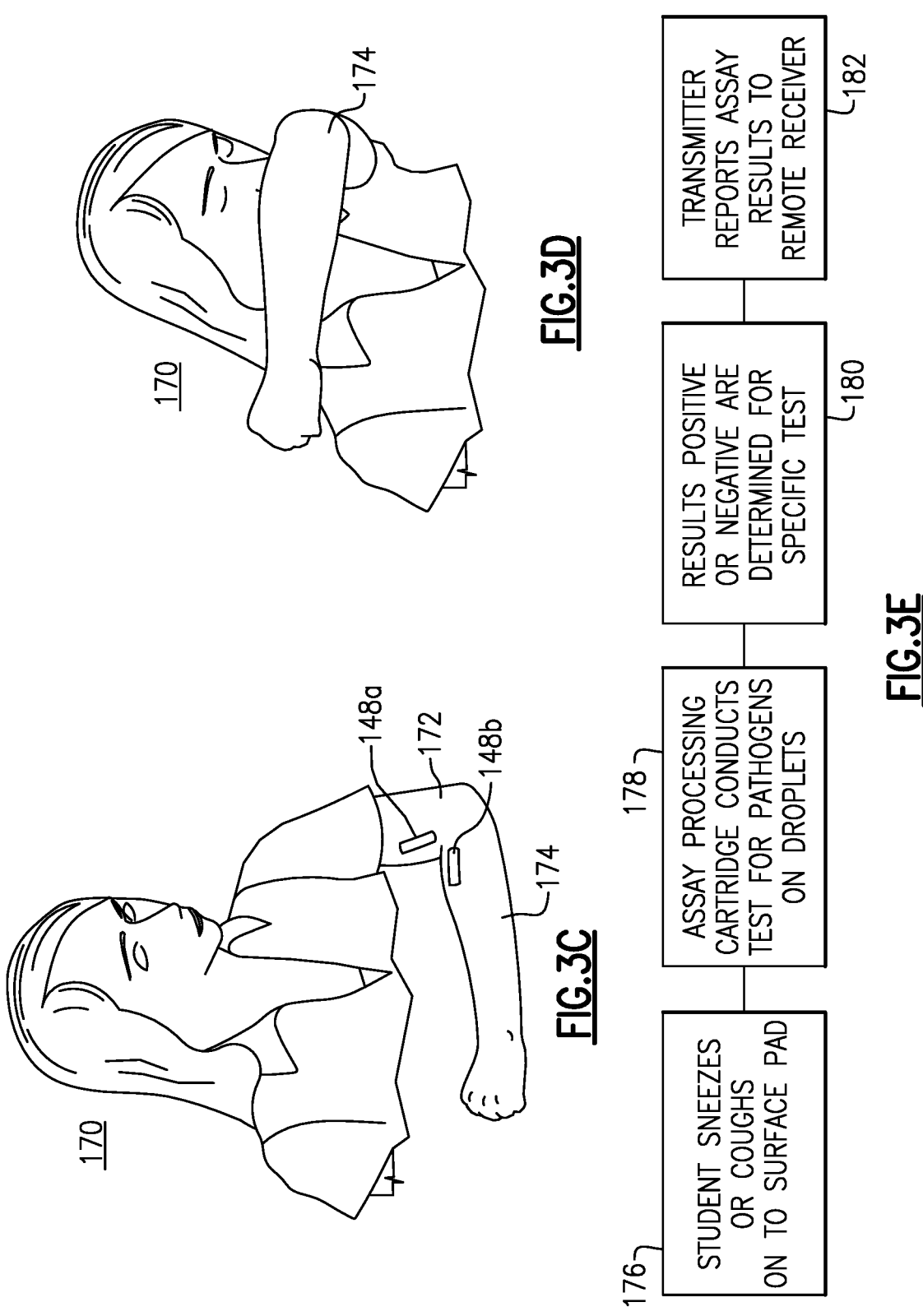
Figures 3G, 3H, 3I:
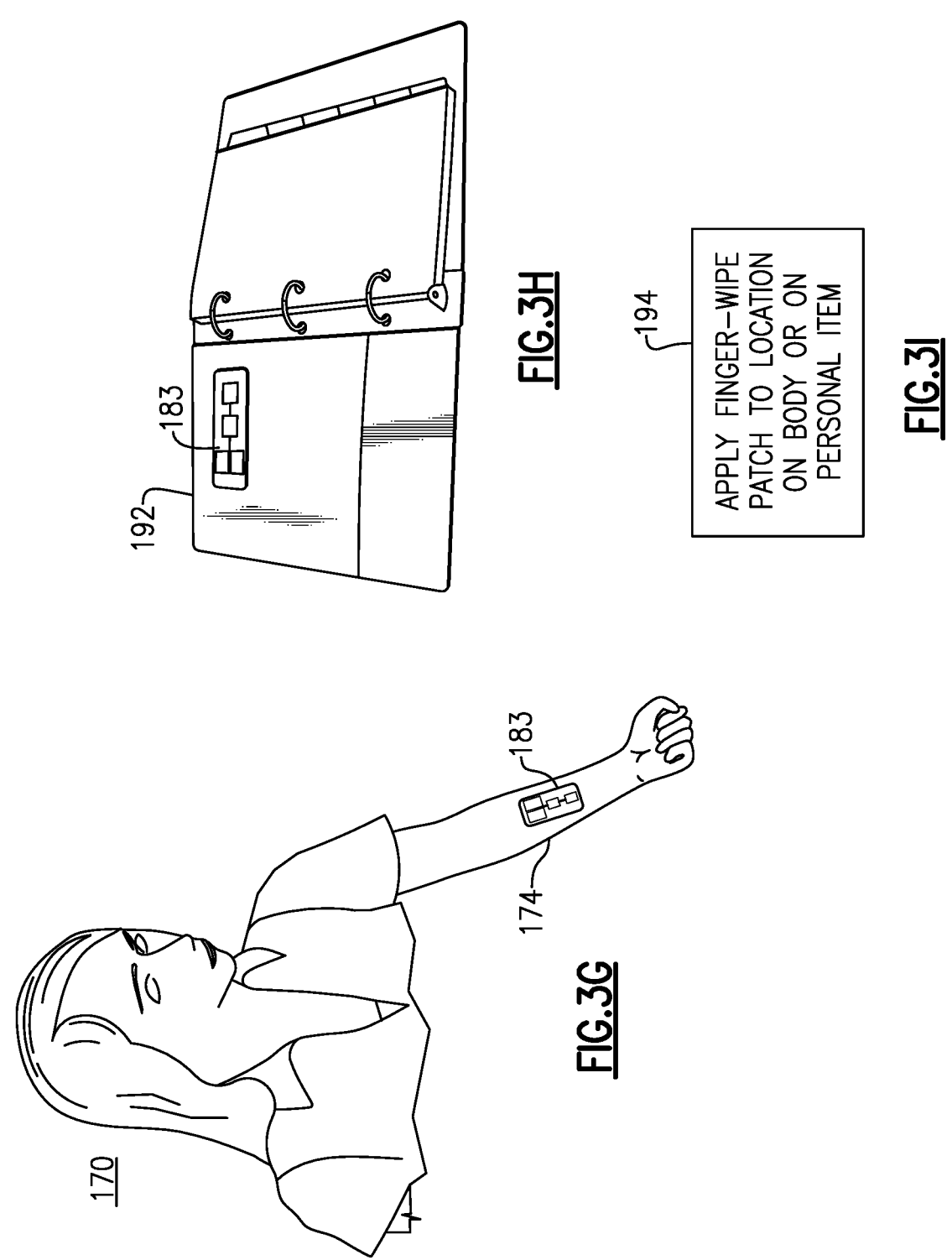
Figures 3J, 3K:
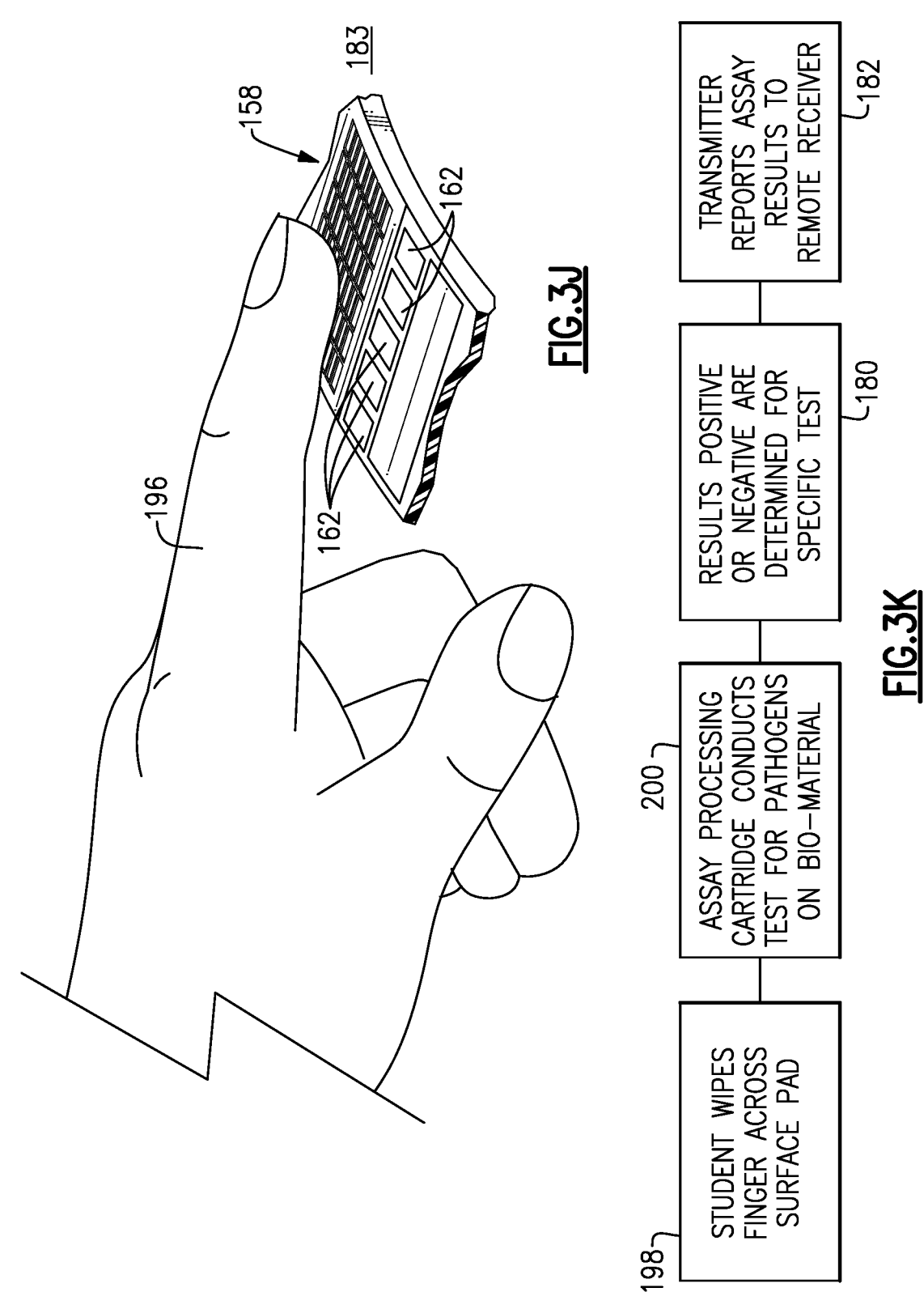
Figure 4A:
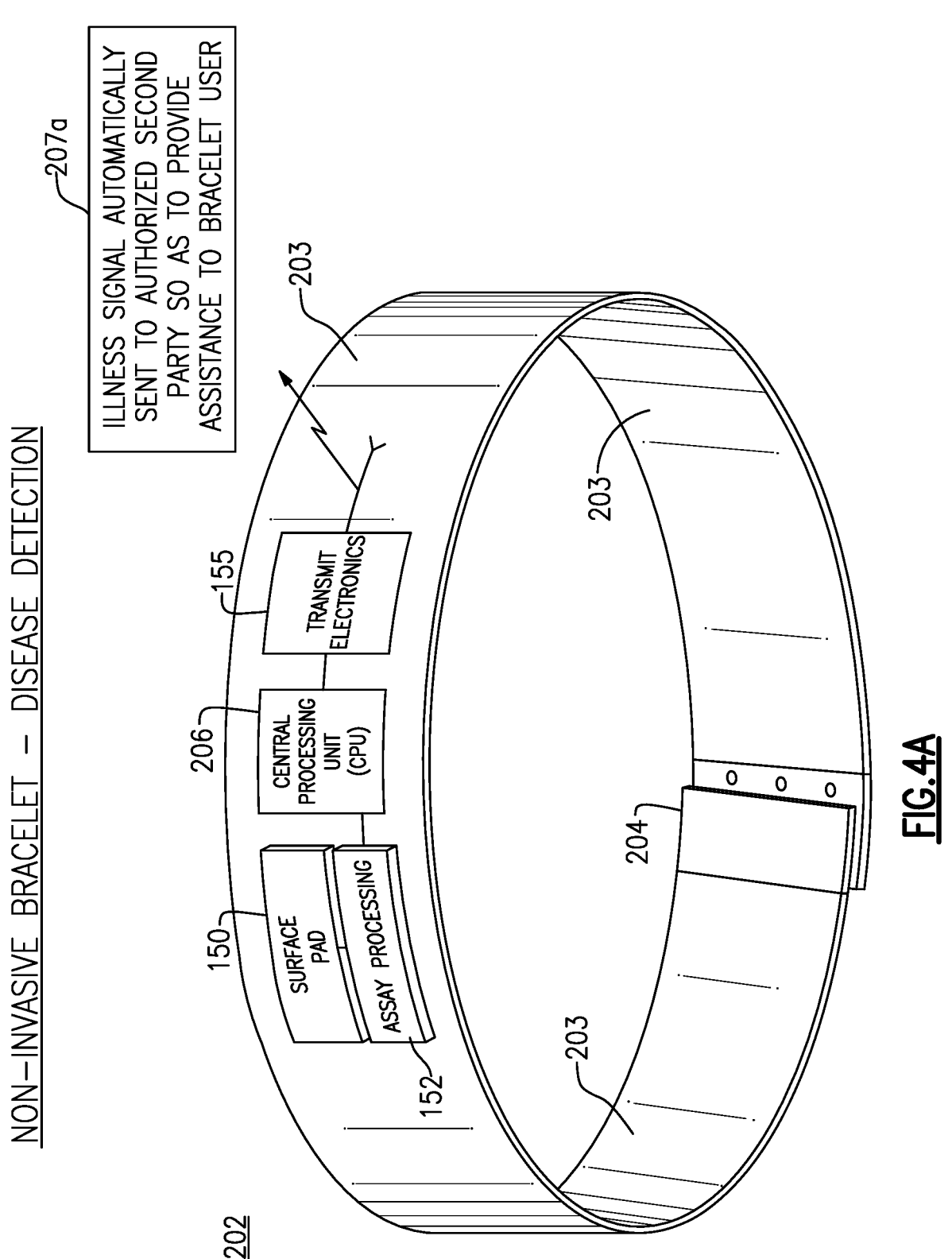
Figures 2, 4C:
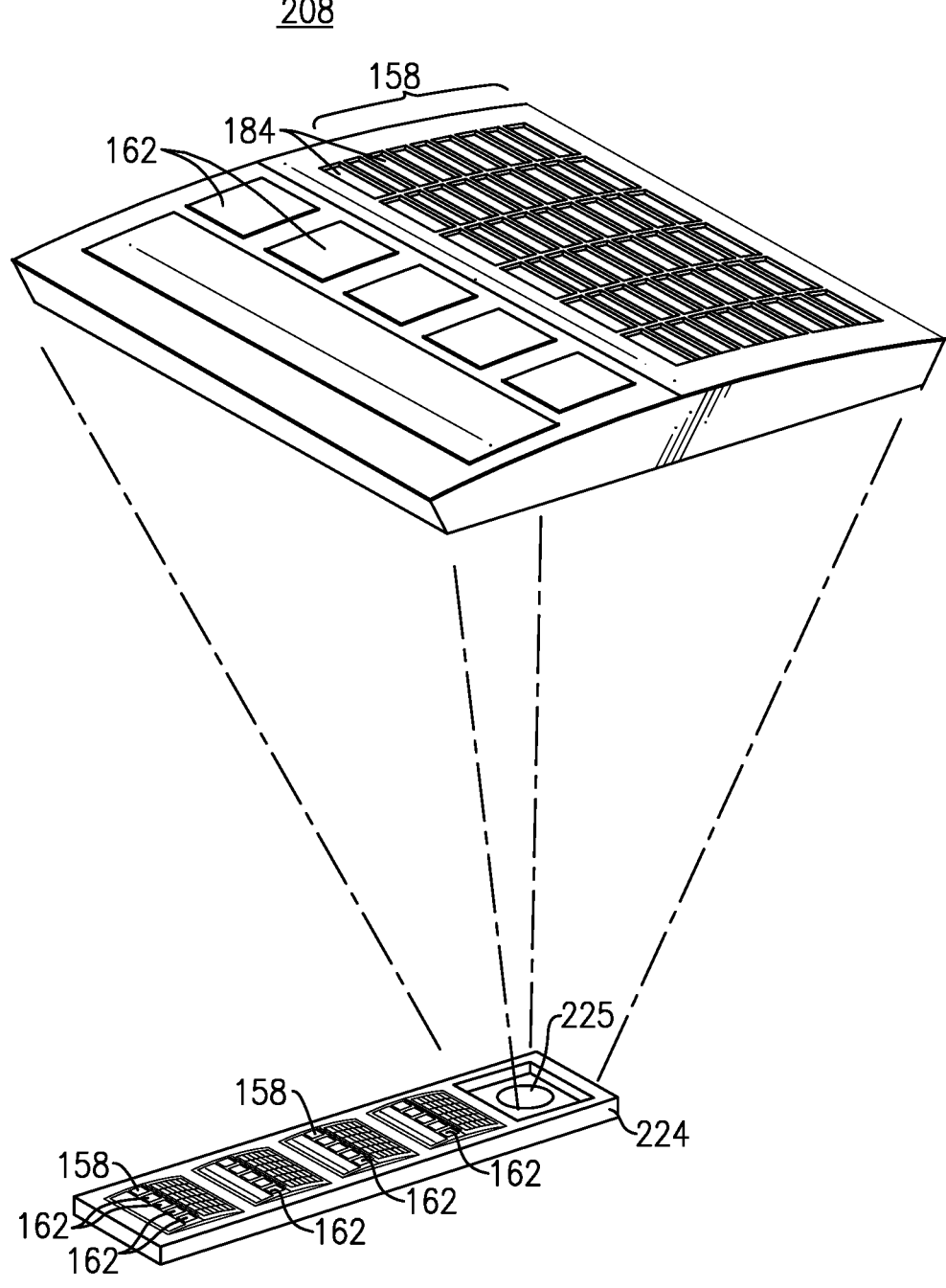
FIG. 2A is a perspective schematic view of a non-invasive patch device according to one particular embodiment hereof used to detect a fever temperature of a user thereof.
FIG. 2B is a block diagram showing the principal steps of one method of implementing the fever patch device of FIG. 2A.
Figures 1, 4E:
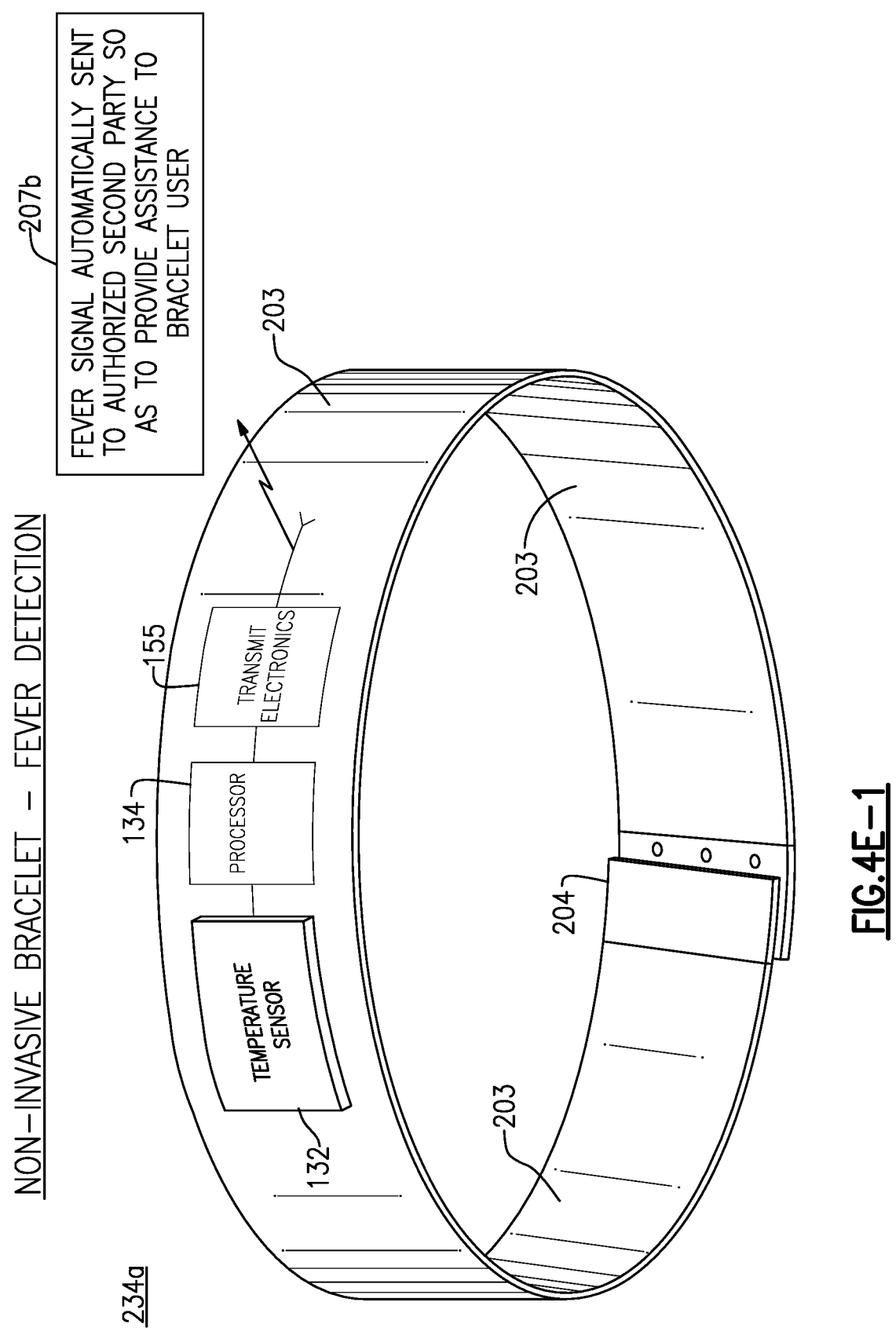
Figures 2, 4E:
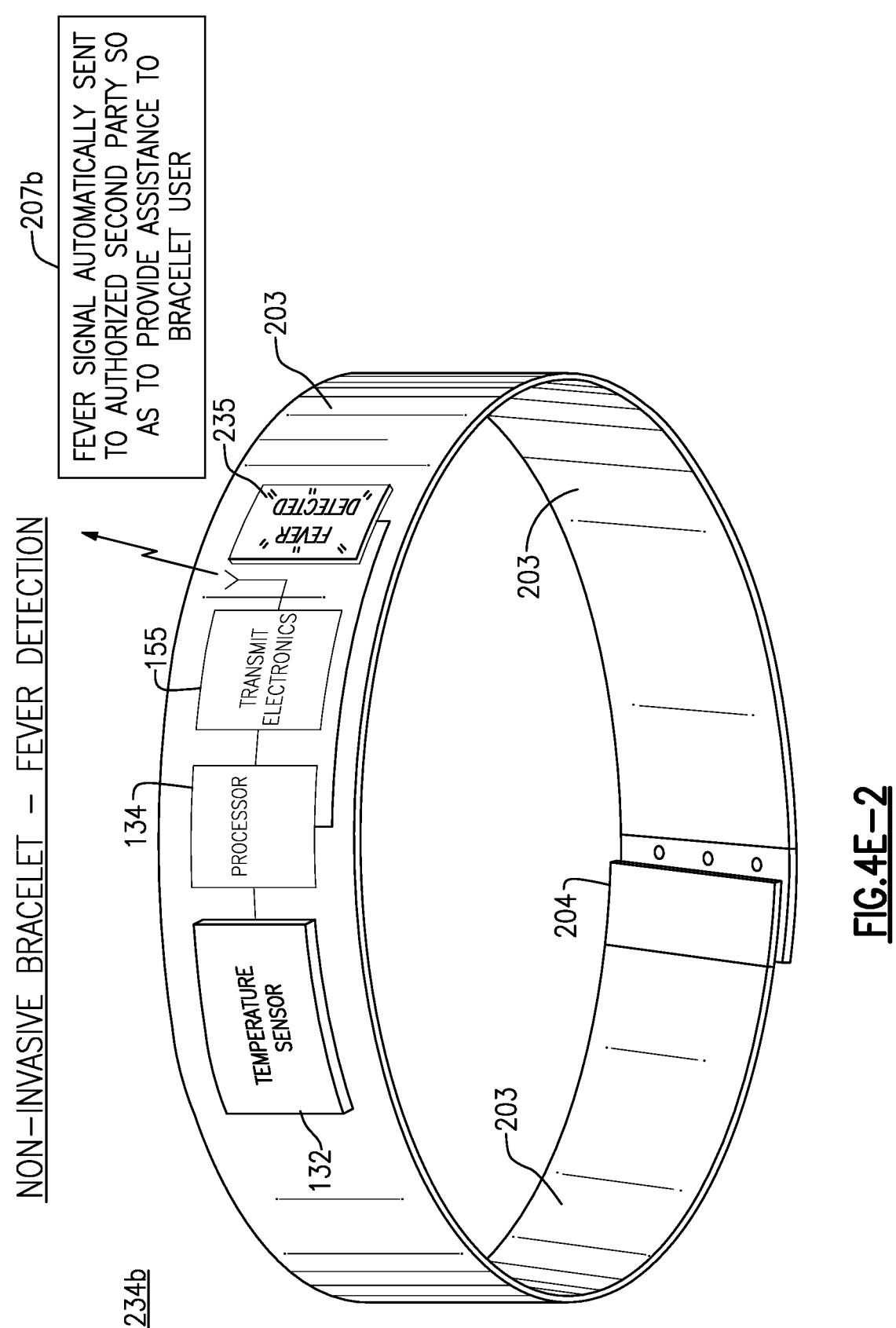
Figure 5:
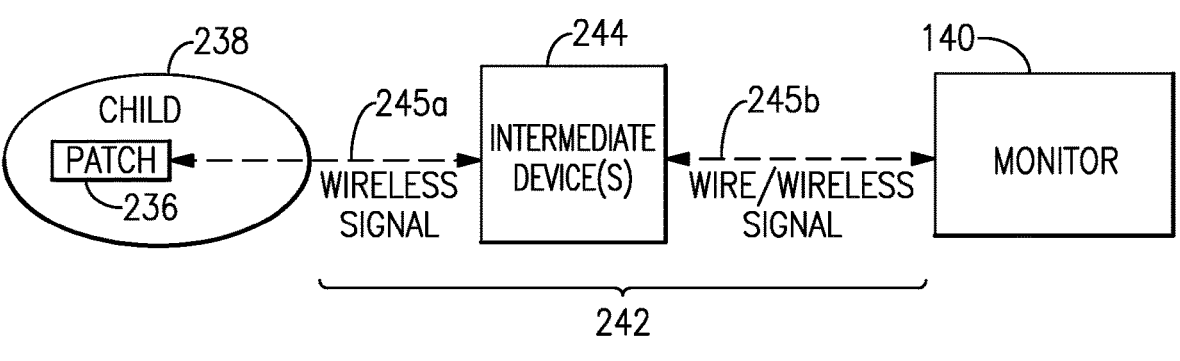
Figure 6A:
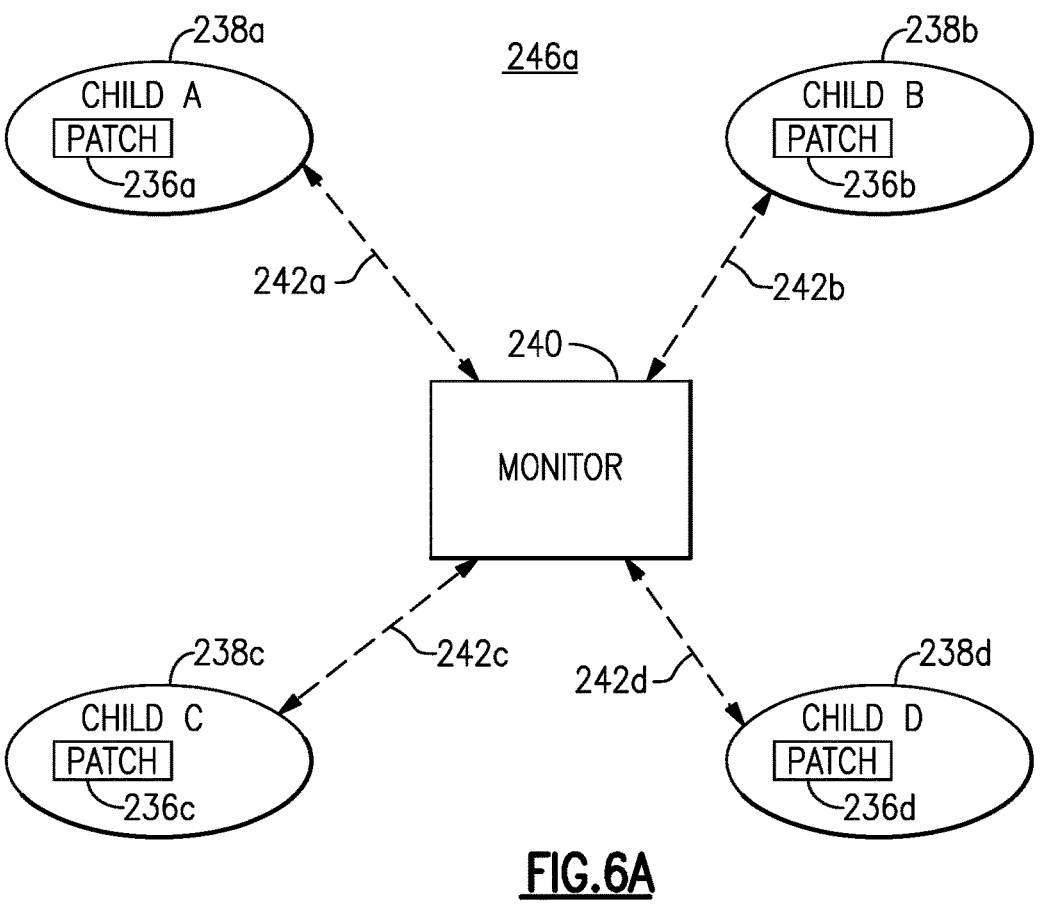
Figure 6B:
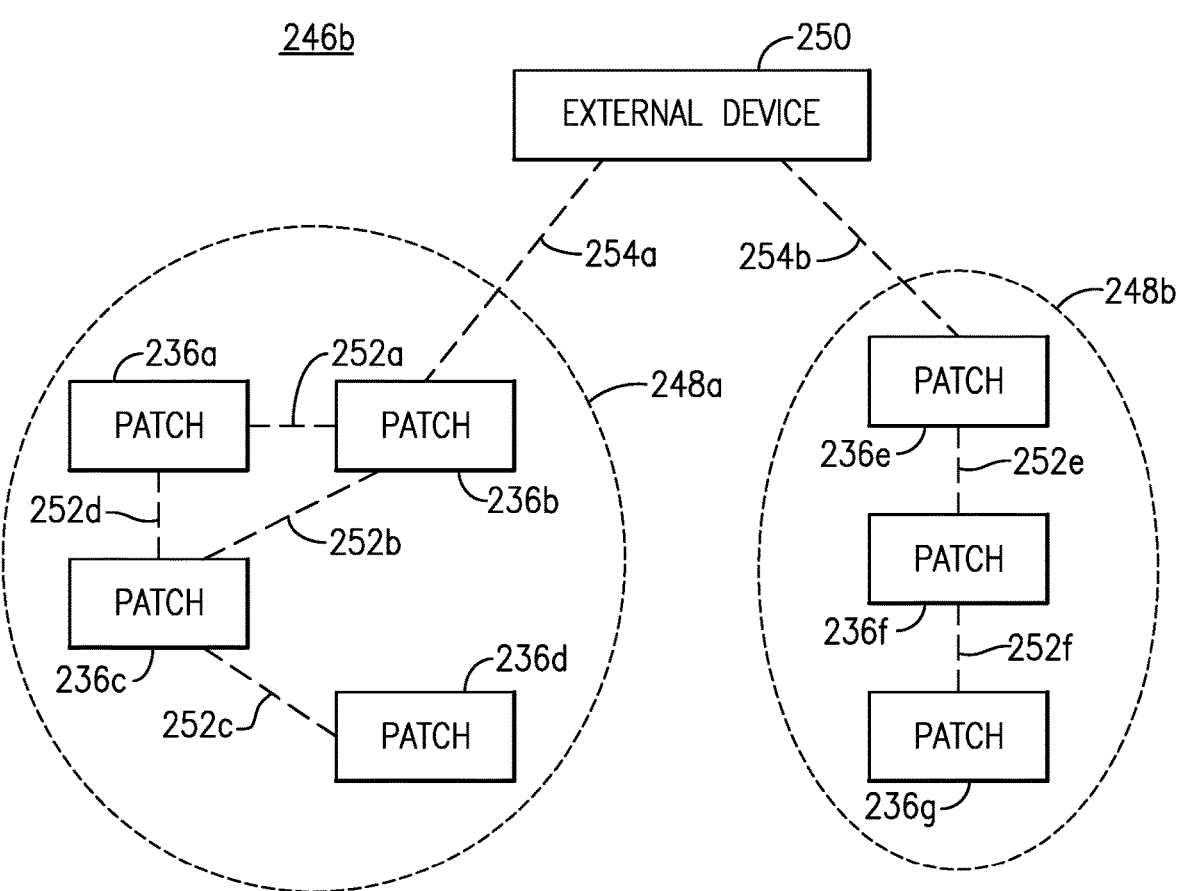
Figures 1, 8A:
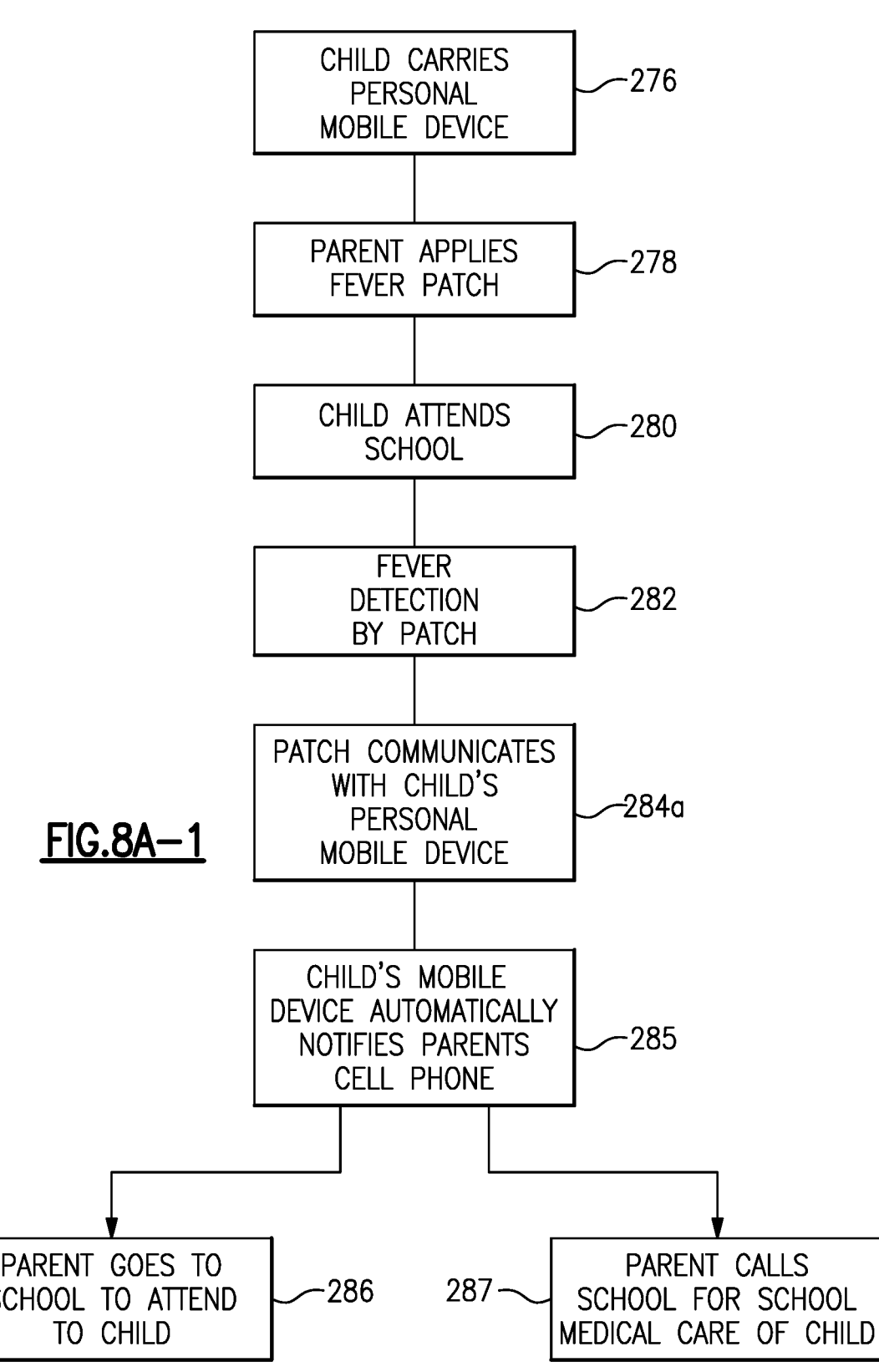
Figures 2, 8A:
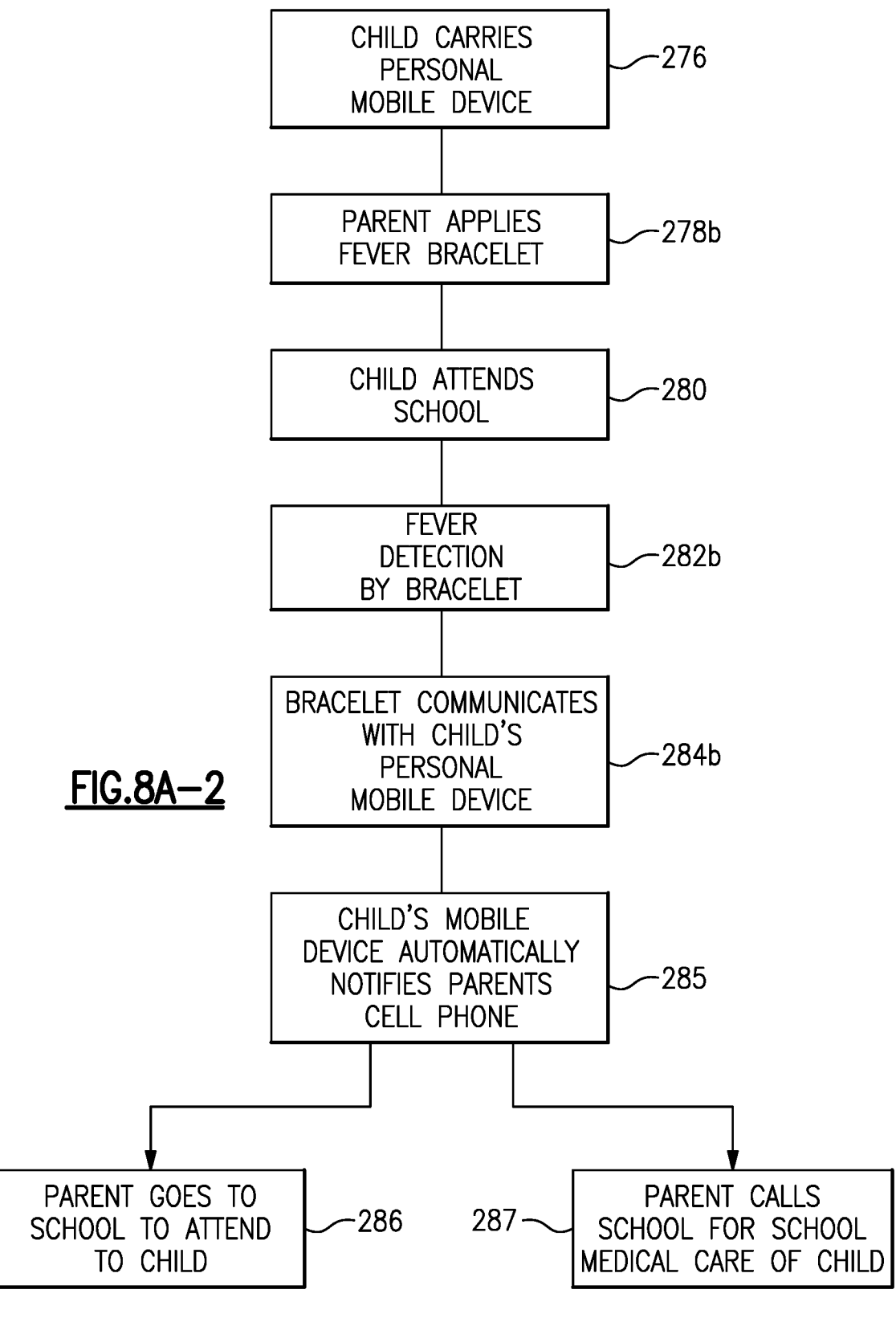
Figures 3, 8A:
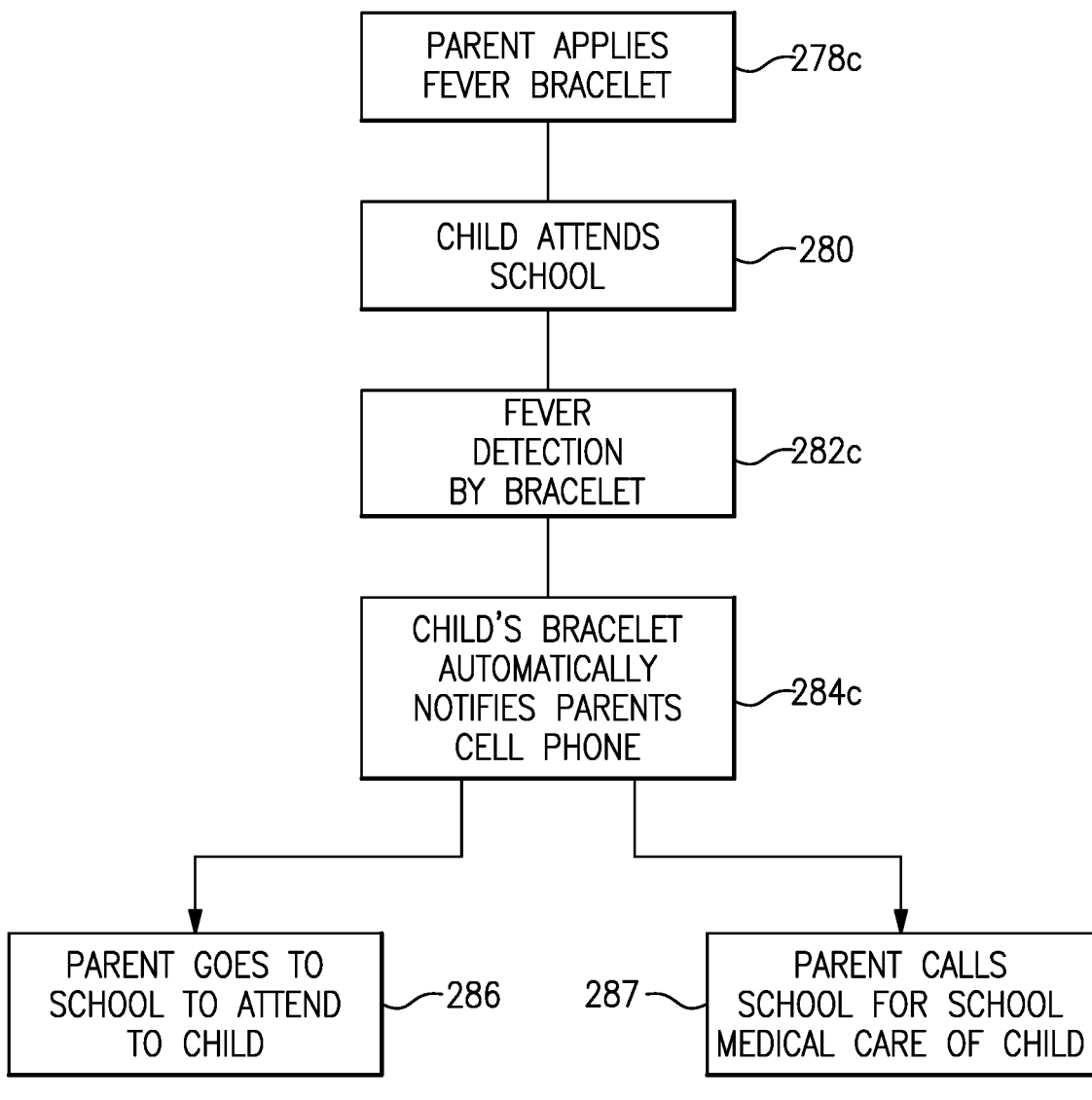
Figure 8B:
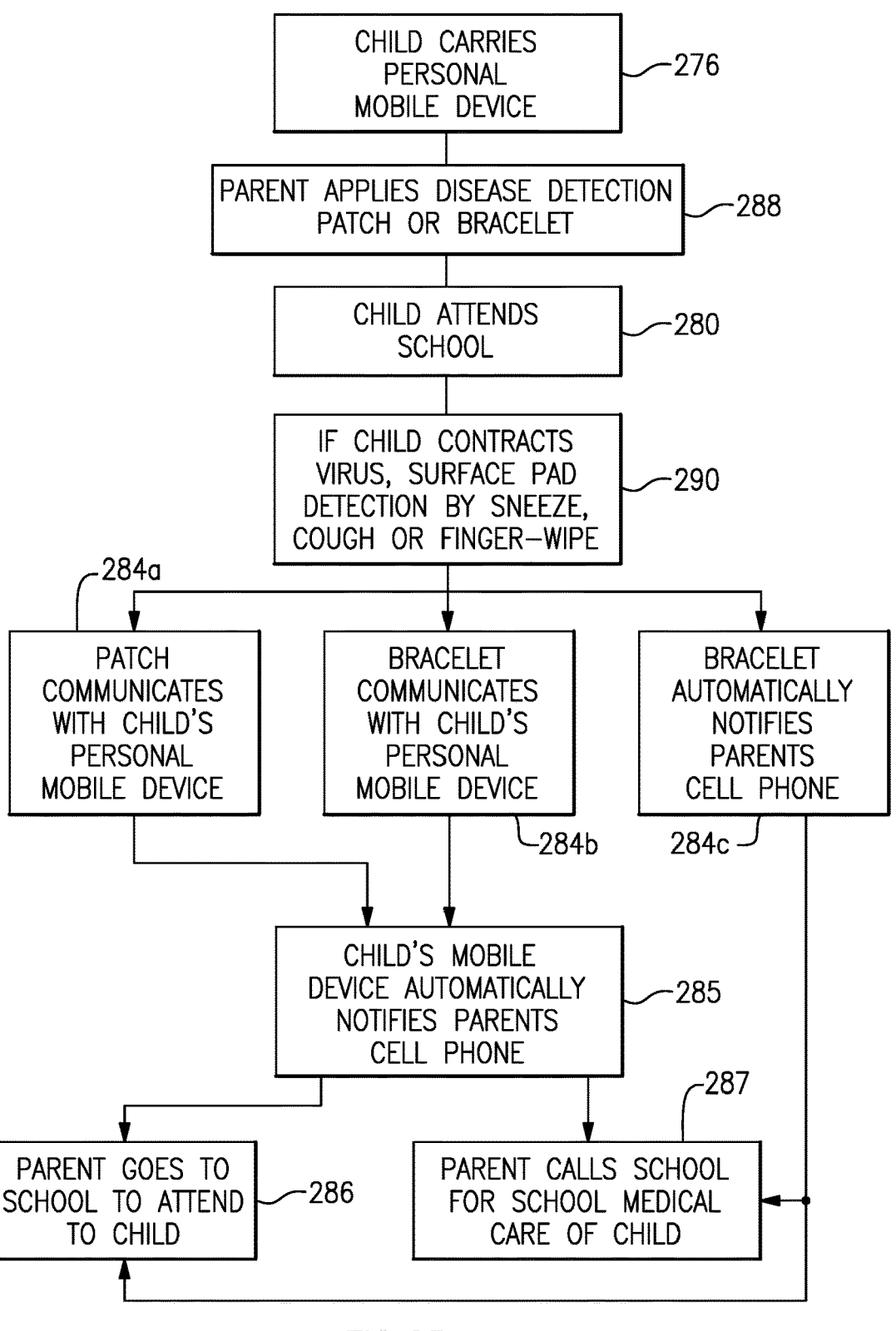
Figures 1, 8C:
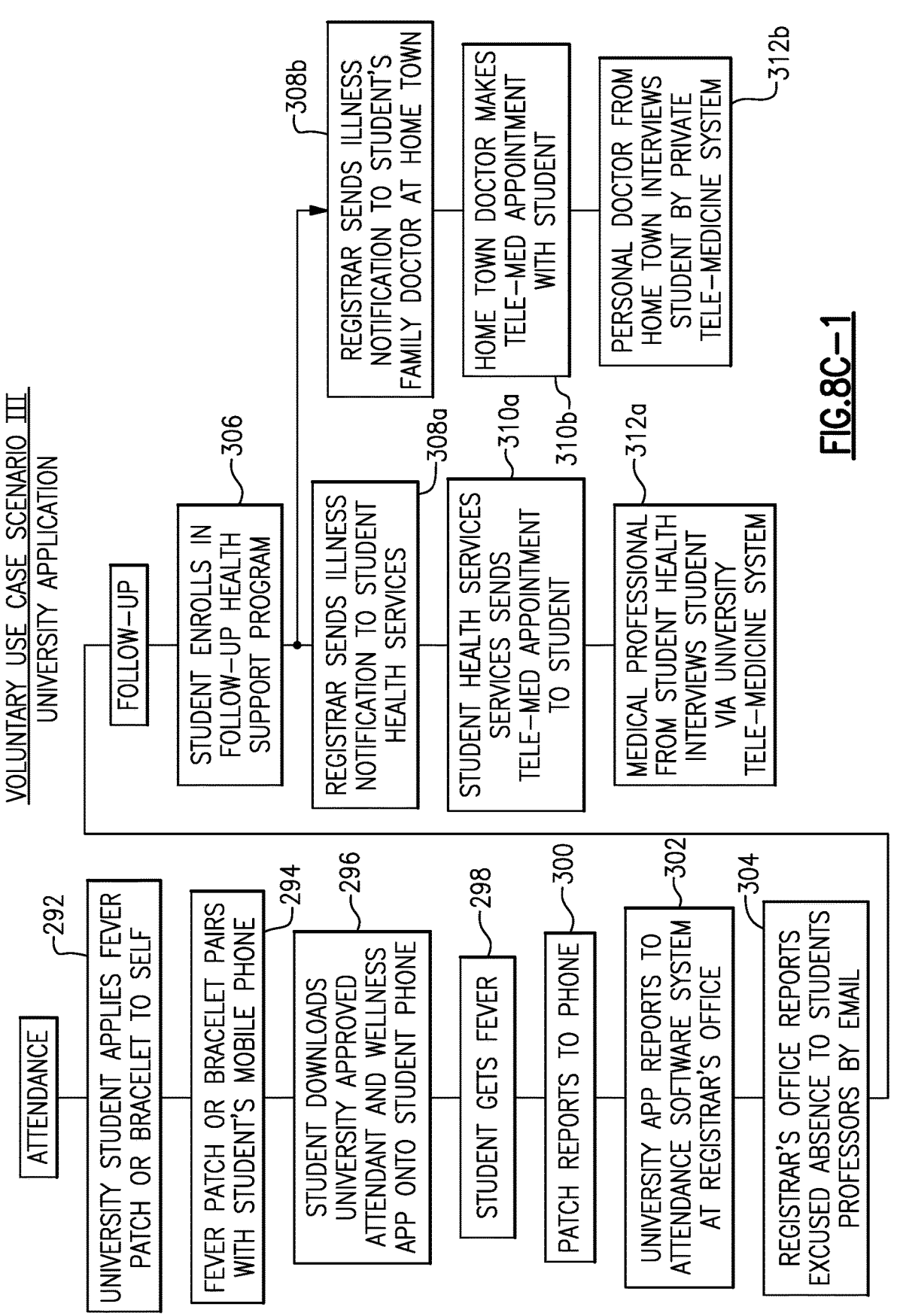
Figures 2, 8C:
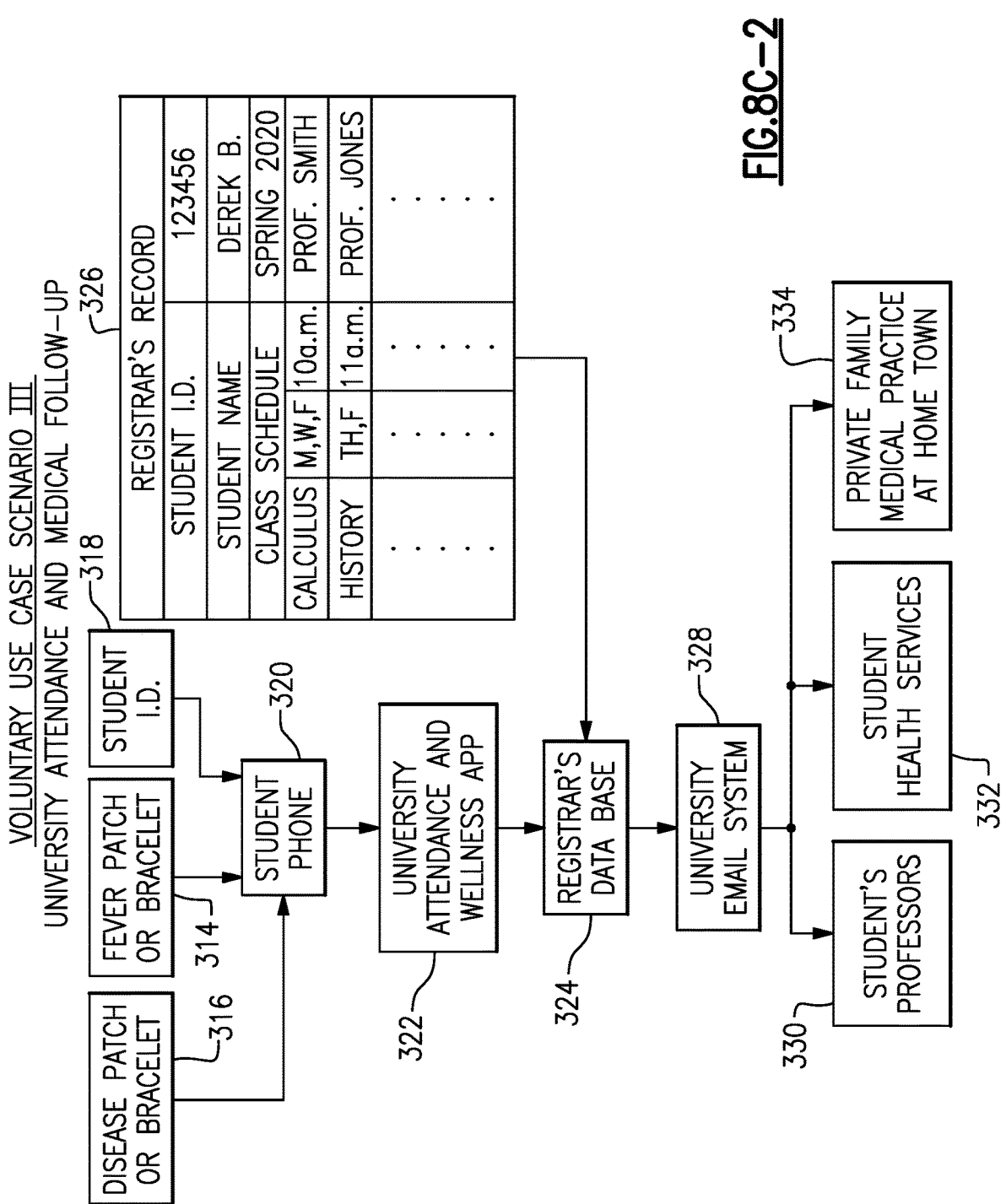
Figure 9:
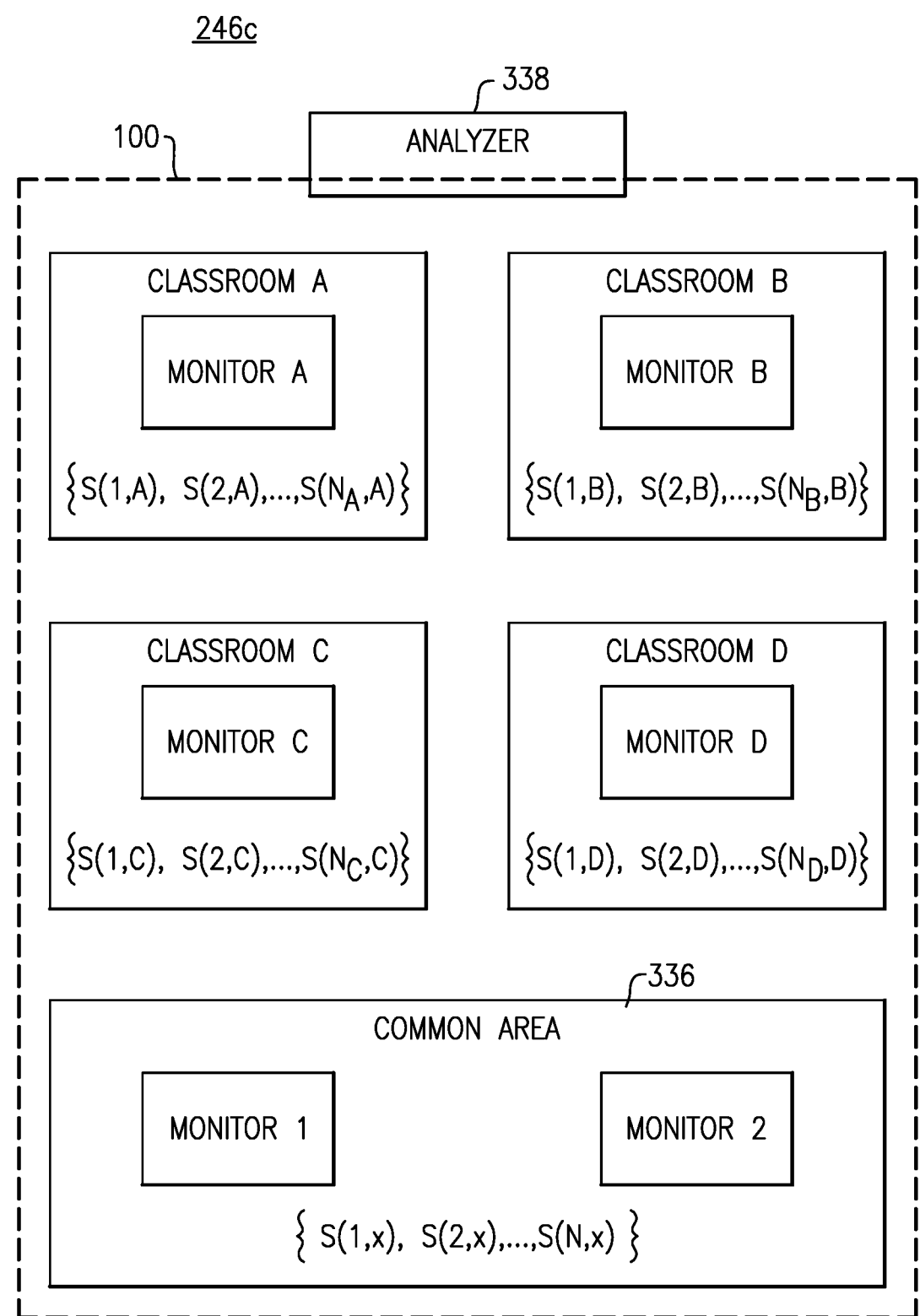
Figure 10:
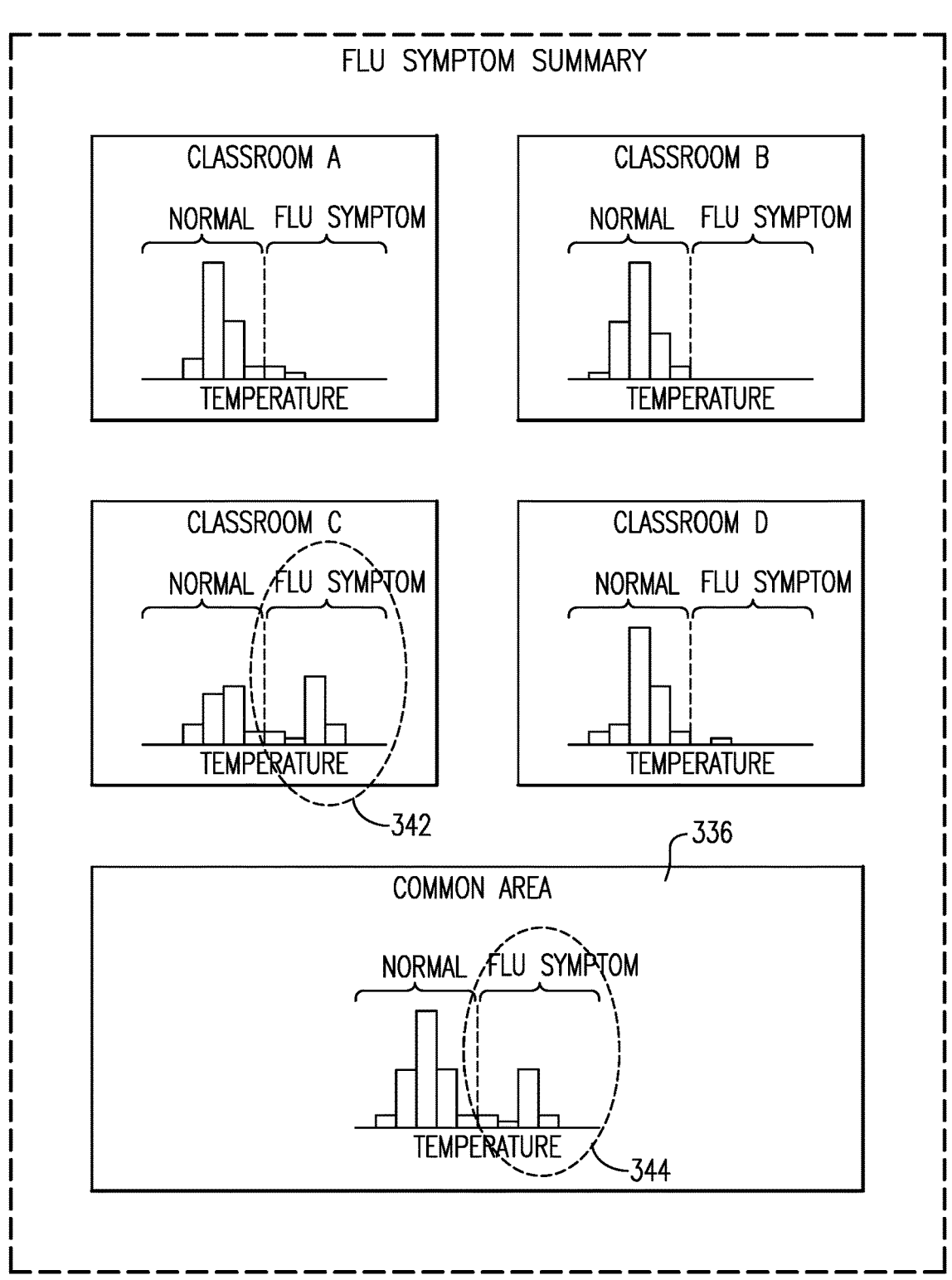
Figure 11A:
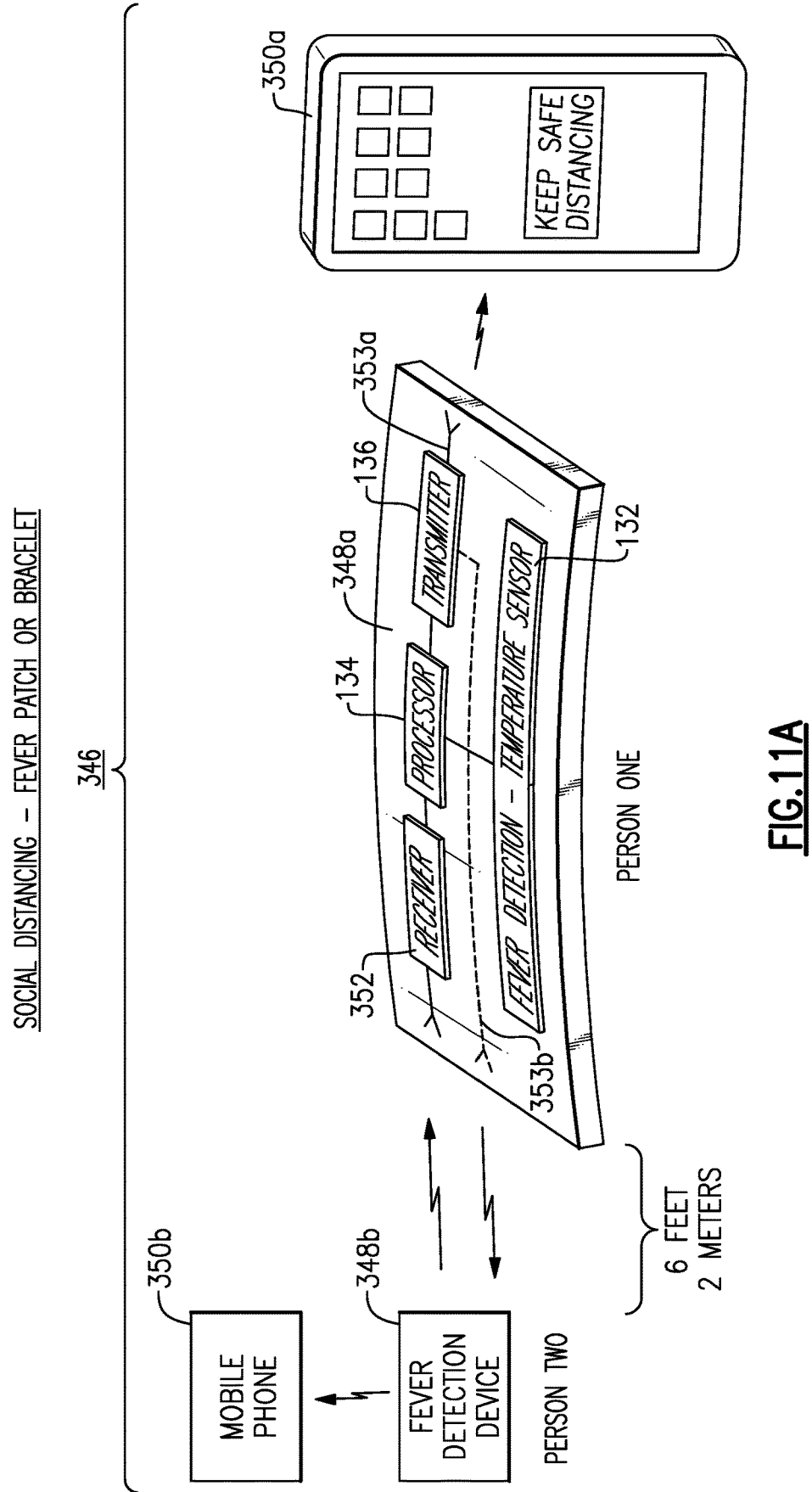
Figure 12A:
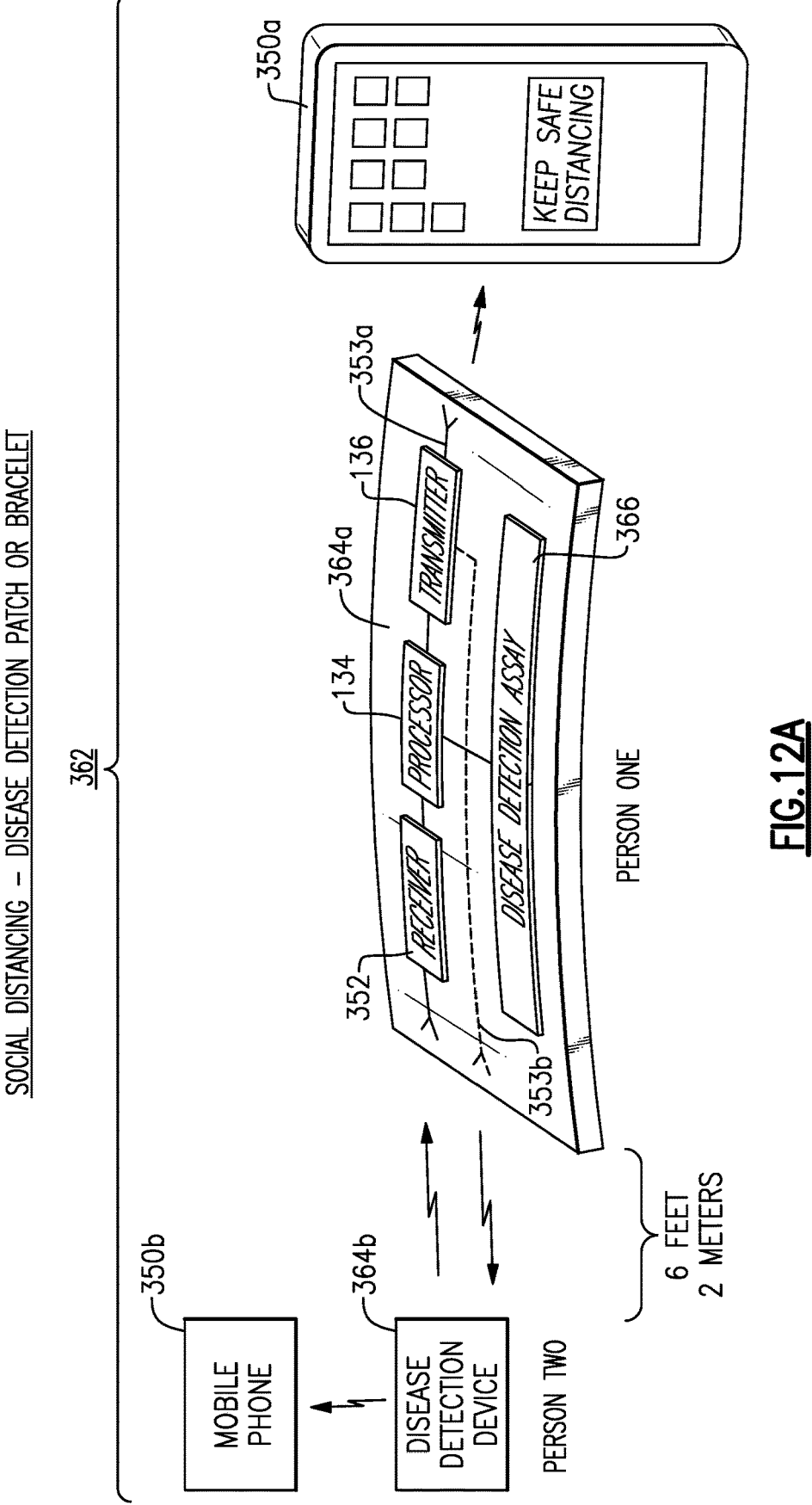
Figure 12B:
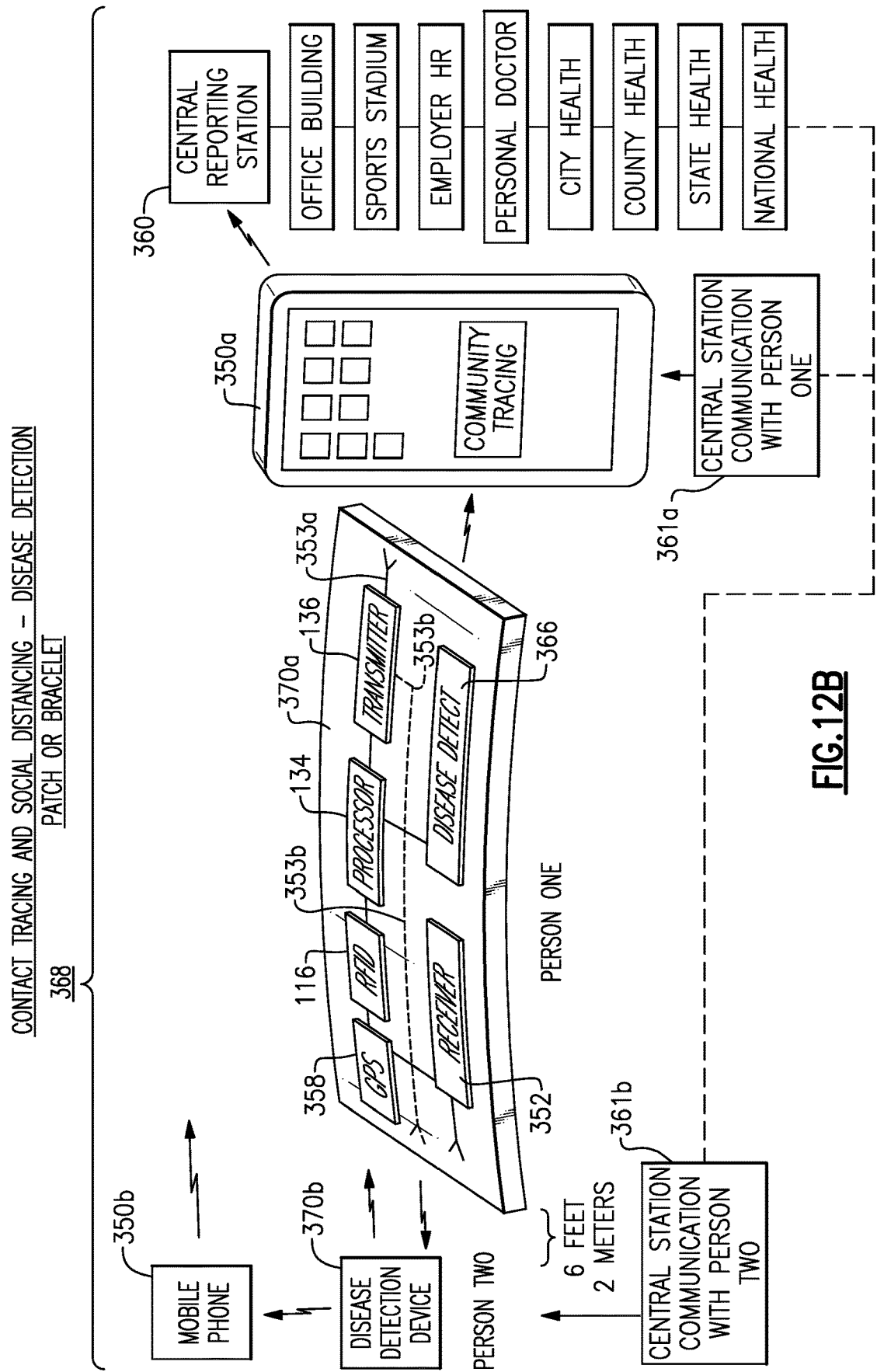
Figure 13A:
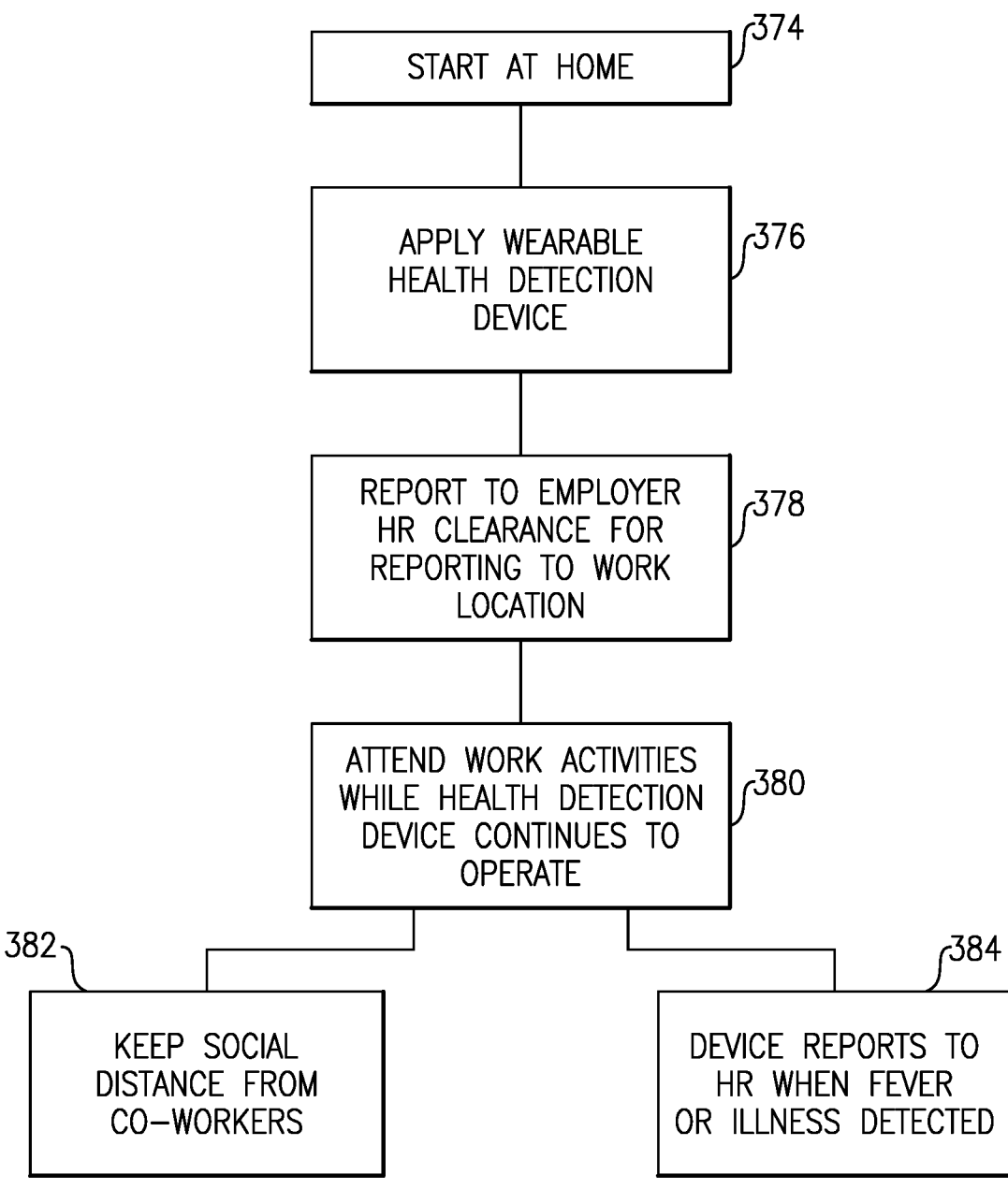
Figure 14A:
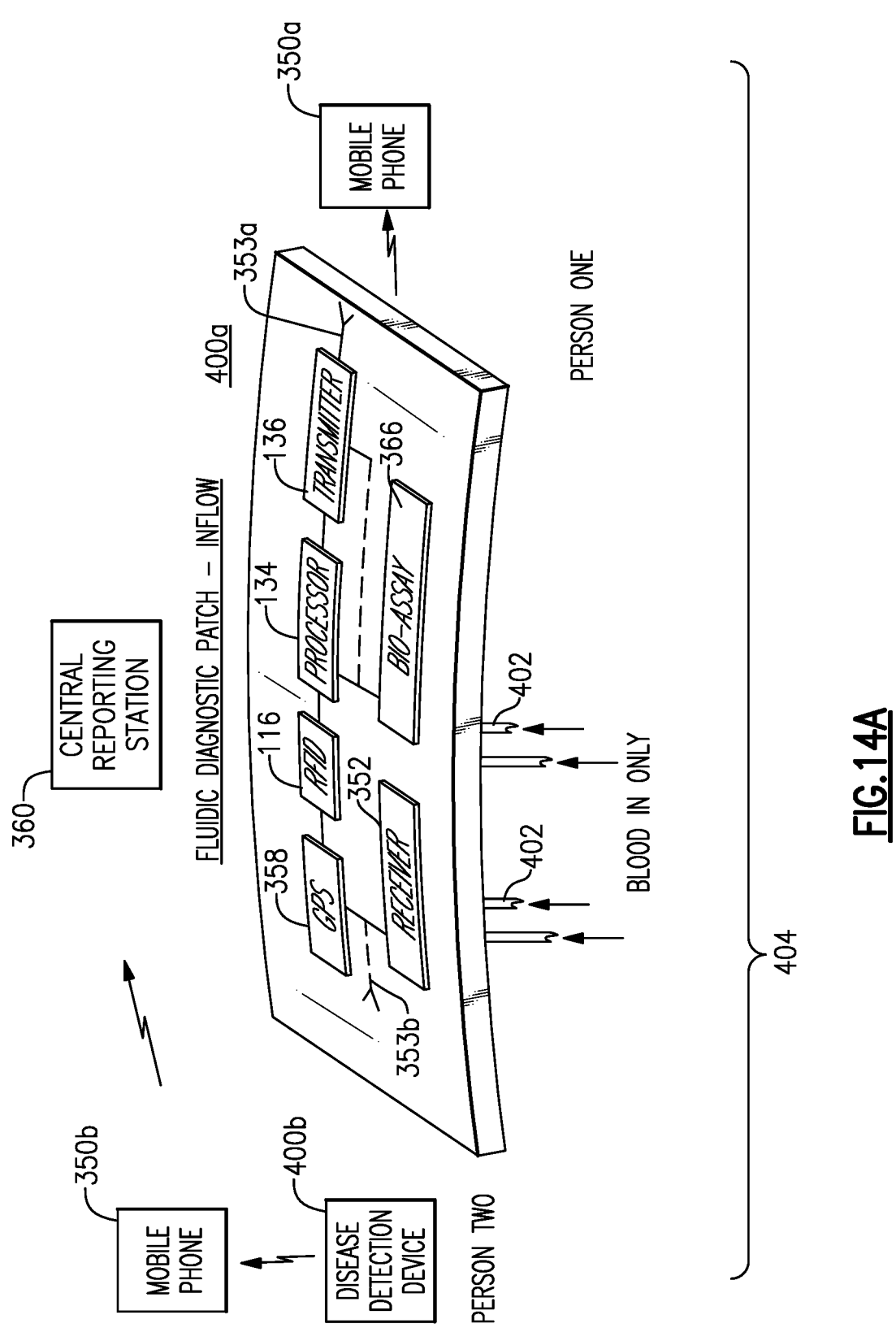
Figure 14B:
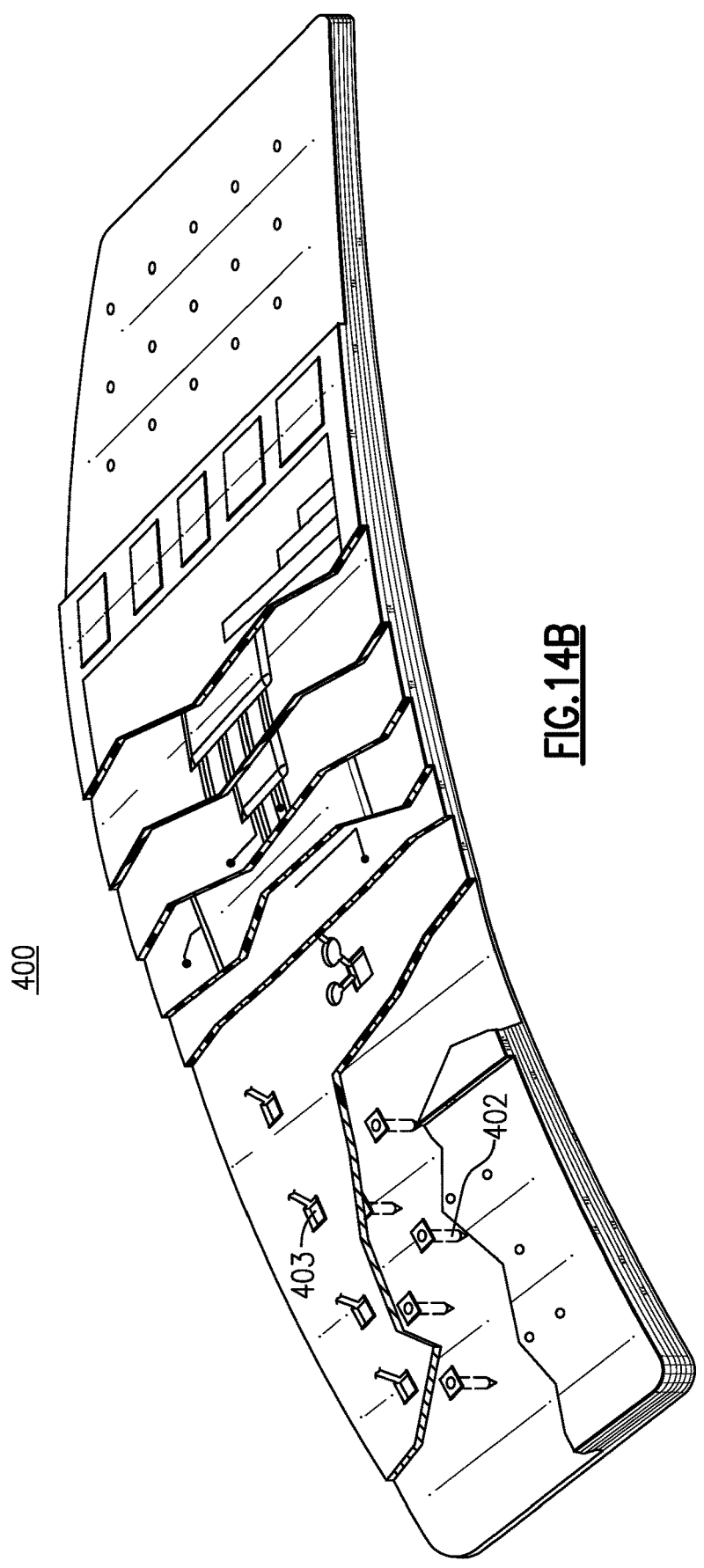
Figure 15A:
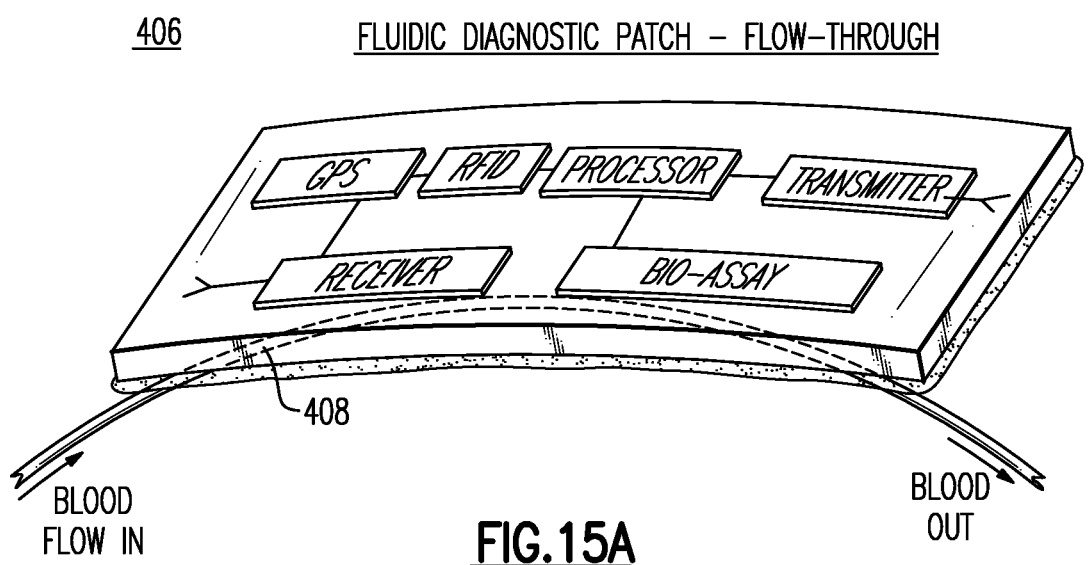
Figure 15B:
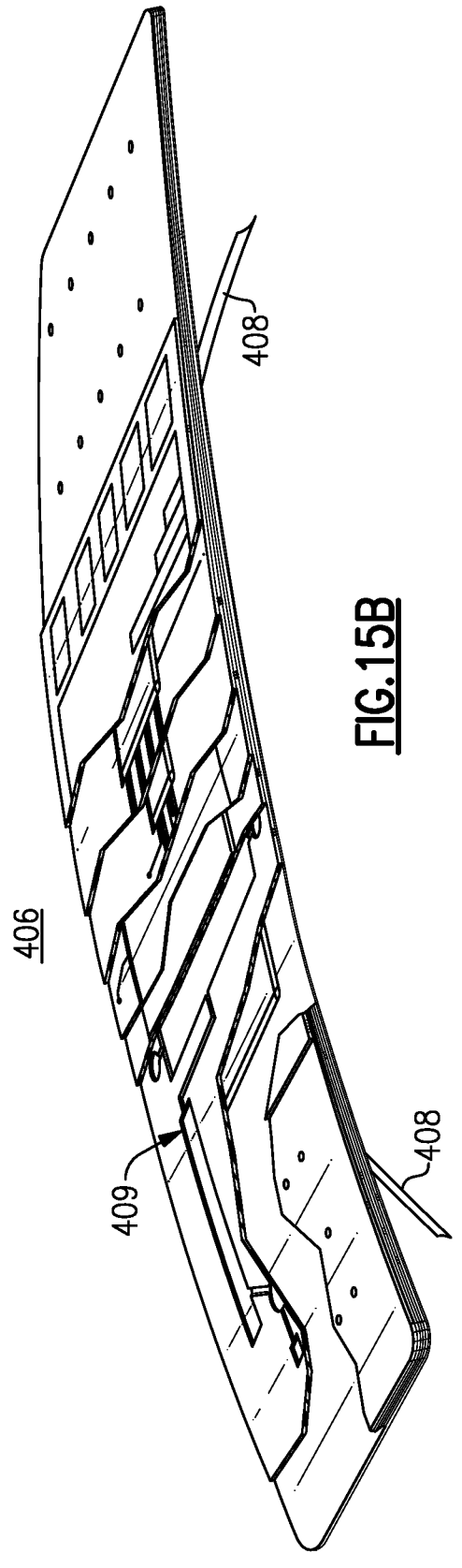
Figure 16A:
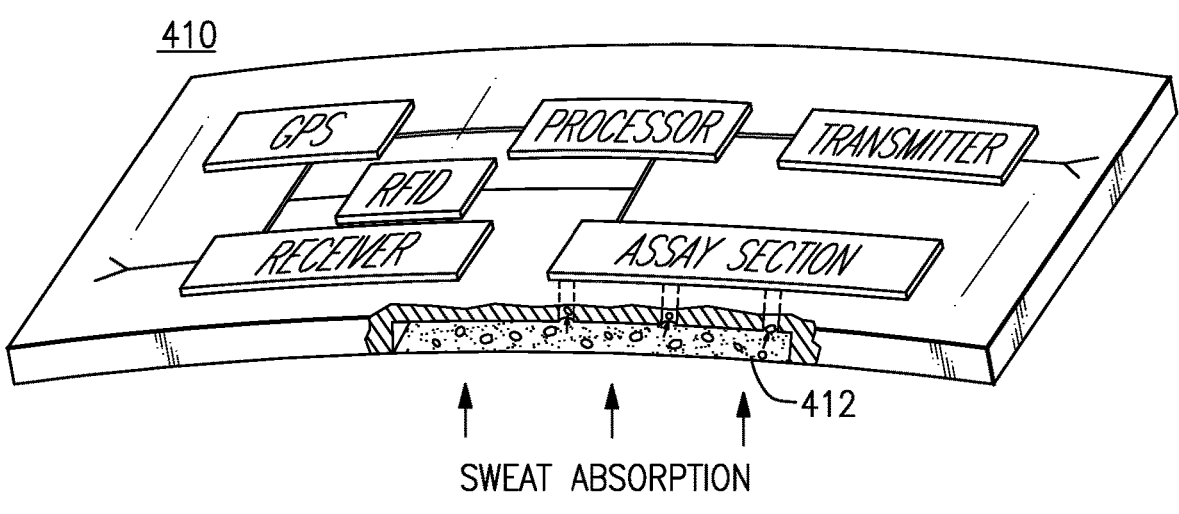
Figure 16B:
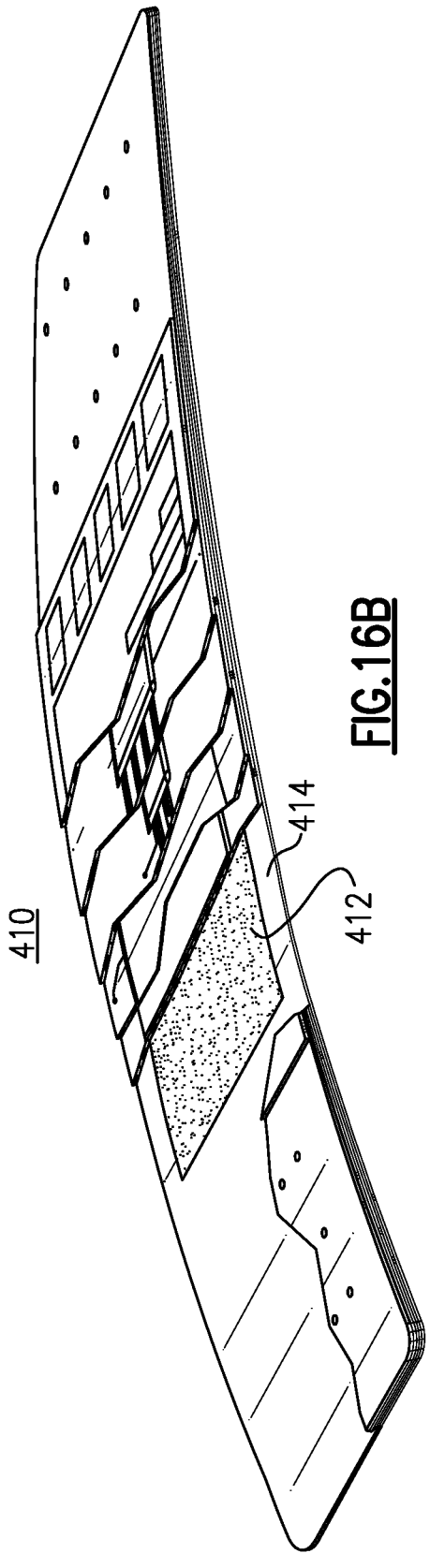
Figure 17A:
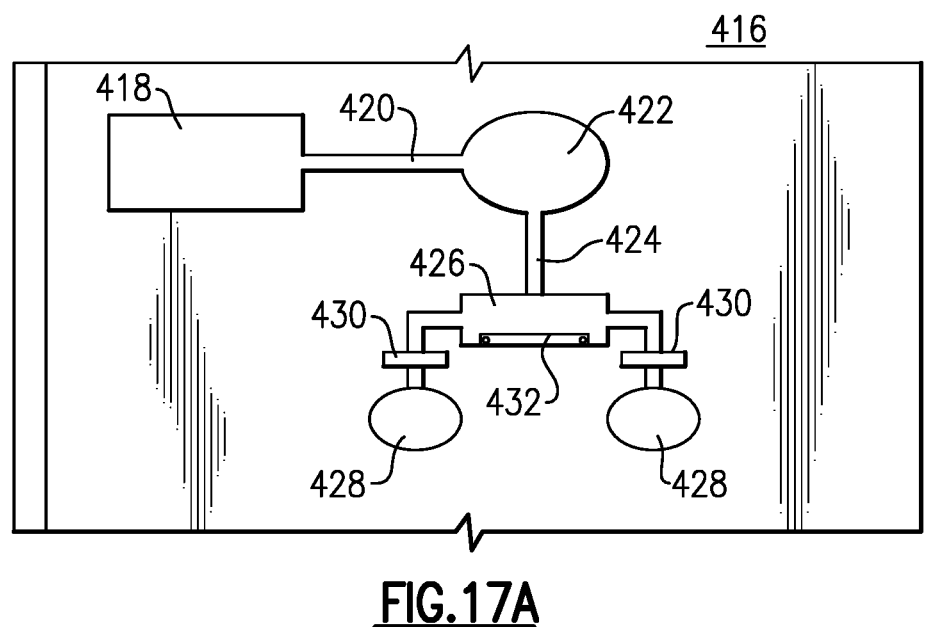
Figure 17B:
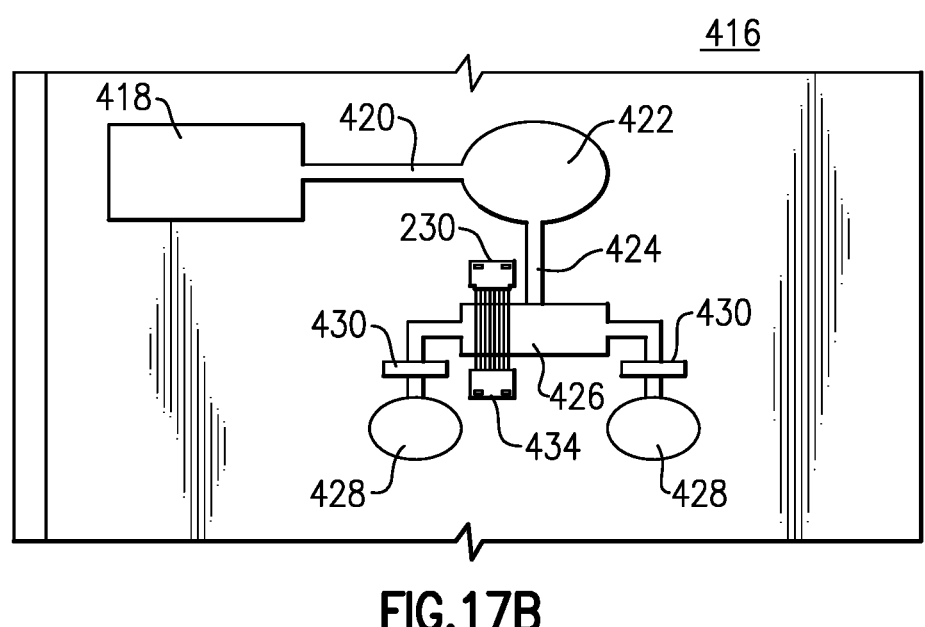
Figure 18:
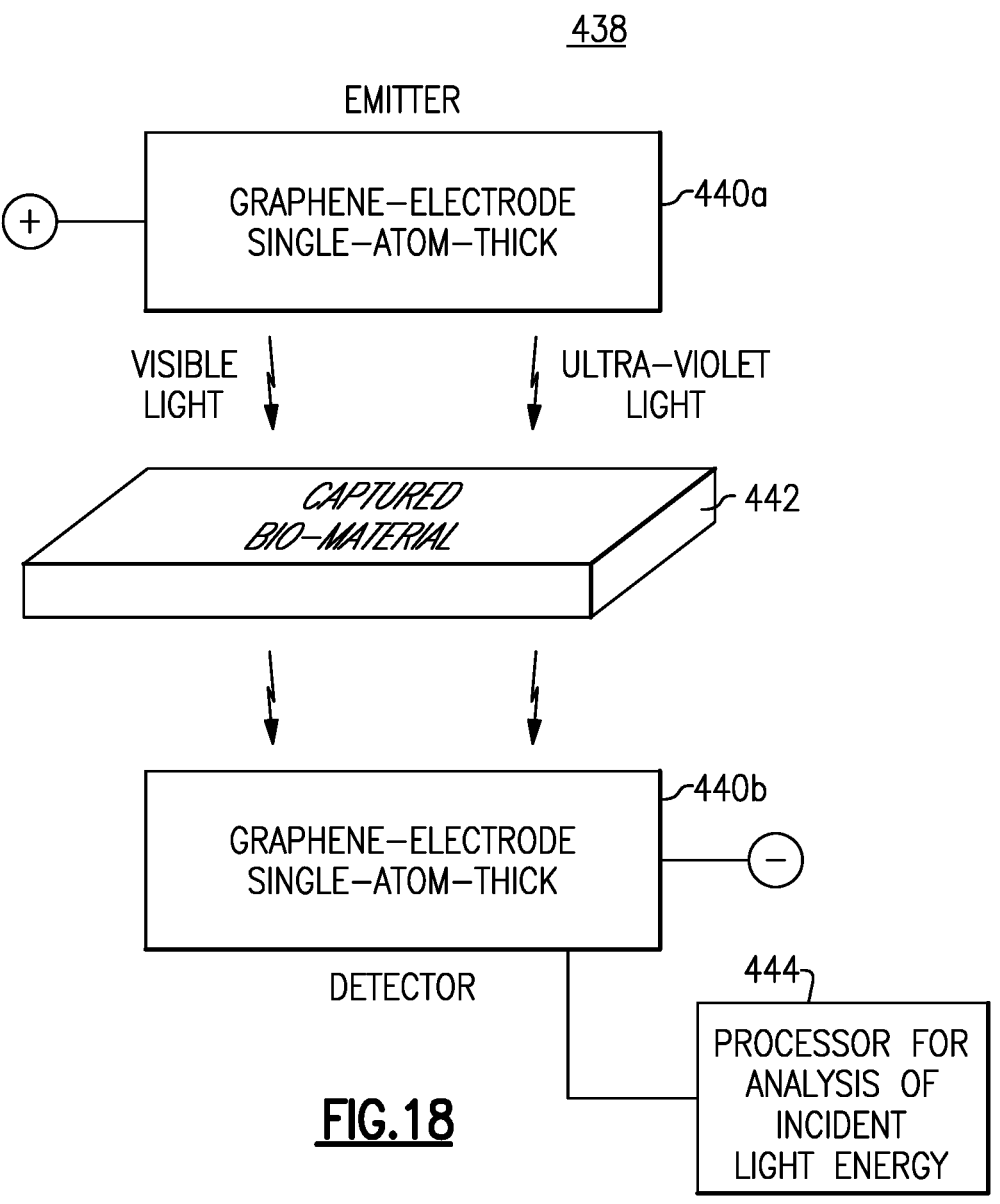
Figure 20A:
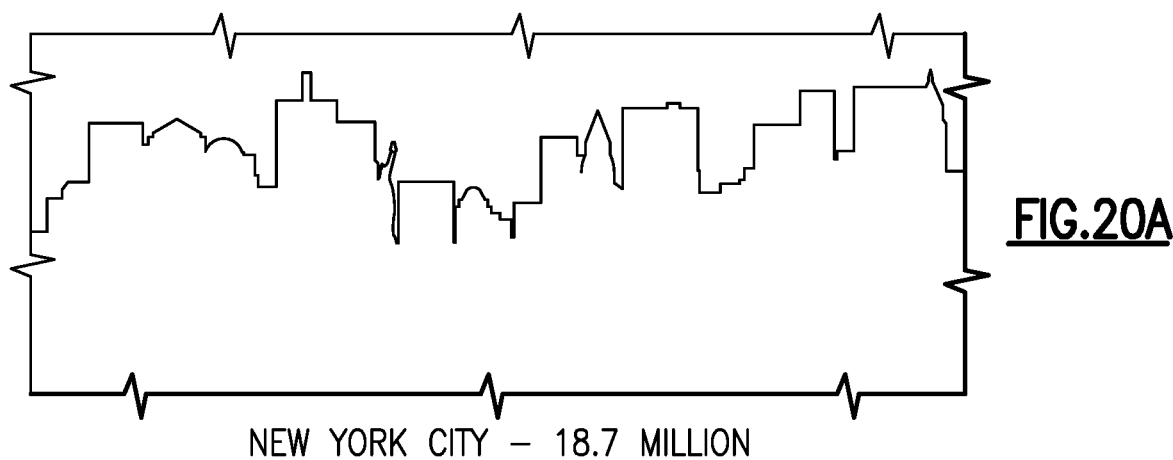
Figure 20B:
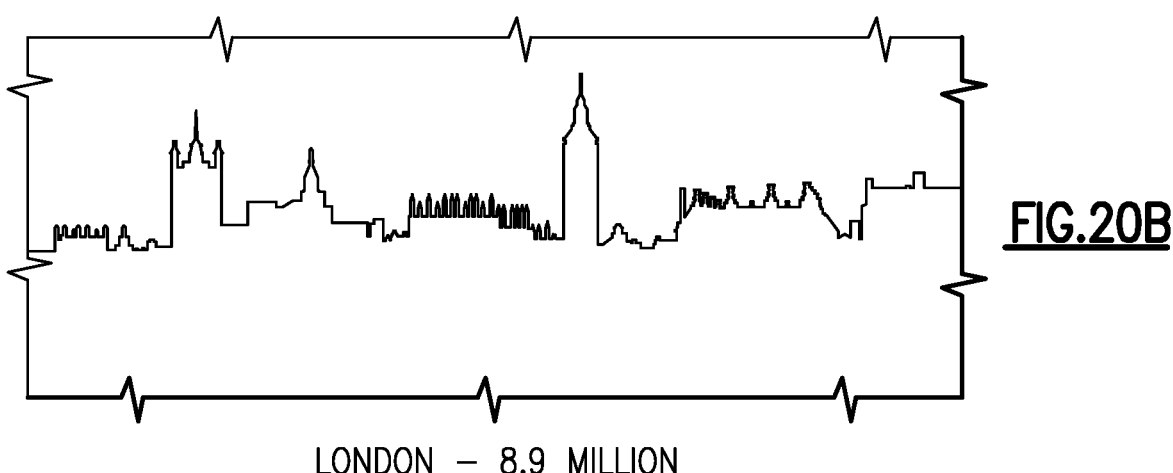
Figure 20C:
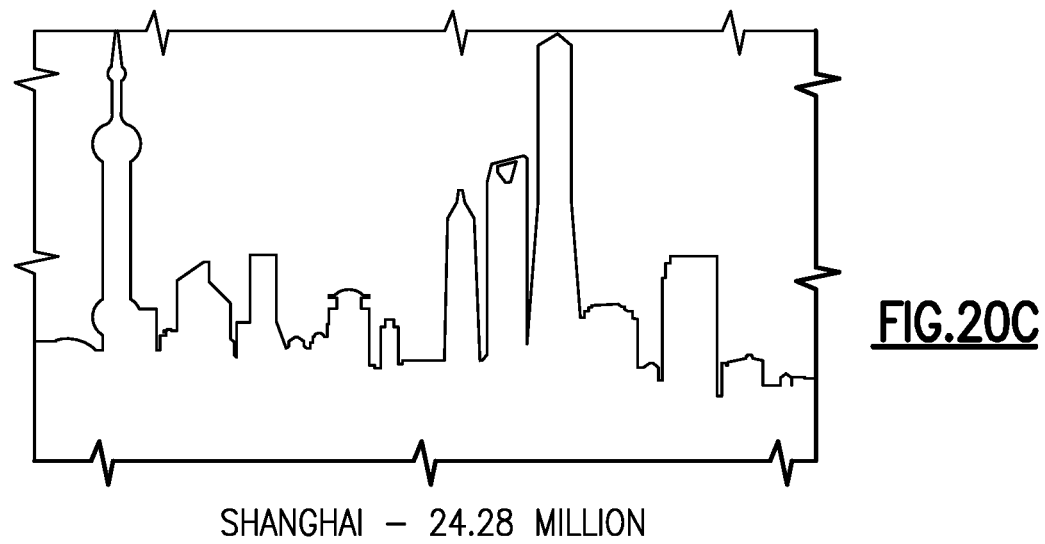
Figure 21:
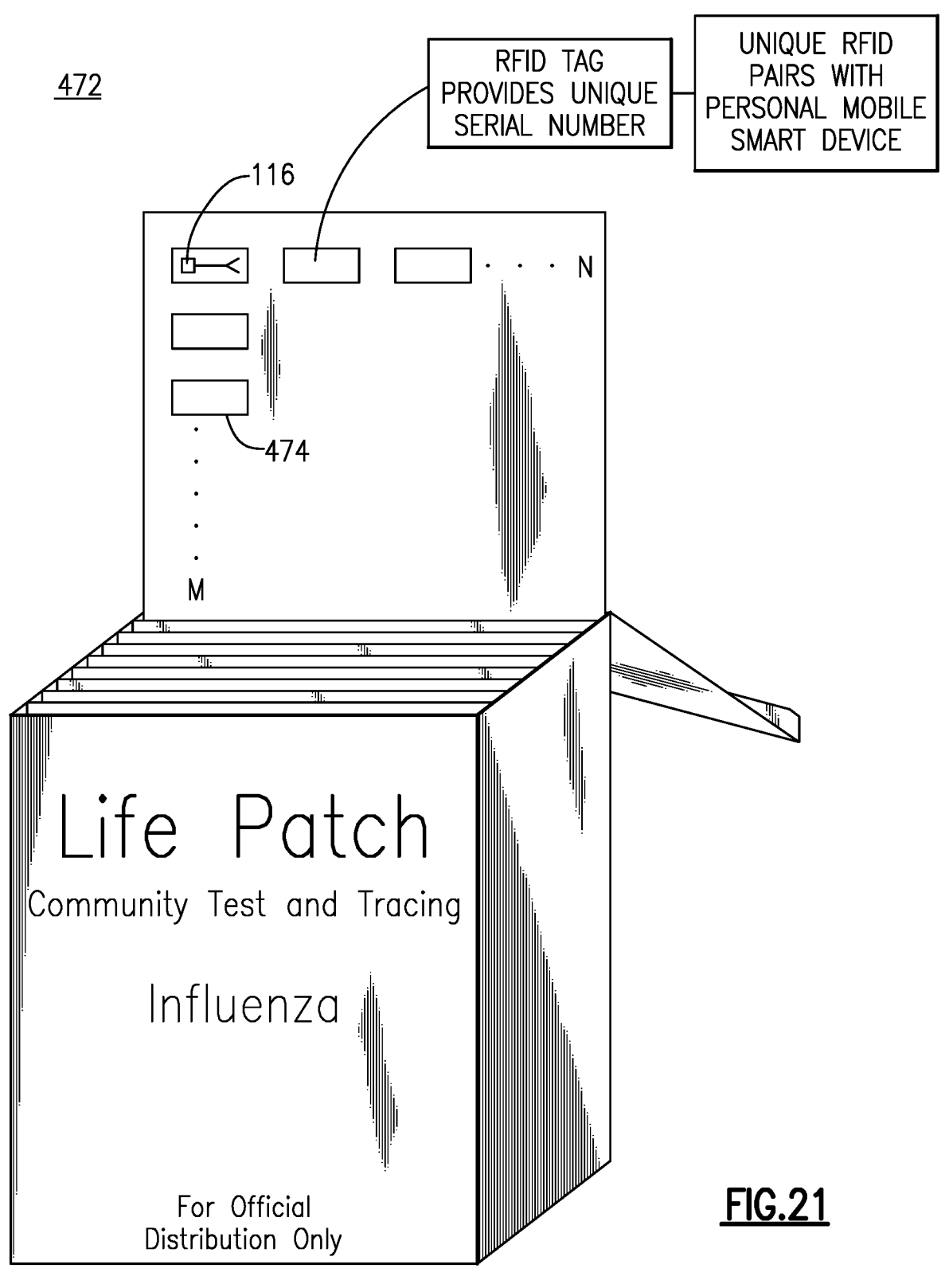
Figure 22A:
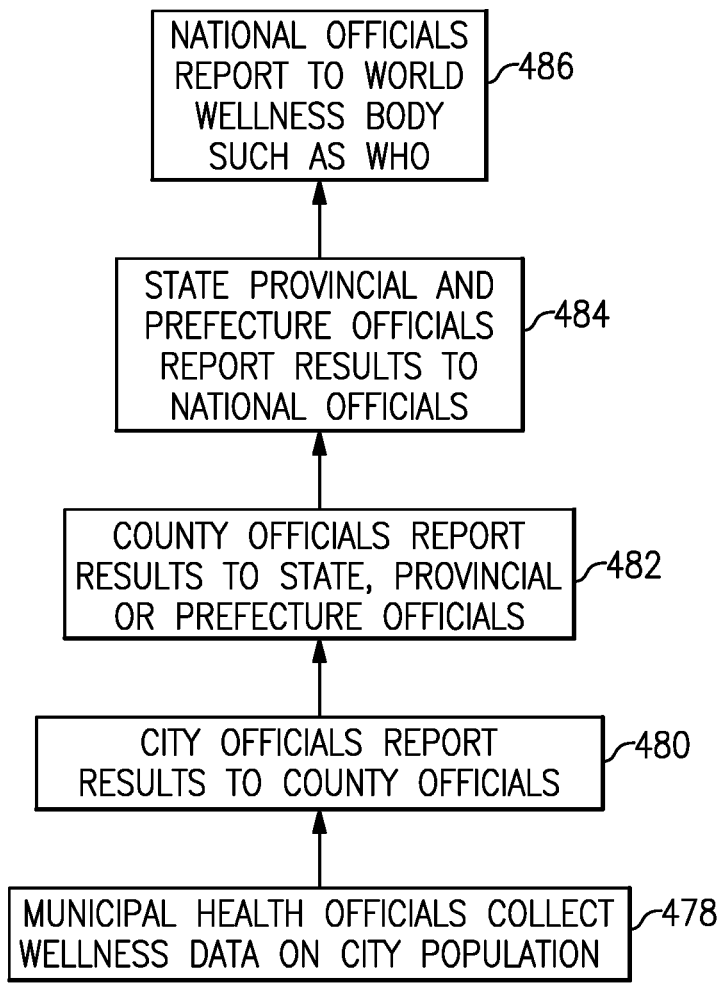
Figure 22B:
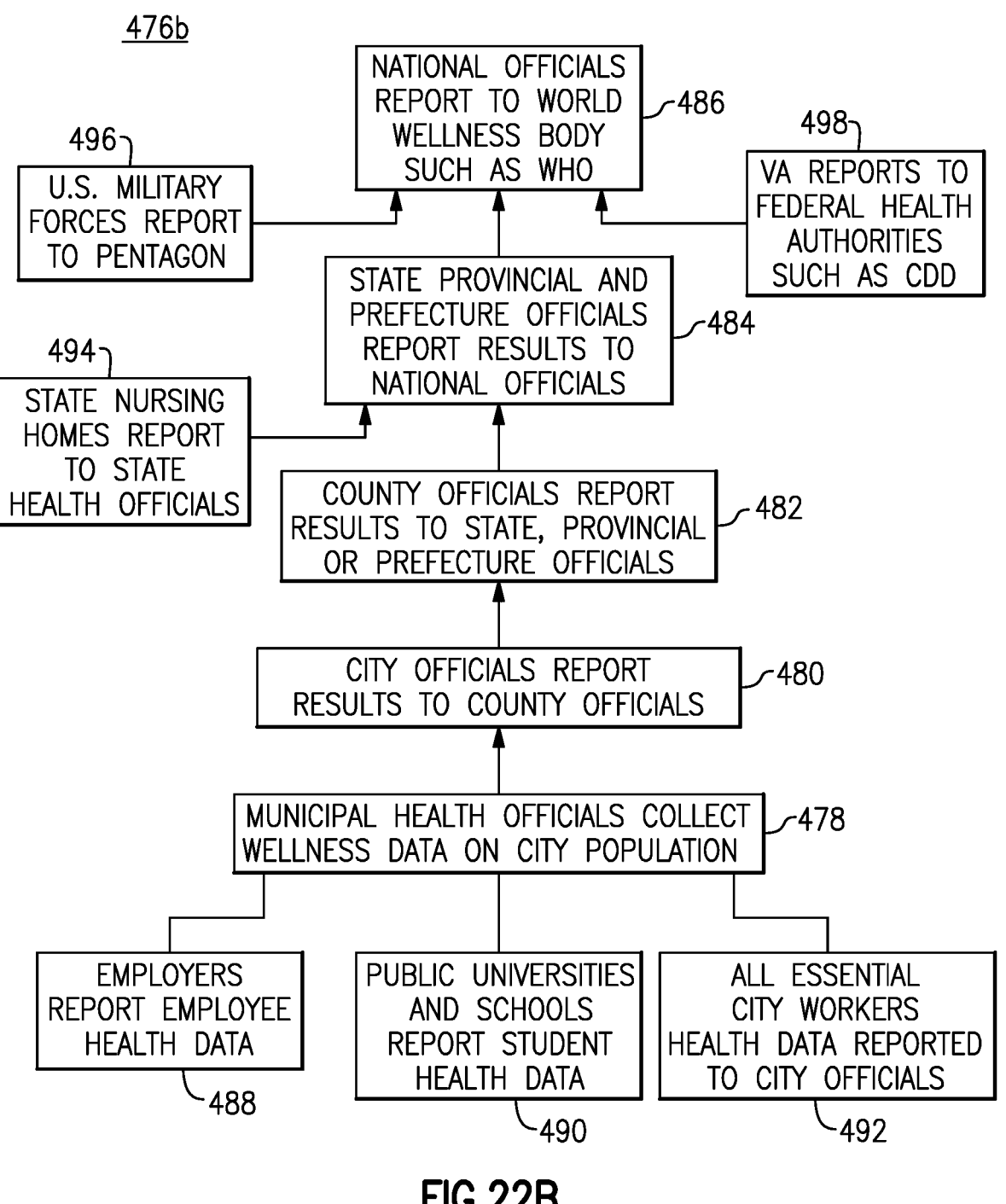
Figure 23A:
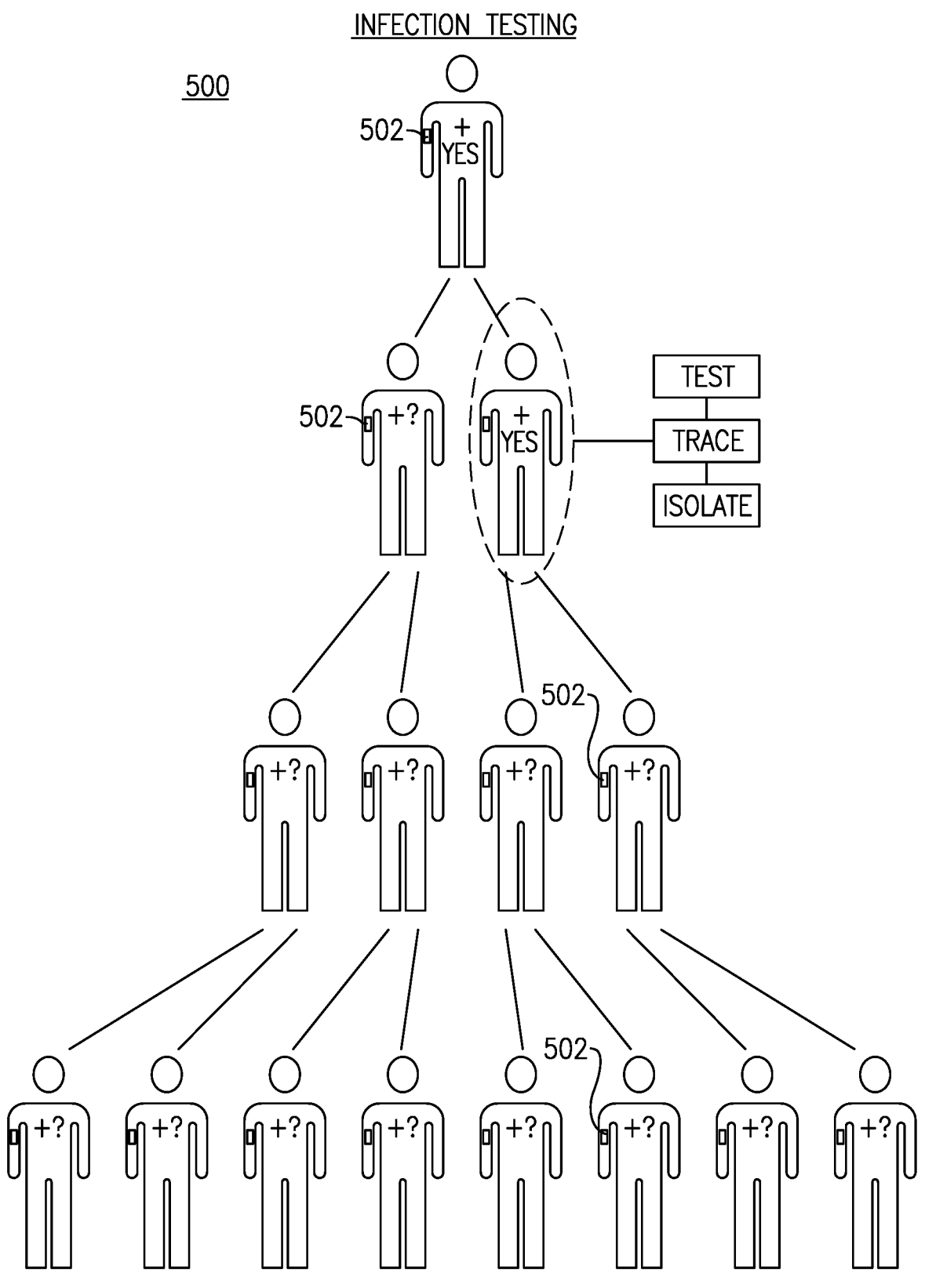
Figure 23B:
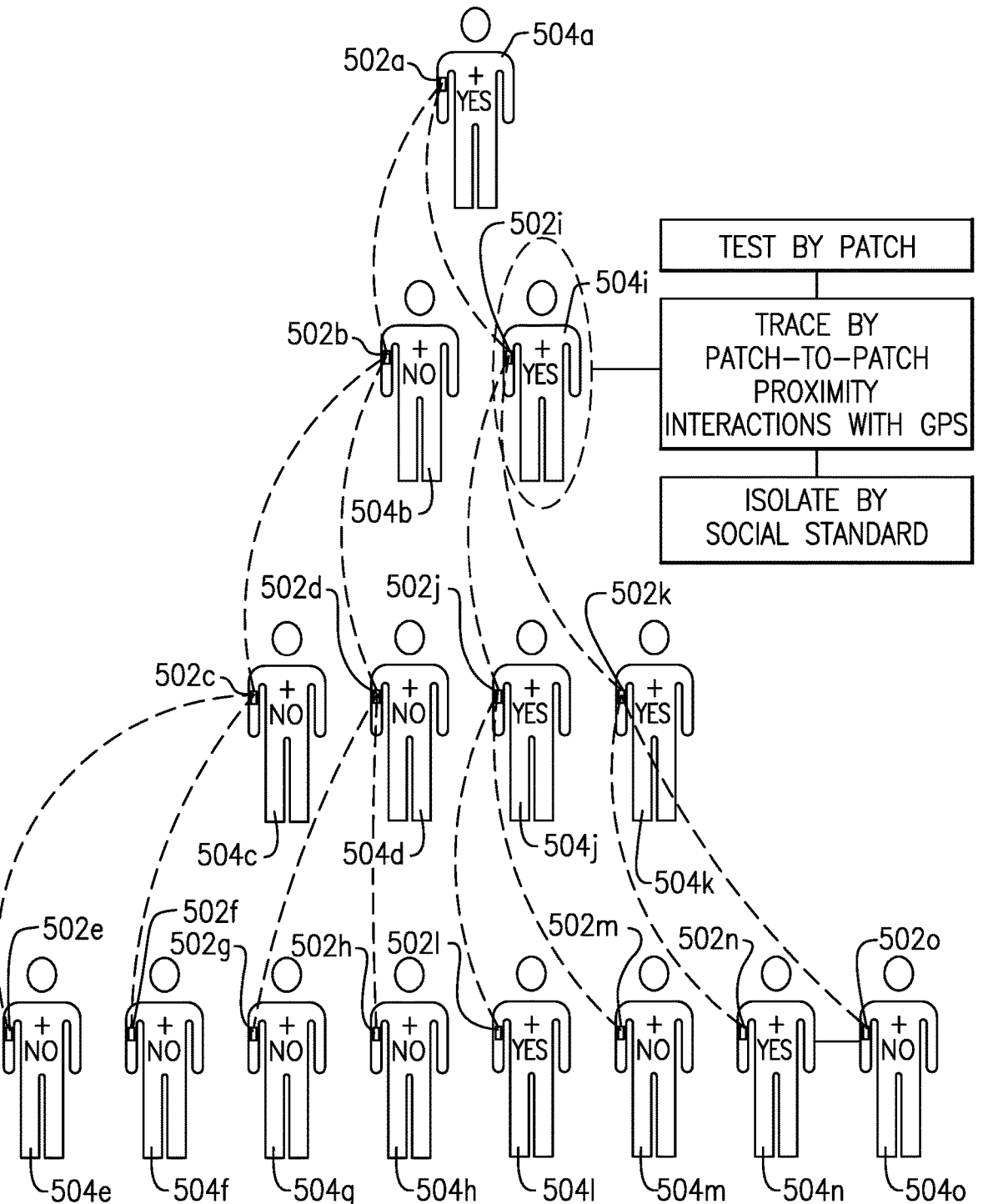
Figure 23C:
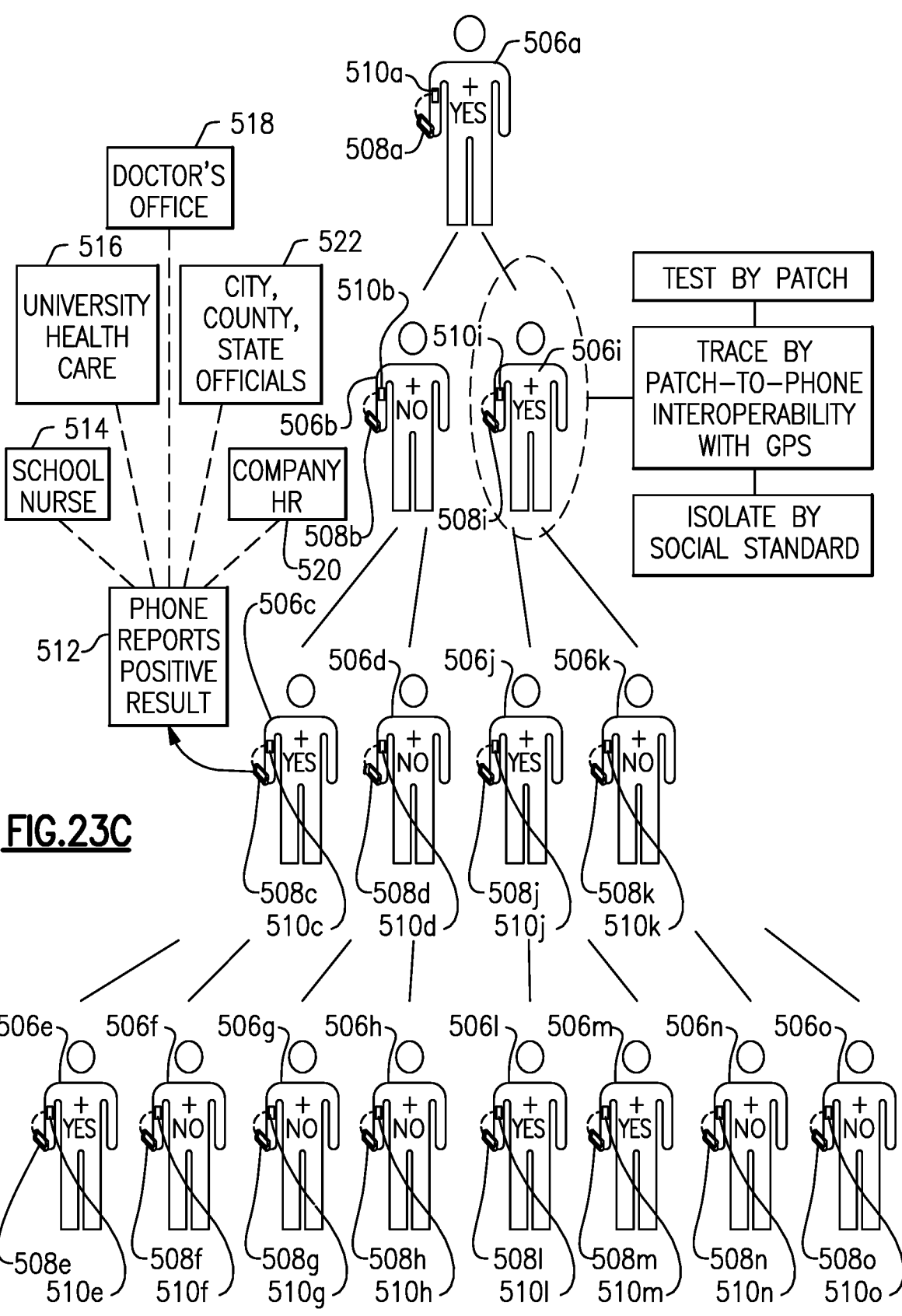
Figure 23D:
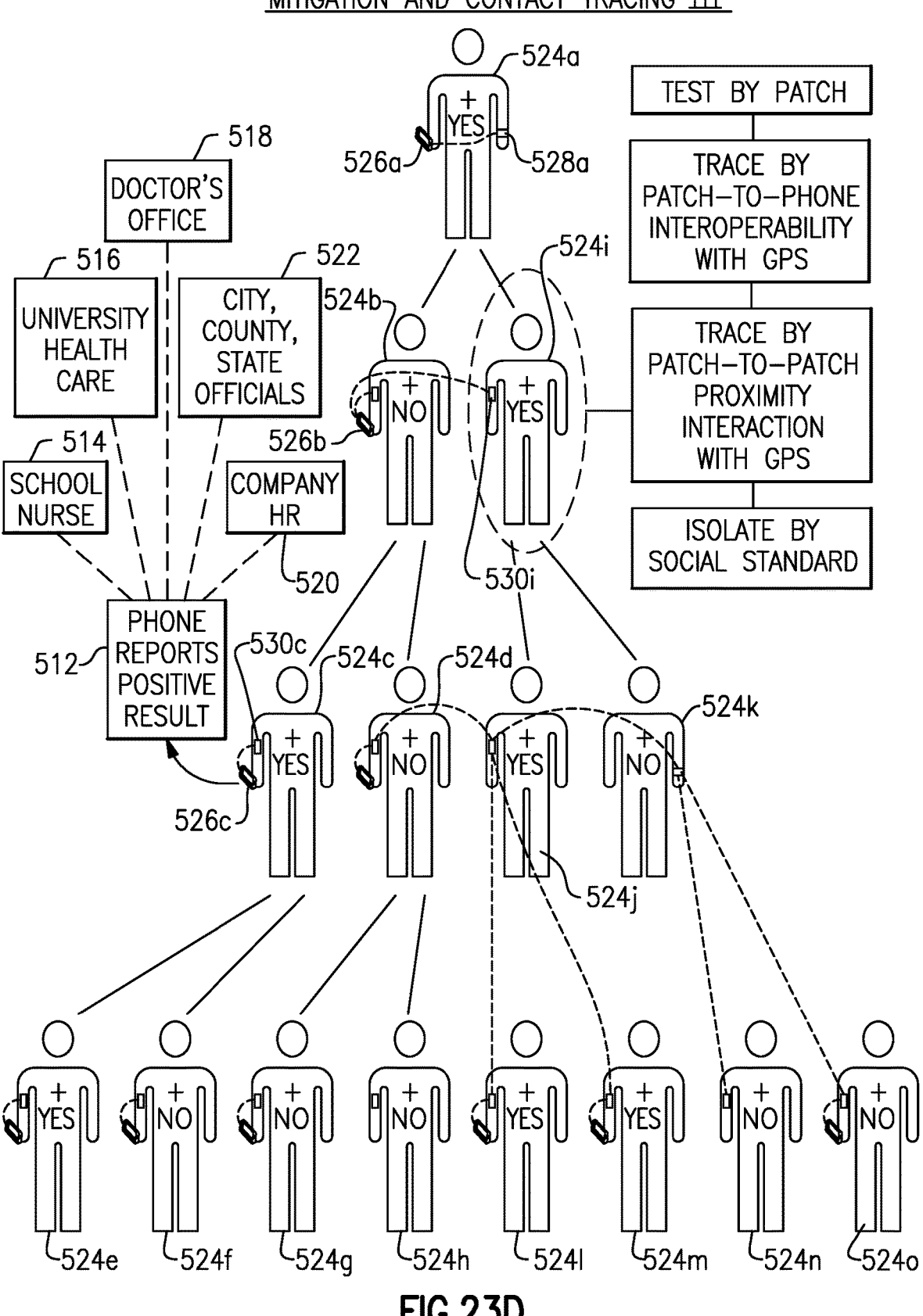
Figure 24:
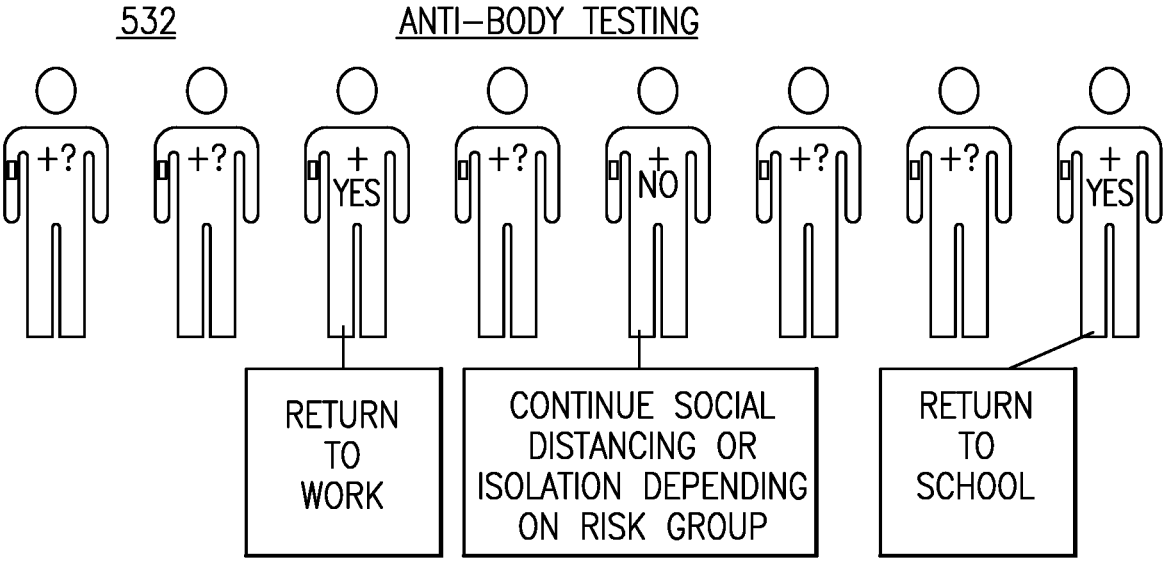
Figure 25A:
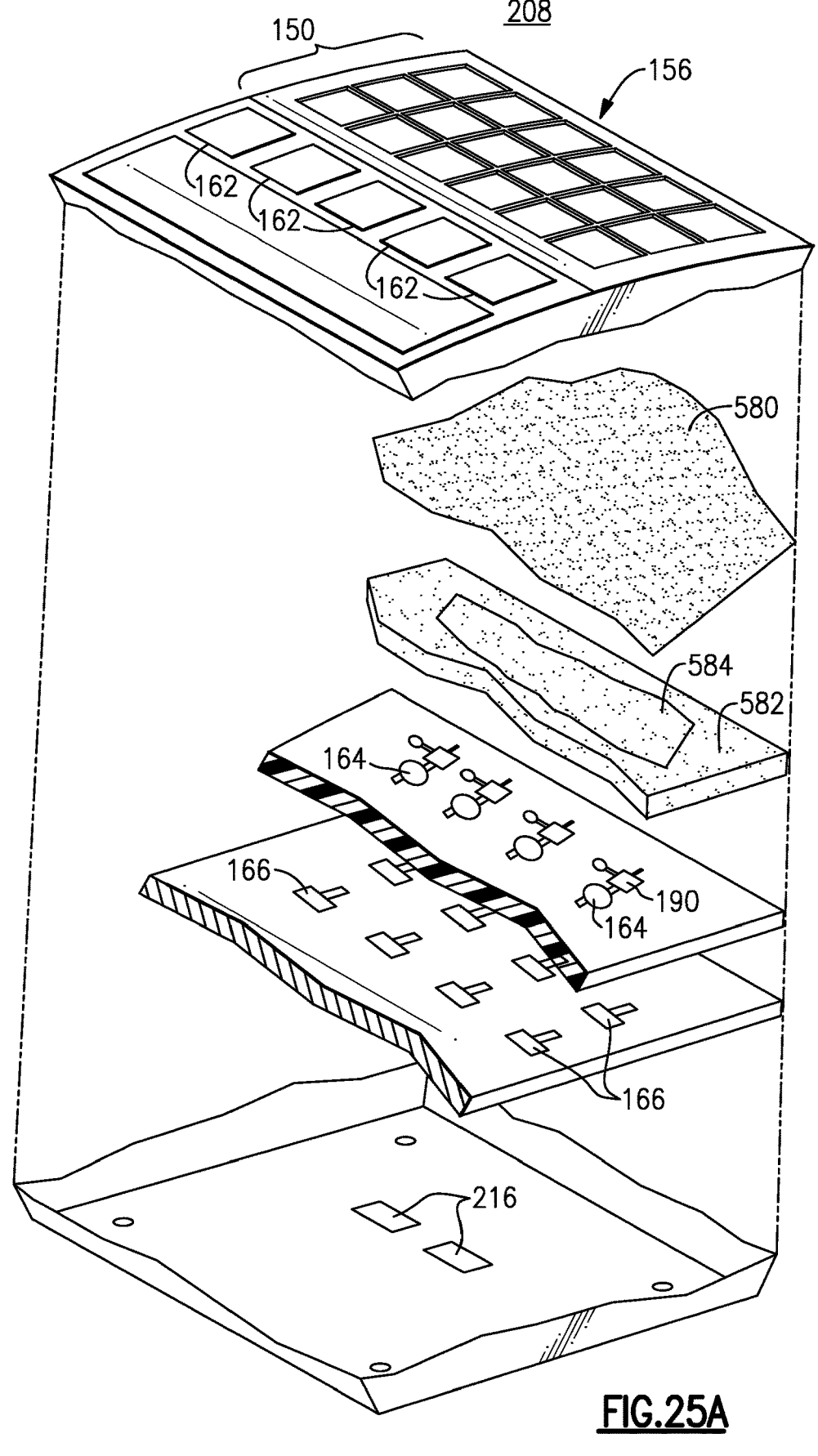
Figure 25B:
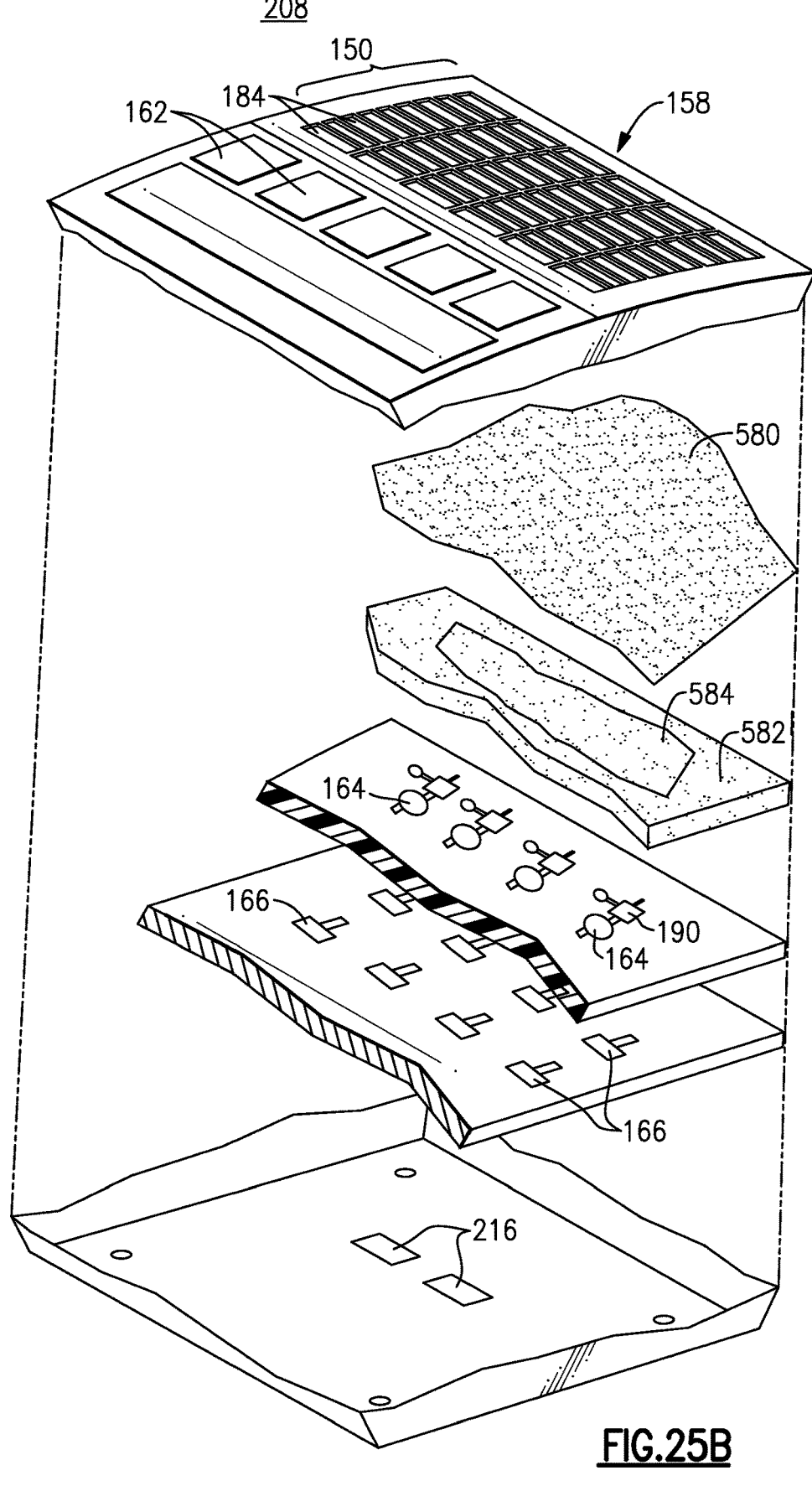
Figure 25C:
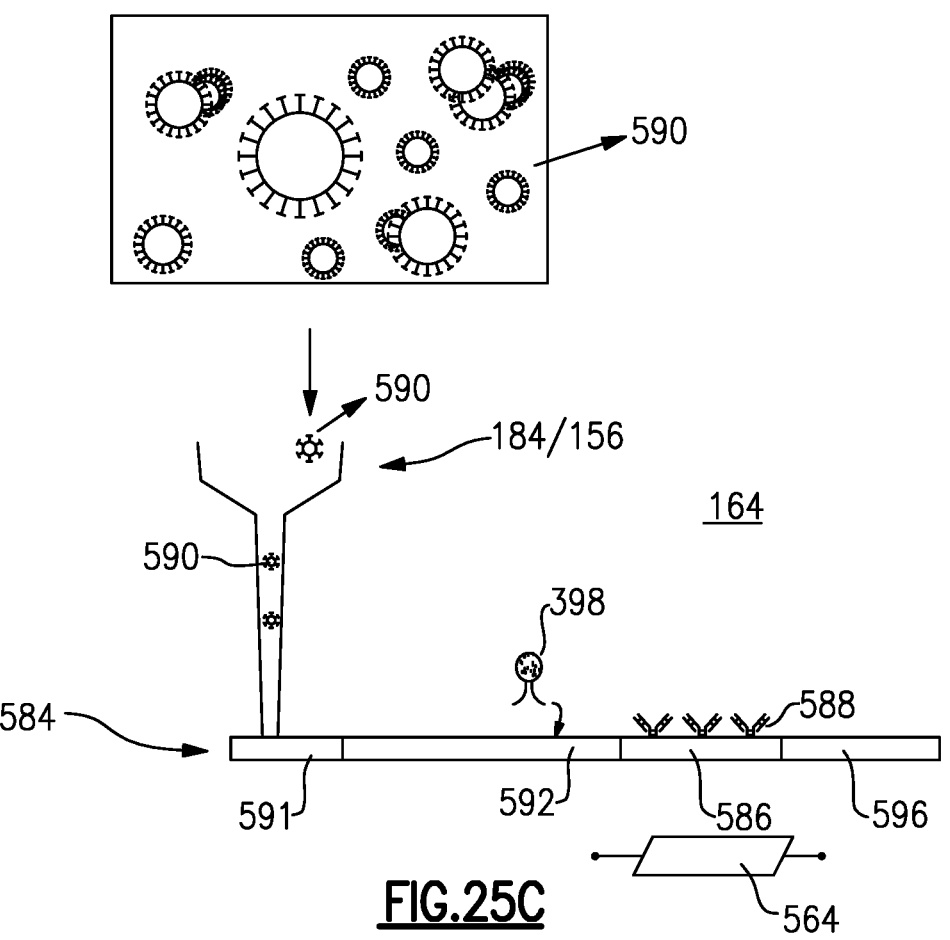
Figure 25D:
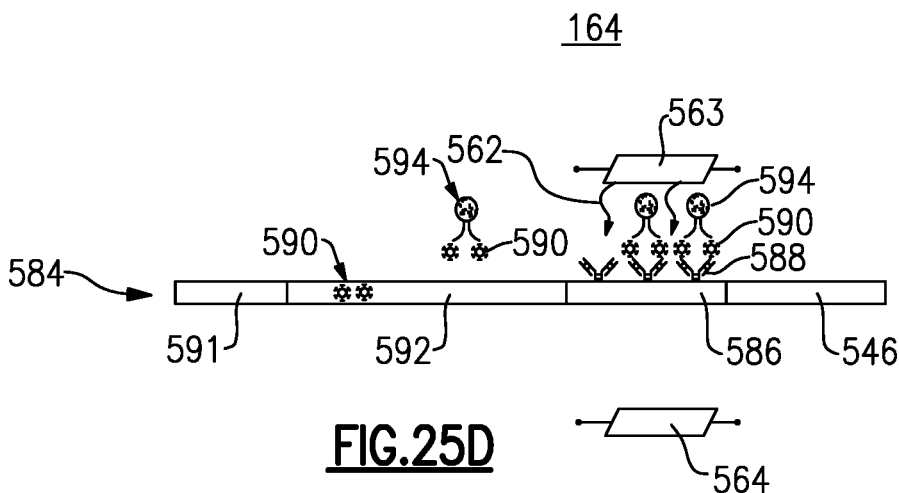
Figure 26:
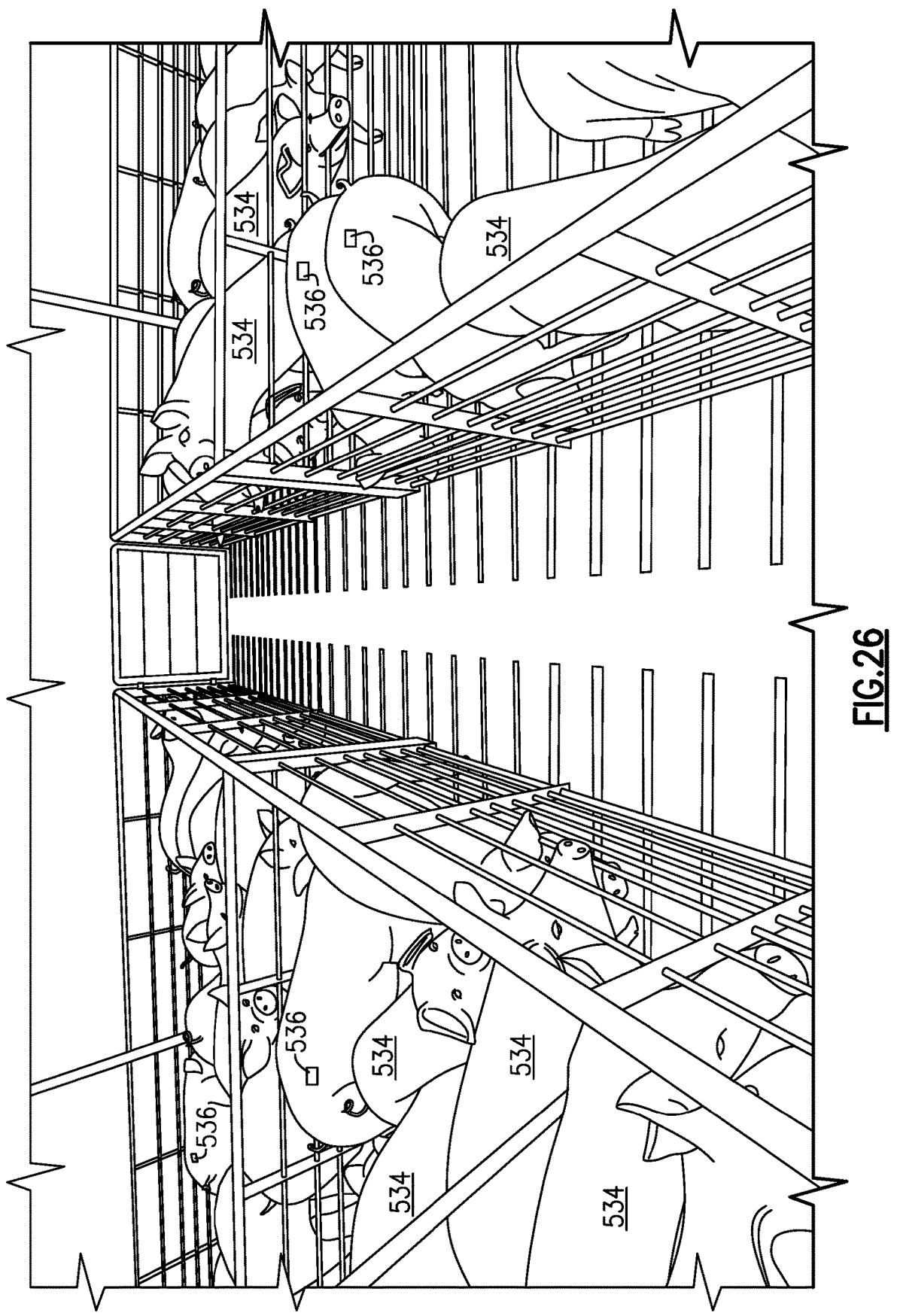

FIG. 2C presents some selected patch configurations that may be used to embody any of the patches hereof so as to promote social acceptance, community service, and personal pride associated with acting on behalf of the betterment of a populace group;

FIG. 3A is a perspective schematic view of a non-invasive patch device according to another particular embodiment hereof which includes a surface pad implemented to receive and identify a contagion by interaction with droplets from a sneeze or cough or otherwise deposited thereon by way of a finger wipe according to the teachings and implementations of various aspects of the present invention;

FIG. 3B is a perspective cut-away pictorial view of the disease detection patch device of FIG. 3A showing internal assemblies of micro-fluidic circuits, assay results detectors, and electronic signal processing components according to the teaching hereof;

FIGS. 3C and 3D illustrate use of the patch device of FIG. 3B when applied in the crook of the elbow to catch water droplets from a cough or sneeze according to certain aspects of the present inventions disclosed herein;

FIG. 3E is a block diagram showing the principal steps of one preferred method of using the patch device of FIG. 3B;

FIG. 3F-1 is a perspective cut-away pictorial view of an alternate embodiment of the patch device of FIG. 3B having a cough or sneeze pad for on-body use similarly showing the internal assemblies for micro-fluidics, assay results, and electronic signal processing according to the teachings hereof;

FIG. 3F-2 is a perspective cut-away pictorial view of an alternate embodiment of the patch device of FIG. 3B having a finger-wipe pad for on-body or off-body use similarly showing the internal assemblies for micro-fluidics, assay results, and electronic signal processing according to the teachings hereof;

FIG. 3G illustrates an on-body application of the finger-wipe patch device of FIG. 3F-2;

FIG. 3H shows one example of an off-body application of the finger-wipe patch device of FIG. 3F-2 according to additional personalized wellness aspects of the present invention wherein the patch is applied in a discrete manner to a student's notebook for use during the school day that may be maintained out-of-view of classmates;

FIG. 3I is a block diagram presenting an initial step of one preferred method of using the finger-wipe patch device of FIG. 3F-2;

FIG. 3J is a perspective pictorial view illustrating use of the finger-wipe pad of the patch device of FIG. 3F-2;

FIG. 3K is a block diagram showing the principal steps of one preferred method of using the patch device of FIG. 3F-2;

FIG. 4A is a perspective schematic view of a non-invasive bracelet device according to yet another particular embodiment hereof which includes an alternate implementation of surface pad functionalities discussed in conjunction with FIGS. 3A to 3E;

FIG. 4B is another perspective schematic view of the non-invasive bracelet device of FIG. 4A illustrating replacement of a removable assay cartridge according to a certain aspect of the inventions hereof as relating thereto;

FIG. 4C-1 is a perspective pictorial view of a cartridge holder and replaceable assay cartridges each with a sneeze or cough pad and a finger-wipe pad for use in a personal wellness bracelet of the type illustrated in FIG. 4B;

FIG. 4C-2 is a view similar to FIG. 4C-1 presenting an alternate embodiment of the replaceable assay cartridges for use in a personal wellness bracelet of the type illustrated in FIG. 4B showing each cartridge thereof including only a finger-wipe pad for collecting biological material according to certain sample collection aspects of the inventions hereof;

FIG. 4D is a block diagram showing the principal steps of certain preferred methods of using the bracelet device of FIG. 4B with either of the assay cartridges from FIGS. 4C-1 and 4C-2;

FIG. 4E-1 is a perspective schematic view of a non-invasive fever-detection bracelet according to yet another particular embodiment hereof which includes an alternate implementation of the temperature sensing functionalities discussed in conjunction with FIG. 2A;

FIG. 4E-2 is a perspective schematic view of an alternate embodiment of the non-invasive fever-detection bracelet of FIG. 4E-1 further including a display monitor for posting a fever indicator viewable by the bracelet user;

FIG. 5 is an example where a patch worn by a child communicates with a monitor through a communication link that includes one or more intermediate devices;

FIG. 6A is an example where a plurality of children with respective patches are monitored by a monitor;

FIG. 6B is an example where a plurality of patches communicate with each other, with an external device, or some combination thereof;

FIG. 7A is a block diagram presenting the principal steps of a mandatory use case scenario of the devices disclosed herein that may be deployed by health officials during the outbreak of a serious life-threatening pandemic to control the spread thereof in the interests of saving lives;

FIG. 7B is a block diagram presenting the principal steps of another mandatory use case scenario wherein use and reporting is confined between parent and child to promote wellness in a social group;

FIG. 8A-1 is a block diagram presenting the principal steps of a voluntary use case scenario of the patch devices disclosed herein that may be deployed by parents and students to detect fever during flu season to promote the health and wellness of individuals and community groups;

FIG. 8A-2 is a block diagram presenting the principal steps of a voluntary use case scenario of the bracelet devices disclosed herein that may be deployed by parents and students to detect fever during flu season to promote the health and wellness of individuals and community groups;

FIG. 8A-3 is a block diagram presenting the principal steps of a voluntary use case scenario of a bracelet device disclosed herein that may be deployed by parents and students to detect fever in the student where the bracelet communicates automatically over long-range with the parent or other guardian;

FIG. 8B is a block diagram presenting the principal steps of a voluntary use case scenario of the patch and bracelet devices disclosed herein having a cough pad, a sneeze pad, or a finger-wipe pad according to certain embodiments of the present inventions as may be deployed by parents with their children during a serious epidemic or as otherwise desired;

FIG. 8C-1 is a block diagram presenting the principal steps of a voluntary use case scenario relating to promoting class attendance for university students;

FIG. 8C-2 is a block diagram of the principal system elements related to performing the steps of the methods discussed in conjunction with FIG. 8C-1;

FIG. 9 is an example where a system according to the present invention is implemented for utilization in a gathering institution such as a school or university;

FIG. 10 is an example of a flu symptom summary that can be generated by the system of FIG. 9;

FIG. 11A is a diagrammatic pictorial view of a two-device fever detection system implemented for maintaining social distancing according to the present invention;

FIG. 11B is a diagrammatic pictorial view of a two-device fever detection system implemented for maintaining social distancing and conducting contact tracing in accordance with principal aspects of the inventions illustrated therein;

FIG. 12A is a diagrammatic pictorial view of a two-device disease detection system implemented for maintaining social distancing according to additional aspects of this invention;

FIG. 12B is a diagrammatic pictorial view of a two-device disease detection system implemented for maintaining social distancing and conducting contact tracing in accordance with principal aspects of the inventions illustrated therein;

FIG. 13A is a flow diagram of a method of self-testing and reporting for a member of a working population using a wearable health detection device according to the present invention;

FIG. 13B is a flow diagram of a method of self-testing and reporting for a member of a student population using a wearable health detection device according to the present invention;

FIG. 14A is a perspective schematic view of a fluidic patch device according to a particular embodiment hereof which includes micro needles to draw a blood sample into the patch for diagnostic testing according to certain fluid-flow embodiments of the present inventions;

FIG. 14B is a perspective cut-away pictorial view of the patch device of FIG. 14A showing internal assemblies of micro-fluidic circuits, assay results detectors, and electronic signal processing components according to the teachings hereof;

FIG. 15A is a perspective schematic view of a fluidic patch device according to another particular embodiment hereof which includes flow-through assembly to continuously provide blood sample into the patch for diagnostic testing according to certain related fluid-flow embodiments of the present inventions;

FIG. 15B is a perspective cut-away pictorial view of the patch device of FIG. 15A showing internal assemblies of micro-fluidic circuits, assay results detectors, and electronic signal processing components according to the teachings hereof;

FIGS. 15C and 15D depicted a series of related cross-sectional side views showing the progression of a sample through a fluidic processing circuit of the patch device of FIGS. 15A and 15B to perform a SAR-COV-2 (COVID 19) antibody test;

FIG. 16A is a perspective schematic view of a fluidic patch device according to yet another particular embodiment hereof which includes an absorption pad assembly to continuously provide body perspiration transfer into the patch for diagnostic testing according to certain related fluid-flow embodiments of the present inventions;

FIG. 16B is a perspective cut-away pictorial view of the patch device of FIG. 16A showing internal assemblies of micro-fluidic circuits, assay results detectors, and electronic signal processing components according to the teachings hereof;

FIG. 17A is an enlarged detailed plan view of a single micro-fluidic circuit including an assay results detector which may be employed in conjunction with various embodiments of the diagnostic devices of the present invention;

FIG. 17B is a view similar to FIG. 17A including an emitter and detector assembly implemented in conjunction with the illustrated micro-fluidic circuit;

FIG. 18 is a diagrammatic representation of an example of an emitter and detector assembly employing graphene electrodes to emit visible or ultra-violet light onto captured bio-material in a disease-detection device of the present invention and provide analysis of the photonic energy after a light-matter interaction between the captured bio-material the emitted light;

FIG. 19 is a pictorial view of various principal elements encompassing the inventions hereof as viewed from a broad system perspective which may be deployed across large populations such as in schools or universities and as may be extended by application to cities, states, or entire countries nationwide;

FIGS. 20A to 20C present skyline outlines of certain populous cities that have had experiences with prior pandemics that may better benefit from the inventions hereof when confronting future pandemics;

FIG. 21 is a perspective view of a box of packaged testing and contact tracing patches including RFID tags in accordance with certain aspects of the present inventions which may be deployed within populous city environments during an epidemic, pandemic, or other infectious outbreak;

FIG. 22A is a simplified block diagram showing the reporting of pandemic information along a chain-of-command of health officials according to certain aspects of certain methods of the present invention;

FIG. 22B is a block diagram showing additional input reporting of pandemic information at the different levels of the chain-of-command of FIG. 22A according to certain related aspects of these embodiments of the present invention;

FIG. 23A is a pictorial representation illustrating use of the wellness patches of the present inventions to test, contact trace, and socially isolate members of a populous community;

FIG. 23B is a pictorial representation illustrating patch-to-patch contact tracing according to certain methods of the present invention;

FIG. 23C is a pictorial representation similar to FIG. 23B showing patch-to-phone contact tracing according to certain other methods of the present invention;

FIG. 23D is a pictorial representation similar to FIGS. 23B and 23C presenting a combination of patch-to-patch, patch-to-bracelet, and patch-to-phone contact tracing methods according to certain additional teachings of the present invention;

FIG. 24 is a pictorial representation of using patches of the present invention for community anti-body testing;

FIG. 25A is an exploded perspective pictorial view of certain principal elements of the cough or sneeze pad of the replaceable assay cartridge illustrated in FIG. 4C-1;

FIG. 25B is an exploded perspective pictorial view of certain principal elements of the finger-wipe pad of the replaceable assay cartridge illustrated in FIG. 4C-2;

FIGS. 25C and 25D depicted a series of related cross-sectional side views showing the progression of a sample through a fluidic processing circuit of the cartridge device of FIGS. 25A and 25B to perform a COVID-19 infectious disease test; and FIG. 26 is a pictorial view of certain animal live stock using a disease detection patch as adapted for veterinary applications.

DETAILED DESCRIPTION OF THE PREFERRED EMBODIMENTS

The headings provided herein are for convenience only and do not necessarily affect the scope or meaning of the claimed inventions hereof.

Above referenced, commonly-assigned, and herein previously incorporated by reference Provisional Application Ser. No. 62/972,657 filed Feb. 11, 2020 titled Wearable Patches for Babies, discloses devices, methods, and systems related to patches that can be utilized on babies to detect one or more conditions indicative of an illness. For example, detection of an elevated temperature can indicate a symptom of an illness such as a cold or flu.

In some implementations of the present inventions, at least one or more of the features disclosed in said commonly-assigned 62/972,657 as titled Wearable Patches for Babies can be utilized to sense and monitor similar conditions associated with children such as school-aged children. It will be understood that at least one or more features disclosed in said 62/972,657 as directed to the health and wellness of infants can also be utilized with one or more persons in other age groups. Similarly, it will be understood that at least one or more features of the present disclosure can also be utilized with one or more persons in other age groups, including infants, children, students of all ages including university students, and adults of all ages including the elderly who may be resident at home or in long-term care facilities.

Figure 1A:
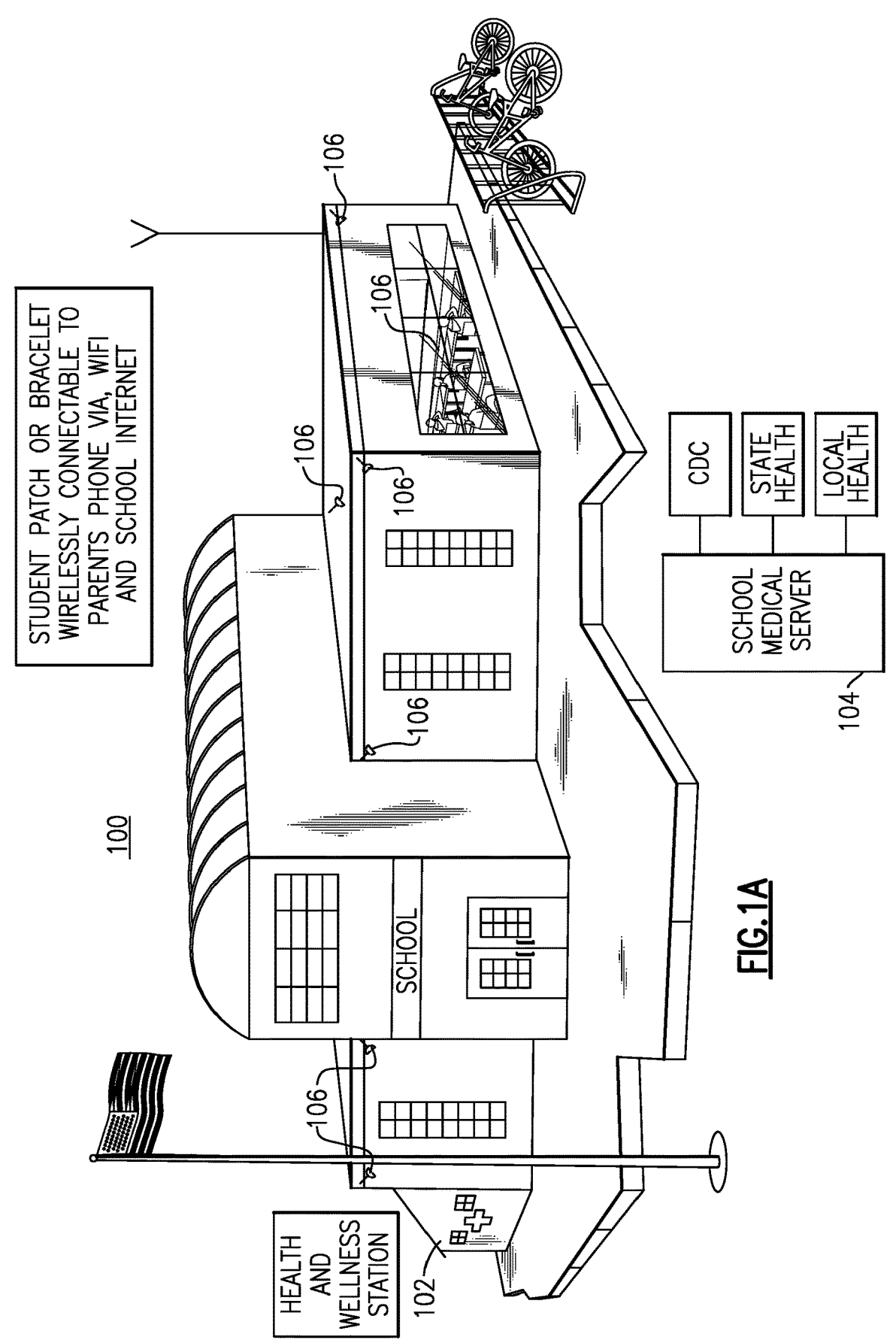
FIG. 1A is a pictorial perspective view of a school building equipped with networking connectivity and interoperability with personal health and wellness systems, devices, and components according to various aspects of the present inventions.

With reference now initially to FIG. 1A, there is shown a pictorial perspective view of a school building 100 equipped with networking connectivity and interoperability with personal health and wellness systems, devices, and components according to various aspects of the present inventions. According to the teachings hereof as disclosed in conjunction with the inventions and various objectives hereof, the school building 100 includes a health and wellness station 102 which is equipped with a medical server 104 which in turn has secure connection with local health officials, state health officials, and national health officials such as the United States Centers for Disease Control and Prevention (CDC). According to certain aspects of the present invention, the school building 100 is further equipped with receivers 106 that are enabled to receive health and wellness reporting signals transmitted by the medical patches and bracelets disclosed herein. The receivers 106 may be implemented with any current or future mid-range wireless communications technology such as WiFi, Bluetooth, or Zigbee and in one preferred embodiment hereof the receivers 106 are securely connected to only the school medical server 104 so as to preserve and maintain the confidentiality of student medical information. As further represented in FIG. 1A, the school building 100 includes several classrooms 108 wherein students attend daily class in congregations of typically ten to thirty-five students per room with generally anywhere between six and forty to fifty classrooms per school, as would be typical in hundreds of thousands of schools around the world. In should be readily understood that the school building 100 is not limited to an elementary school but is illustrative of any school including middle schools and high schools and further that the inventions hereof may be readily applied to other such student and child care facilities ranging from daycare centers to universities. And as disclosed in commonly assigned U.S. Provisional Patent Application Ser. Nos. 62/976,295 and 62/972,657 as referenced above, the student patches and bracelets hereof may be advantageously wirelessly connectable directly to their respective parent's mobile phone and/or alternatively indirectly associated therewith via the school medical server 104.

Figure 1B:
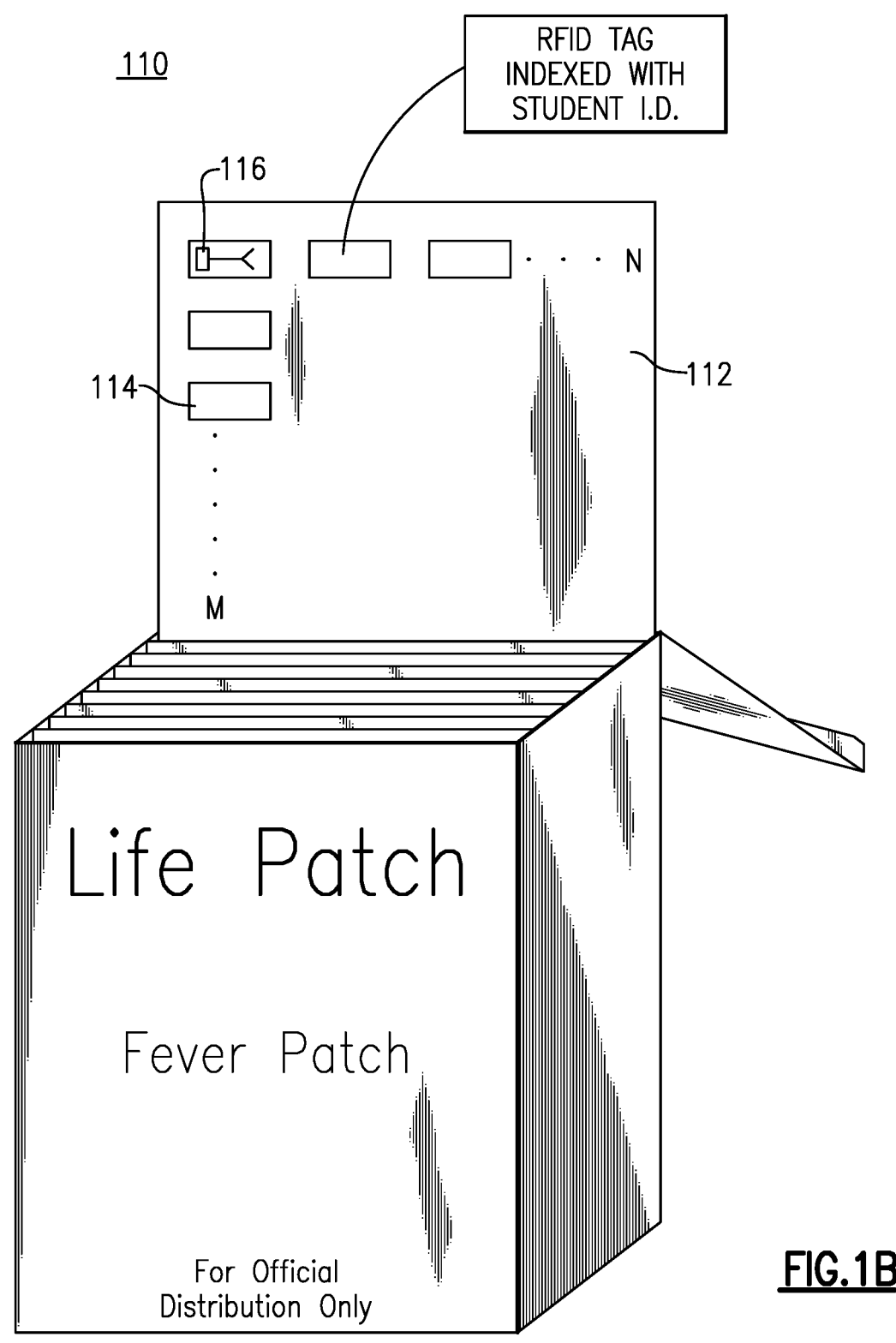
FIG. 1B is a perspective view of a box of packaged wellness patches including RFID tags in accordance with certain aspects of the present inventions which may be deployed within the school environment depicted in FIG. 1A during an epidemic, pandemic, or other infectious outbreak.

Next referring to FIG. 1B, there is shown a perspective view of a box of packaged wellness patches 110 which is filled with any desired number of insert placards 112 with each placard 112 including a desired number of individualized wellness patches 114. The placard 112 many be formed of any suitable boxing or packaging materials such as cardboard and preferably has implemented on one side thereof a non-stick coating such that an adhesive side of the wellness patch 114 may be temporally secured thereon until placed into service according to the teachings hereof. A variety of known non-stick coatings and packaging materials are readily available to achieve these desired aspects of the present inventions. In this embodiment of the present invention, each wellness patch 114 is provided with an RFID tag or circuit 116 that gives a unique identifier to each packaged wellness patch 114 as would be understood by those endeavoring in the art of RFID technologies. Thus as provided by the inventors hereof, the wellness patches 114 each including a respective RFID tag 116 having a unique identifier such as a patch serial number may be paired for use by an individual student by indexing the RFID tag with a corresponding student ID which then may be deployed within the school environment depicted in FIG. 1A during an epidemic, pandemic, or other serious infectious outbreak according to the teaching hereof to thereby achieve the desired community objectives of containment and mitigation by testing, tracing, and isolating as may be recommended by medical experts and epidemiologists to control the distribution and spread of a contagion by social contact.

During the COVID-19 pandemic of 2020, it was reported that the United States federal government spent approximately three trillion dollars to rectify the economic harm caused by the institution of state-wide shut-downs that included shelter-in-place, shelter-at-home, stay-at-home, work-from-home, and best-at-home gubernatorial mandates or other such of similar scope and effect. In addition, it was reported that the US Federal Reserve contributed another three trillion dollars during this pandemic to help stimulate the economy as over 40 million people became unemployed in the United Stats as a result these self-imposed state-wide orders with over 471,500 deaths in the US and over 2,355, 500 reported total deaths worldwide as of the filing hereof. Thus by one simple analysis, six trillion dollars were spent in the US to remedy the economic harm resulting by community resolve to close businesses, schools, and universities national-wide in the Untied States to contain the spread of the COVID-19 virus. And after that six trillion was approved for spending, the US Congress started discussions on another three trillion to combat the economic harm caused the coronavirus pandemic in the US including funding to asset states in their short falls in state revenues resulting from the self-imposed shut-downs. And while the death toll for this pandemic did not exceed such of prior historic pandemics, it is believed that these self-imposed shut-downs in the US and worldwide lead to economic harm that far exceeded any previous economic harm of any prior pandemic both in the US and in the aggregate worldwide as thus far experienced in the course of world history. Further, according to United Nations (UN) reporting in August of 2020, regular in-person school learning was disrupted in over 160 different countries effecting over one billion students worldwide, and as at-home leaning continued as a substitute to in-person leaning, the negative effects on world youth were further understood and documented.

It should be expressly understood that the intent of the inventors hereof is not to critique with hindsight the policies used to contain and mitigate the spread of the COVID-19 virus but rather to provide a more cost effective solution in the wake of our shared experiences therewith. For example, given the effectiveness of modern manufacturing techniques and economies of scale in the arts of semiconductors, electronics, and medical consumables, the wellness patches hereof may be cost-effectively manufactured by the hundreds of thousands or even by the tens of millions when needed as a preferred platform for testing, contact tracing, and isolating such that when applied at an early stage of an outbreak according to the processes, methods, and systems disclosed herein, the spread of any infectious disease may thereby be better contained to preserve community health so that the need for wide-spread economic shut-downs to achieve social distancing may be avoided which in turn would substantially lessen the resulting fiscal harm to local, state, national, and international economies.

Figure 1C:
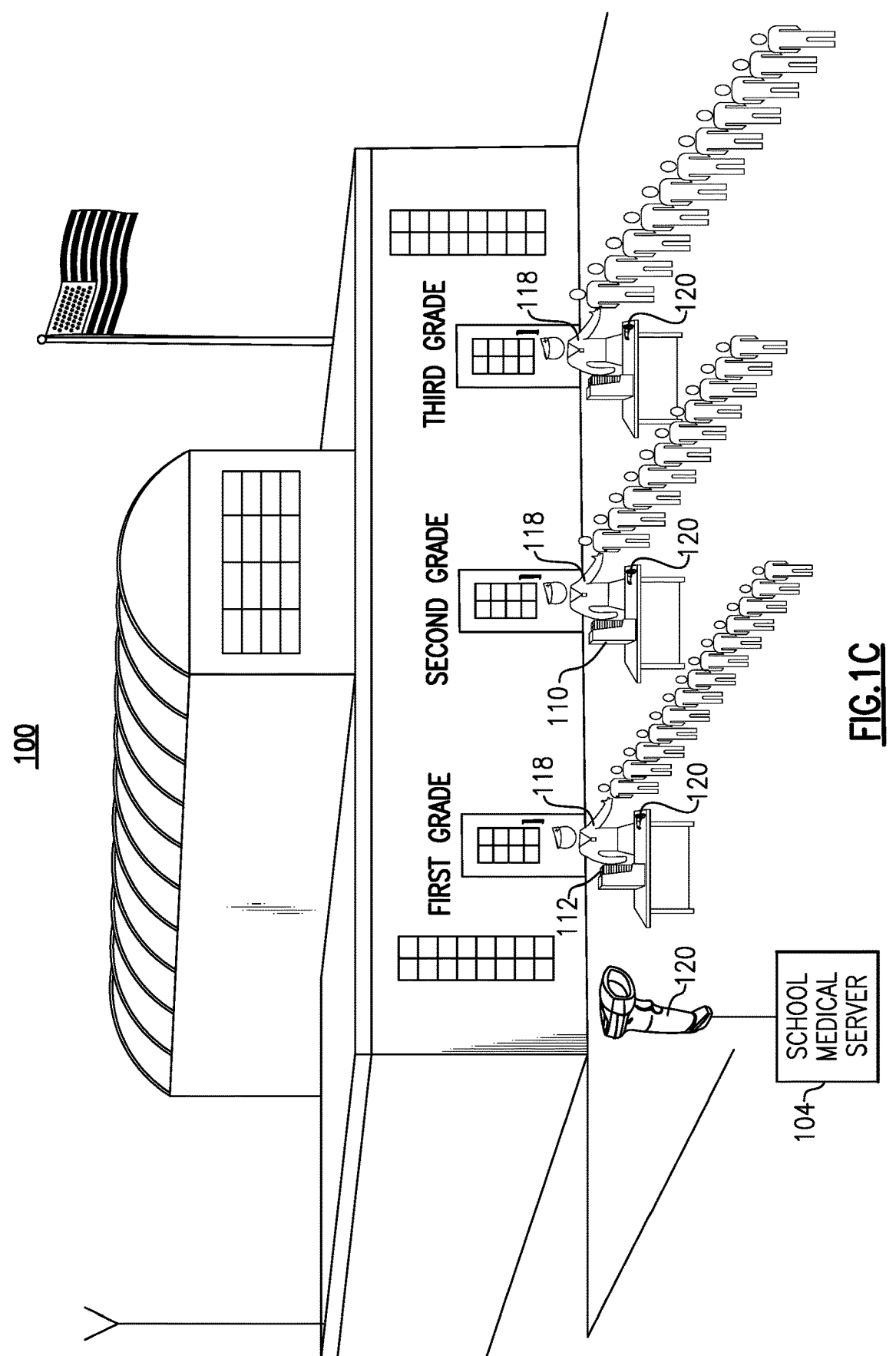
FIG. 1C is a pictorial perspective view of the back of the school building of FIG. 1A illustrating initial application of the wellness patches of FIG. 1B as the school day begins so as to achieve normal teaching operations during a possible infectious outbreak.

Thus with reference now to FIG. 1C, there is shown a pictorial perspective view of the back of the school building 100 of FIG. 1A illustrating initial application of the wellness patches 114 of FIG. 1B as the school day begins so as to achieve normal teaching operations during a possible infectious outbreak. As illustrated in FIG. 1C, school children may line-up for entering their class room in the usual way. Then to achieve the goal of promoting community wellness as provided herein, a medical professional 118 applies a wellness patch 114 to each student and as further shown, a scanner 120 linked to the school medical server 104 is used by the medical professional 118 to scan each patch 114, read its respective RFID tag 116, and index each respective patch ID with its corresponding student.

Figure 1D:
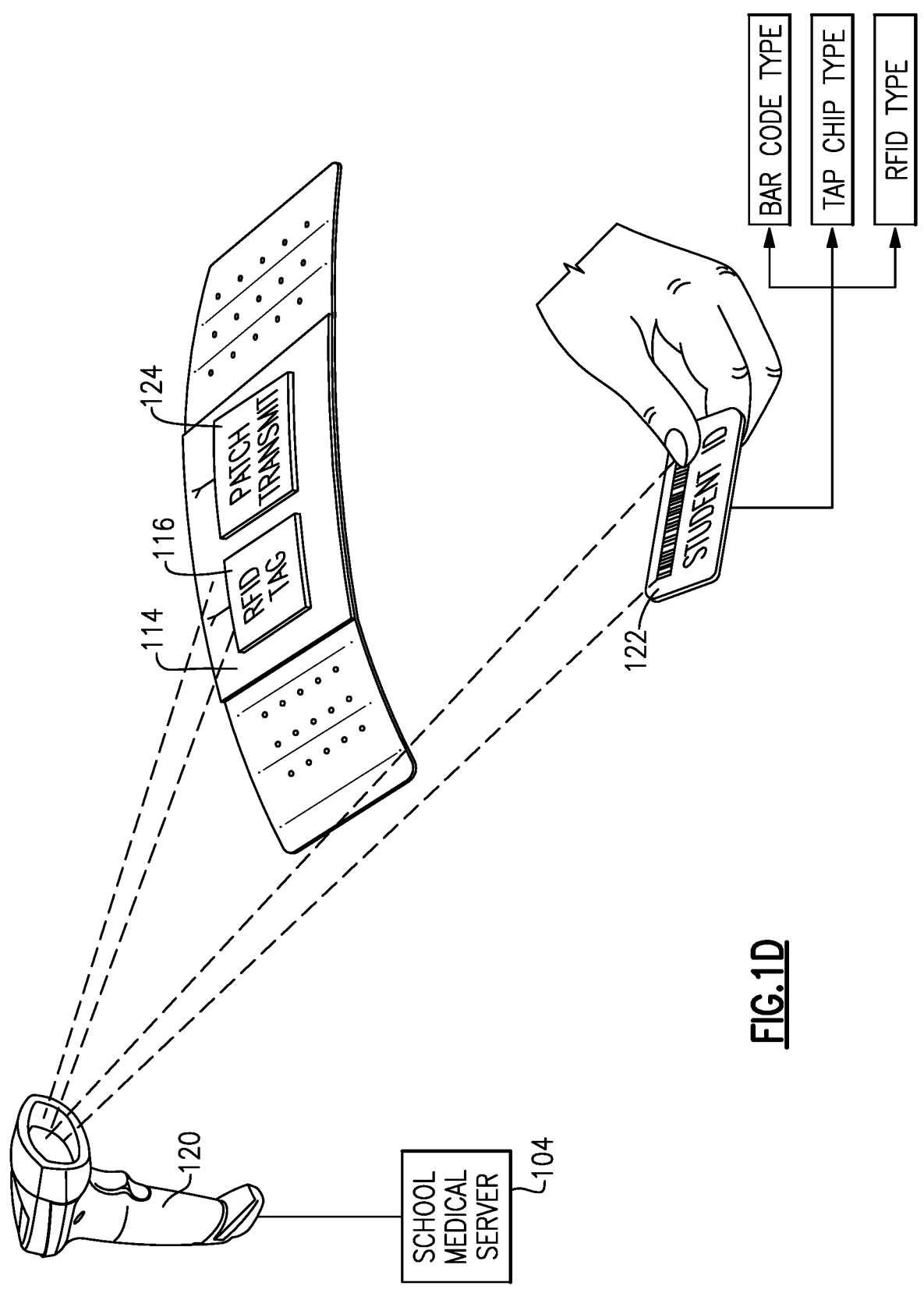
FIG. 1D is a perspective pictorial representation of scanning and indexing a wellness patch and student identification card according to the certain aspects of the methods of the present inventions illustrated in FIG. 1C.

Further details regarding the scanning and indexing discussed in connection with above FIG. 1C are now illustrated in FIG. 1D. As shown, the scanner 120 scans the RFID tag 116 in the patch 114 and also concurrent therewith or otherwise in association therewith, the scanner 120 scans a respective student's ID card 122 so that the student and patch are thereby indexed together and logged in the school medical sever 104 as illustrated. As further illustrated, the student ID may be in typical card form of the bar code type, chip type, or RFID type and may be carried in the typical way or alternatively for elementary and middle school students may be secured on a lanyard and worn accordingly, and as a further alternative to the foregoing, the student ID may be implemented electronically in a bracelet worn by the student throughout the school day. And according to further aspects hereof, the patch 114 may further include a transmitter 124 that is further described herein below in further detail, and in connection with implementation in different institutional settings as discussed below, the ID card 122 may be implemented as an employee ID, resident ID, or alternately may be a driver's license, a passport, or any other official form of personal identification such that a patch according to these inventions may be indexed therewith to achieving the objectives, results, and goals of the various embodiments of the systems, methods, and processes described and claimed herein.

Figure 1E:
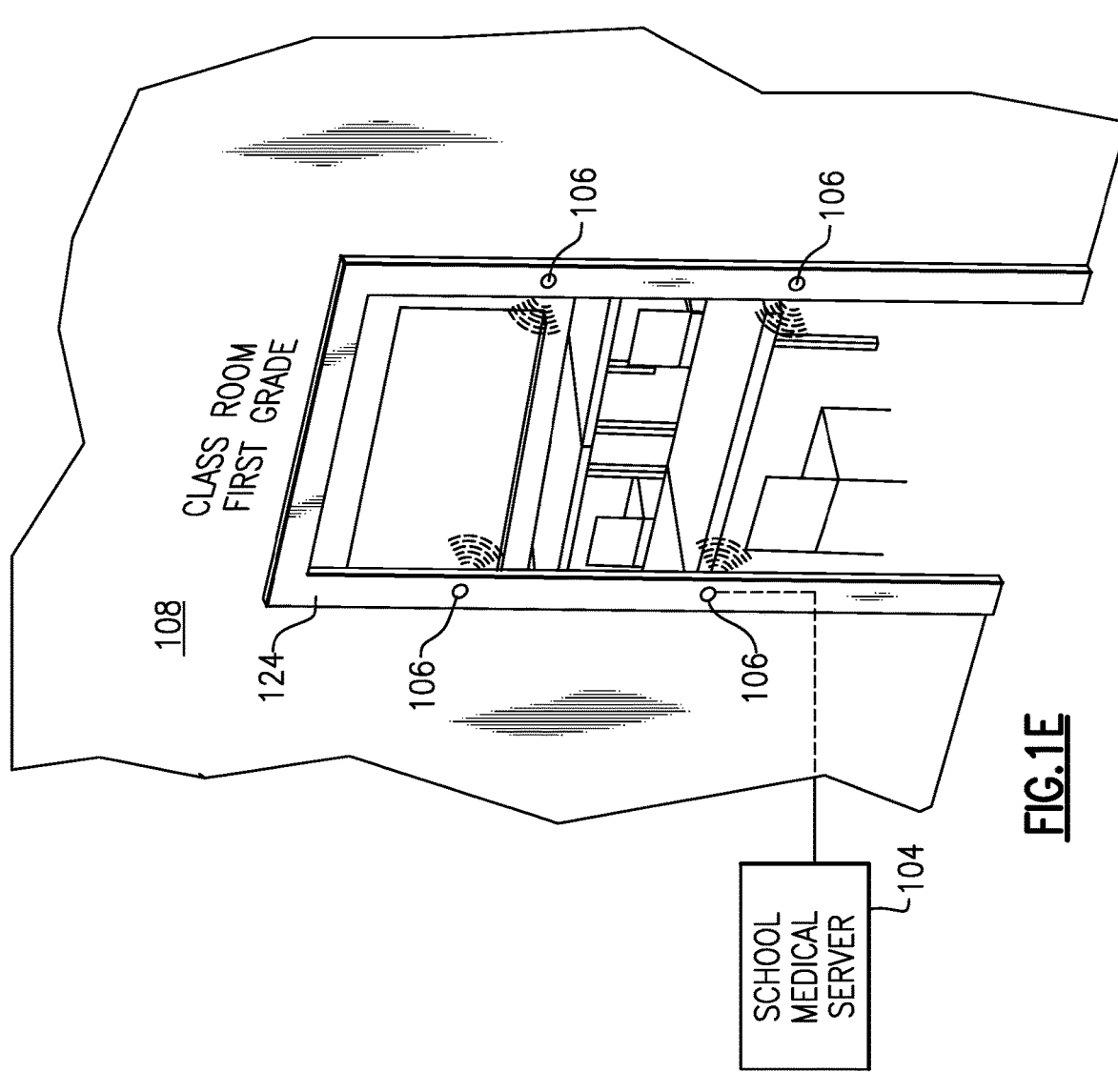
FIG. 1E is a perspective pictorial representation of entrance way inside the school of FIG. 1A as equipped with patch reading and reporting electronics according to additional aspects of this invention.

FIG. 1E is a perspective pictorial representation of entrance way 124 into a typical classroom 108 inside the school of FIG. 1A as equipped with patch and bracelet reading and reporting electronics according to additional aspects of this invention. More specifically, receivers 106 are implemented in the entry way 124 and as a student enters or exits the class room, the receivers 106 receive a transmitted signal from the patch or bracelet which carries information about the containing health and wellness of each student which may include whether the student is running a fever.

It should be readily understood in view of the above discussion of FIGS. 1A to 1E, that the present inventions as disclosed herein are not necessarily limited to a school environment but rather may be implemented in any institutional setting wherein a threshold number of individuals from different households congregate for any number of hours over a daily period of time such as a daily daycare period, school day, or work day as well as any institutional or group setting including an overnight period such as with universities having students staying in dormitories, nursing homes having elderly as residents, or traveling work groups bunking together in temporary sleeping quarters. Thus as such, one principal embodiment of the present is directed to a system for preventing the spread of an infectious disease in an institutional setting including a wearable diagnostic device configured to support a plurality of components and to be worn by a member of the institutional setting, a sensor implemented at least partially within the wearable diagnostic device configured to sense a condition of a respective institutional member while attending or performing an activity within the institutional setting, a transmitter circuit implemented at least partially within the wearable diagnostic device being in communication with the sensor and configured to transmit information representative of the sensed condition to a location external to the wearable diagnostic device, at least one receiver circuit implemented within the institutional setting configured to receive the transmitted information, and a processor operably associated with the at least one receiver circuit configured to analyze the transmitted information to determine whether the sensed condition is indicative of an infectious disease so that an institutional member with such a sensed condition may be identified and cared for according to established standards for community health and wellness. As indicated above, this system may be advantageously deployed in a school, university, or daycare center for children as well as within other institutional settings such as nursing homes for the elderly and work places such as office buildings, factories, and processing plants such as meat processing plants or other protein processing plants critical to maintaining a food supply for a corresponding population. With the embodiments described above in conjunction with FIGS. 1A to 1E, various additional embodiments of the systems, methods, and processes hereof including further embodiments and uses of related patches and bracelets along with additional features and aspects contributing to all thereof and advantages accruing there-from will be discussed next with regard to FIGS. 2A to 2C and all such following as illustrated and describe herein below.

Thus with reference next to FIG. 2A, there is shown a perspective schematic view of a non-invasive patch device according to one particular embodiment hereof used to detect a fever temperature of a user thereof. In this embodiment, the patch device is configured as a fever patch or fever-detection patch 126. The fever patch 126 includes a substrate 128 which further includes a thin adhesive layer or coating 130. The adhesive layer 130 allows the fever patch 126 to be worn on a skin surface of a user in a manner described in the above referenced and incorporated related applications. The fever patch 126 is provided with a temperature sensor 132, a processor 134, and a transmitter which is provided with an antenna 138. In use according to this embodiment, the fever patch 126 is applied to an individual on a selected part of the epidermis whether under clothing or otherwise visible as preferred and the temperature sensor 132 then monitors the body temperature of the user during the course of the day or other selected time period. The processor 134 is operably engaged with the temperature sensor 132 and when the body temperature of the user exceeds a predetermined threshold, for example, 100 degrees Fahrenheit, the processor 134 activates the transmitter 136 to send a wellness signal, via the antenna 138, to a remote receiver such as the receivers 106 discussed above in conjunction with FIGS. 1A to 1E. In this manner, when the wellness signal is further received by an appropriate, designated, or otherwise authorized person, such as a parent, school nurse, or other healthcare worker or other such duly appointed caretaker such as a nursing home attendant or nurse, the user with the elevated temperature may be advised and cared for accordingly.

Thus continuing with FIG. 2B, there is illustrated a block diagram showing the principal steps of one particular method of implementing the patch device of FIG. 2A according to certain aspects of the present inventions. In this embodiment as shown at step 140, the fever patch 126 is applied to a student to monitor the student's temperature while at school. The patch 126 may be applied by a parent at home before the school day begins where the parent would pair for secure communication the patch 126 to the parent's phone or other smart device by a close-range wireless hand-shaking between the two devices, or the patch 126 may be applied by an authorized school medical team member such as the member 118 shown in FIG. 1C. Then at step 142, the temperature sensor 132 detects a temperature reading, in the respective student wearing that respective unique patch 126 as indexed with the student's ID number in the school medical server 104 and/or otherwise paired with the student's parent's smart device, and in the event the temperature reading is above a selected threshold for wellness, the processor 134 is engaged to generate a wellness alert signal as illustrated at step 144. Then at step 146, the transmitter 136 sends a wellness alert signal to a remote receiver such as the receiver 106 shown and discussed above in FIG. 1E or otherwise directly to the parent's phone, or other smart wireless device such as a tablet or laptop computer, via the school WiFi system and Internet.

A normal body temperature is approximately 98.6 degrees F. but may fluctuate depending on different factors. Low grade fevers range between 98.6 and 100.4 degrees F. Moderate grade fevers range between 100.4 and 102.2 degrees F. High grade fever is greater than 102.2 degrees F. A temperature reading at or above 104 degrees F. is called hyperpyrexia and requires immediate care. The CDC considers a person to have a fever when he/she has a measured temperature of 100.4 degrees F. Thus for certain preferred embodiments hereof, a first temperature threshold may be set at 100.4 degrees F., upon which an alert should be sent out. An emergency alert should be sent out when temperature reaches 102.2 degrees F.

One of the symptoms of Covid-19 is shortness of breath, breathing difficulty or generally referred to as respiratory distress. Shortness of breath, breathing difficulty, respiratory distress can be assessed by monitoring oxygen level, heart rate, or both. In addition to temperature sensor, the fever patches and bracelets hereof may be augmented by including oxygen level and heart rate sensing functionalities.

Healthy people usually have a blood oxygen level above 95%. An oxygen level below 90% or under 60 mM Hg is considered low and should be alerted by the present wearable health devices. Blood oxygen level can be measured non-invasively based on the amount of infrared red light energy the blood absorbs. Oxygen level sensors are known to those of skill in the art of body sensors including, for example, Masimo's iSpO2 and Cercacor's Ember.

An increase in the number of breaths per minute may indicate that a person is having trouble breathing or not getting enough oxygen. Low oxygen levels may cause an increase in heart rate. For children ages 6 to 15, the normal resting heart rate is between 70 and 100 bpm. A resting heart rate of over 100 beats per minute for children over 10 years of age, over 130 bpm for children under age 10, and over 120 bpm for infants is considered a rapid pulse and should be alerted. Heart rate can be measured non-invasively by measuring the amount of reflected red light and absorbed green light. Heart rate sensors are known to those of skill in the art of body sensors and are readily adapted to the wearable health detection devices hereof.

Then next in FIG. 2C according to further social and community aspects of the present invention, there are presented some selected patch configurations that may be used to embody any of the integrated diagnostic functionalities hereof, as discussed above or subsequently herein below, so as to promote social acceptance, community service, and personal pride associated with acting on behalf of the betterment of a community group or other such populace grouping wherein interpersonal interactions commonly occur throughout the day. Thus as illustrated and further suggested, the patches hereof may be presented or otherwise packaged for wearable use in the form of a national flag, a state flag, or a school, university, or company logo. And depending on the country, state, school, university, or company, and any particular international, national, local, or institutional cultural aspects thereof, those engaged with designing a final form for final use of these inventions as worn on a person at times in plan view of others in the community, may select from the configurations show in FIG.

2C or such others as may be inspired there-from according to any desired number of variations thereof as so selected and designed to be directed to promote social acceptance, community service, and personal pride in achieving the community health aspects of the present systems, processes, and methods as described and claimed herein. Thus as such, another aspect of this invention is directed to providing visual indicia on an outer surface of any one or more of the patch devices hereof so that the visual indicia thereby provided may be seen by others when the patch device is worn by a user thereof in a preferred manner. This visual indicia may preferably be in the form of a national flag, a state flag, a school logo, a university logo, a sports team logo such as a team name or team city, or a company logo such as a trade name or trade mark.

FIG. 3A is a perspective schematic view of a non-invasive patch device 148 according to another particular embodiment hereof which includes a surface pad 150 implemented to receive and identify a contagion by interaction with droplets from a sneeze or cough or otherwise deposited thereon by way of a finger wipe according to the teachings of various additional aspects of the present invention. As illustrated in FIG. 3A, the surface pad 150 is operably integrated with an assay processing assembly 152 which in turn is associated with a results processing assembly 154 and transmit electronics 155. In this embodiment, the patch device 148 may similarly include the adhesive layer 130 to secure the patch to a skin surface of a user of the device for a desired duration of time as discussed above.

With reference next to FIG. 3B, there is shown a perspective cut-away pictorial view of the patch device 148 of FIG. 3A wherein the surface pad 152 is configured to include a sneeze-pad or cough-pad 156 and finger-wipe pad 158. As illustrated in this embodiment, the sneeze-pad or cough-pad 156 is divided into receptor cells 160 that are provided with various reagents or a single test-specific reagent which are intended for multiple times use to capture and process droplets for a sneeze or cough thought the day's use at school or work. Such assays, reagents, and wellness detection and processing will be further described in additional detail herein below. The finger-wide pad 158 function in a similar manner to the sneeze-pad or cough-pad 156 and as shown and implement is intended to capture any contagions that may be contracted during the school day as children interact in the class room and on the play ground. It should be noted here that the relative sizes of the finger-wide pad 158 and the sneeze-pad or cough-pad 156 may be adjusted as desired for specific users or groups of users and that the patch 148 in various embodiments may be provided with a desired or otherwise specified version of only the sneeze-pad or cough-pad 156, only the finger-wide pad 158, or as shown with both sneeze-pad or cough-pad 156 and the finger-wide pad 158. The patch device 148 as illustration may further advantageously include results indications 162 which may give an indication of detection of a specific contagion by, for example, changing color, or alternatively provide indication of a variety of different contagions where each such different contagion would be assigned a different indictor indicia such as a different color. With continuing reference to FIG. 3B, there is further shown internal assemblies of the patch device 148 including micro-fluidic circuits 164, assay results detectors 166, and electronic signal processing componentry 168.

Cough/Sneeze Pad: Covid-19 testing may be performed by using the cough and sneeze pad hereof by an antigen diagnostic test by detecting specific proteins on the surface of the virus using a strip test similar to a pregnancy test strip.

In current methods, antigen test samples are collected using a nasal or throat swab which typically require the assistance of a health care professional and results can be available in 15 minutes. Result is a color change on the test strip that can be detected using a photometric detector. Immunoassay tests including strip tests as disclosed in the above referenced and incorporated commonly assigned U.S. Pat. No. 9,133,024 are adapted herein and discussed in further detail below in conjunction with FIGS. 25A to 25D.

Covid-19 is known to be transmitted when infected people talk, breath, cough or sneeze. Such viral particles are known to be encapsulated in globs or droplets of mucus, saliva, and water. Single or multiple cough or sneeze droplets may provide sufficient viral proteins for a strip assay to perform as desired. In the case where one cough or one sneeze may not provide sufficient biomaterial for detection, during the day, the student may cough or sneeze multiple times onto the sneeze-pad or cough-pad 156. The immunoassay may be programmed to initiate by a trigger. For example, a trigger can be an electrical signal from electrodes embedded in the sample collection chamber, which when sufficiently wetted, the electrolytes in the sample cause a change in electrical signal that initiates the assay process. Buffer may be preloaded in the patch device or in the removable assay cartridge, discussed below in further detail in conjunction with FIGS. 4B, 25A, and 25B, such that it is released into the sneeze-pad or cough-pad 156, mixes with the sample, and carries the sample into the test strip for analysis.

In an alternative embodiment, a nasal swab may be provided as a specimen. For example, if the school nurse or a parent is notified of a fever alert, and the student/child does not provide a sneeze or cough, the school nurse or the parent can take a nasal swab and deposit it on the sneeze-pad or cough-pad 156 on the patch. The swabs may be provided in a kit, with instructions for use, including a buffer and a dropper. Thus, by using a dropper provided in the kit, the nurse or parent can add a few drops of buffer, as instructed, onto the swab in a sterile container and the content is transferred onto the sneeze-pad or cough-pad 156 of the patch.

Covid-19 is provided as an example here, other pathogens can be detected by the same concept or process using a strip test.

FIG. 3B shows multiple receptor cells 160 that are provided with various reagents or a single test-specific reagent. In one embodiment, there is one single test for one pathogen, for example COVID-19. In another embodiment, there may be reagents for several infectious agent detection, such as for example influenza, swine flu, bird flu, Ebola, Marburg, SARS, MERS, and others as may be desired and implemented.

Finger-Wipe Pad: If fingers have been immersed in or come in contact with specimen, for example, by contact with mucus in the nostril, phlegm, or saliva, wiping the finger on the finger-wipe pad 158 should provide the same detection by immunoassay strip tests as described above for the pathogen. However, there may be high false-positives using finger-wipes as the finger may have come into contact with specimen from other people that the student has interacted with or was in close proximity to, such that the specimen that is tested is contaminated and may provide a false result. It may, on the other hand, be indicative of exposure to the pathogen but not necessarily infection. So an infection test should be done using a sterile swab to collect the sample.

With the exception that the tested finger has been immersed in a nasal or oral specimen, bodily fluids extractable from the finger such as sweats or bodily oil may not be ideal specimen for disease detection. Sweat for example has been reported to have some inherent antimicrobial activity. As such, nitrate in human perspiration becomes acidified when appearing on the epidermis or skin surface which there upon generates nitric oxide, considered to be a most potent broad-spectrum antimicrobial agent. And current reporting as based on research conducted during the present world-wide pandemic, indicates that gaseous nitric may be a suitable treatment for some of the severe complications associated with COVID-19. The finger-wipe pad however can be used to detect other relevant clinical parameters indicative of COVID-19 infection, such as for example, blood oxygen level or heart rate, as described above, in association with FIGS. 2A and 2B.

Next in FIGS. 3C and 3D, there is illustrated use of the patch device 148 of FIG. 3B when applied in the crook of the elbow to catch water, vapor, or mist droplets expressed from a cough or sneeze according to certain aspects of the present inventions disclosed herein. As illustrated, a user 170 preferably applies the patch device 148 either on the lower part of an upper arm 172 as shown at 148*a* or alternatively on the upper part of the lower arm or forearm 174 as shown at 148*b*. In either case, when the patch device 148 is applied to either location 148*a* or 148*b*, the patch device 148 will be positioned in crook of the arm or crook of the elbow when a user 170 moves their forearm 174 relative to their upper arm 172 to form an L-shape of the entire arm as shown. Thus as is good social practice as advised by health and medical professionals, when coughing or sneezing either when in a group setting or alone, it is best to sneeze or cough "into your elbow" as is sometimes expressed or as more particularly described and shown, into the crook or fold of the elbow or arm as illustrated in FIG. 3D. Thus in use as shown, when user 170 coughs or sneezes water droplets, aerated mucus or saliva, water vapor from such like, or other such mist or droplets expressed from the cough or sneeze are by force of expression deposited on the receptor cells 160 of the sneeze or cough pad 156 as above shown in FIG. 3B. Then by operation of the patch device 148, any such droplets, mist, or vapor progress by capillary action, absorption, or other such liquid wicking, to mix with the reagents provided in the assay processing assembly 152, FIG. 3A, to perform a desired assay to determine the present and possible identification of a contagion or pathogen such as a virus or bacteria of a certain known or unknown variety. Then when any such is detected, the results processing assembly 154 and transmit electronics 155 are engaged and activated as described above to report the assay results to a remote location so that the user of the patch device may be informed and cared for as per desired health and wellness standards implemented therewith.

Thus according to one principal aspect hereof, there is shown in FIG. 3E a block diagram illustrating the main steps of one preferred method of using the patch device 148 of FIGS. 3A and 3B wherein the user which may be a student attending school during the school day, sneezes or coughs on to the surface pad 150 of the patch device 148 as illustrated at step 176. Next at step 178, the assay results processing assembly 154 performs a test on the biological material received from the cough or sneeze as deposited therein via the receptor cells 160, then at step 180 positive or negative results are determined for a specific test, and finally at step 182 the transmitter electronics 155 report the test results to a remote receiver such as the receivers 106 as shown in FIG. 1E or any other such receiver as may be implemented in the students smart phone, tablet, or laptop computer as used at school during the school day.

Now with reference to FIG. 3F-1 there is shown a perspective cut-away pictorial view of an alternate embodiment 181 of the patch device 148 of FIG. 3B having a cough or sneeze pad for on-body use similarly showing the internal assemblies for micro-fluidics, assay results, and electronic signal processing according to the teachings hereof. In this embodiment 181, the finger-wipe pad 158 shown in FIG. 3B is not utilized and thus as such the surface pad 150 as herein deployed is comprised only of the sneeze or cough pad 156 as shown. Use and deployment of the cough or sneeze pad embodiment 181 of FIG. 3F-1 may proceed as discussed above in connection with the patch 148 with regard to the coughing and sneezing use and deployment thereof, and thus as such need not be repeated here for proposes of reader convenience or other such.

With reference next to FIG. 3F-2, there is shown a perspective cut-away pictorial view of an alternate embodiment 183 of the patch device 148 of FIG. 3B having a finger-wipe pad 158 implemented for on-body or off-body use. In this embodiment 183, the sneeze or cough pad 156 shown in FIG. 3B is not utilized and thus as such the surface pad 150 of the alternative embodiment 183 is comprised only of the finger-wipe pad 158 as shown. As further illustrated, the finger-wipe pad 158 includes individual finger-wipe dimplets 184. The dimplets 184 are preferably designed with acute edges 186 as shown so the when a user wipes their finger across the pad, any accumulated material on the finger such as dirt, body oil, sweat, dead skin cells, and the like that may provide a medium that captures and holds active viruses, bacterium, or any other such disease causing pathogens will be removed from the finger and thus by wiping action be transferred on to collection material 188 provided in the finger-wipe dimplets 184 so that the reagents provided in proximity to the dimplets 184 in a collection chamber 190 of the micro-fluidic channels 164 may begin to assay any and all biological material deposited therein according to this aspect of the present inventions. Then as discussed above in conjunction with FIG. 3B, the results detectors 166 are engaged and any detected assay results are reported by the electronic components 168. As would be readily apparent to those skilled in the art of assay development in view of the disclosure hereof, the collection material 188 may be made from any suitable natural or manufactured materials such as cotton, gauze, nylon, or spun polyesters and is preferably made from natural cotton treated with a hydrophobic dressing to promote the flow of collected biological substances from the finger, through the collection material 188, and then into the collection chamber 190 for testing as described and shown herein.

Next, FIG. 3G illustrates an on-body application of the patch device 183 of FIG. 3F-2 wherein the user 170 applies the patch 183 to the inside of their forearm 174 in a corresponding longitudinal direction as shown. In this manner, if the user 170 is right-handed, they would wipe a right finger such as their index finger across the wipe-pad 158 preferably from top to bottom in a downward motion as further illustrated below in FIG. 3J.

Then next in FIG. 3H, there is shown one example of an off-body application of the patch device 183 according to additional personalized wellness aspects of the present invention wherein the patch 183 is applied in a discrete manner to a student's notebook 192 for use during the school day. In this manner, the patch 183 may be maintained out-of-view of classmates and still carried by the student as a personal item ready for use at any time when needed or desired. As would be readily apparent by those skilled in the art of bio-patches given the disclosures hereof, this particular off-body embodiment illustrated by the patch 183 is attainable because in the absence of the cough or sneeze pad 156, FIG. 3B above, the addressable use location of the patch device is extended to private or public off-body surfaces readily accessible by the user. Thus application off-body is not necessarily limited to student notebooks but may be easily extended to any carried personal item such as a purse, wallet, backpack, mobile phone, tablet, water bottle, lunch box, key fob, pencil box, ID card such as a student ID or employee ID, or a specialized card, holder, or sleeve apparatus specifically designed to support a bio-patch of the type illustrated in the embodiment 183 that may be privately carried by a user, or any other such suitable or desired personal item that may be easily indexed with a particular user thereof and a patch device personally assigned to that particular user.

Thus in view of the above, FIG. 3I presents a block diagram presenting an initial step 194 of one preferred method of using the patch device 183 of FIG. 3F-2 wherein the user 170 or a parent or guardian thereof, applies a finger-wide patch hereof to a desired location on the user's body or alternatively on a personal item to be carried by the user 170 for handy access during the day. And for purposes of full clarity as to the finger-wide aspects hereof, FIG. 3J provides a perspective pictorial view illustrating use of the finger-wipe pad 158 of the patch device 183 whether applied to an on-body or off-body location. Thus here as shown, an index finger 196 is simply wiped across the finger-wipe pad 158 and the assay begins as described above.

FIG. 3K is a block diagram showing the principal steps of one preferred method of using the patch device of FIG. 3F-2 wherein the user which may be a student attending school during the school day, wipes their finger on the finger-wipe pad 158 of the patch device 183 as illustrated at step 198. Next at step 200, the assay results processing assembly 154 performs a test on the biological material received from the finger wipe as deposited therein via the finger-wipe dimplets 184, then at step 180, as with the method above described in connection with FIG. 3E, positive or negative results are determined for a specific test, and finally at step 182 as with the corresponding method step in FIG. 3E, the transmitter electronics 155 report the test results to a remote receiver such as the receivers 106 as shown in FIG. 1E or any other such receiver as may be implemented in the students smart phone, tablet, or laptop computer as used at school during the school day.

Thus with reference again to the above principal device embodiments discussed above in conjunction with FIGS. 3B and 3F, the present invention is directed to a system for preventing the spread of an infectious disease in an institutional setting, the system comprising (i) a portable diagnostic device configured to support a plurality of components and to be carried by a member of the institutional setting, (ii) a surface pad assembly implemented at least partially within the portable diagnostic device and configured to receive biological material from the body of a respective institutional member while attending or performing an activity within the institutional setting, (iii) an assay processing assembly associated with the surface pad assembly configured to perform a wellness test on the biological material deposited on the surface pad by the institutional member, (iv) a transmitter circuit implemented at least partially within the portable diagnostic device being in communication with the assay processing assembly and configured to transmit information regarding the wellness test to a location external to the portable diagnostic device, (v) at least one receiver circuit implemented within the institutional setting configured to receive the transmitted information, and (vi) a processor operably associated with the at least one receiver circuit configured to analyze the transmitted information to determine whether a result from the wellness test is indicative of an infectious disease so that an institutional member with such a determined result may be identified and cared for according to established standards for community health and wellness. Here this system, as similar to those discussed above, may be advantageously implemented in an institutional setting that is a school, university, or daycare center for children as well as within other institutional settings where members gather together or are otherwise congregated such as nursing homes for the elderly and work places such as office buildings, factories, and processing plants such as meat processing plants or other protein processing plants critical to maintaining a food supply for a corresponding population. And further in this system, the biological material received from the body of the respective institutional member is deposited on the surface pad assembly by way of a cough, a sneeze, or by action of a finger wipe. And in addition to these methods of depositing the biological material, where appropriate and suitable provided for, the biological material received from the body of the respective institutional member may be deposited on the surface pad assembly by direct application of spittle, saliva, spit, or mucus from the mouth of the institutional member on to the surface pad assembly.

With reference now to FIG. 4A, there is shown a perspective schematic view of a non-invasive bracelet device, bio-bracelet, medical bracelet, or personal wellness bracelet 202 according to yet another particular embodiment hereof which includes an alternate implementation of surface pad functionalities discussed in conjunction with FIGS. 3A to 3K. As illustrated in FIG. 4A, the bracelet 202 includes a band 203 that is connectable by use of a clasp 204 to enable placement on the wrist of a user in a manner similar to other jewelry-type bracelets or personal time keeping pieces such as wrist watches as is well known. Then according to various aspects of the present inventions, the wellness bracelet 202 along a top portion of the band 203, as shown in this embodiment, is provided with the surface pad 150 as discussed above, the assay processing assembly 152, and a central processing unit or CPU 206. The CPU 206 may be similar to the processing results assembly 154 discussed above in conjunction with the bio-patch 148 but here in this bracelet embodiment, the CPU 206 may be provided with additional electronic memory and computational functionalities as a result of the increased availability of space or "addressable manufacturing real estate" in the bracelet form-factor as compared with the thin wearable patch form-factor. The wellness bracelet 202 of FIG. 4A is then also provided with the transmit electronics 155 which similarly may be inclusive of enhanced transmission functionalities with an increased range given the additional available space for components in the bracelet form-factor as shown. In other embodiments, the principal elements including the removable assay cartridge 208, the CPU 206, and the transmitter electronic 155 may be located at any position around the circumference of the band 203 as desired while the preferred location of the socket 218 is on a top portion of the band as shown so that the cartridge 208 may be replaced while the bracelet is being worn and also to position the surface pad 150 in an accessible location similarly while the bracelet is being worn by a user thereof. Thus as illustrated at method step 207a, when deployed for use, the transmit electrons 155 of the bio-bracelet 202 may be configured to automatically transmit an illness signal including an illness message or notification to an authorized second party so that the designated second party may provide needed assistance to the bracelet user.

FIG. 4B is another perspective schematic view of the non-invasive bracelet device 202 of FIG. 4A illustrating replacement of a removable or replaceable assay cartridge 208 according to a certain aspect relating thereto. As illustrated, the surface pad 150 and assay processing assembly 152 of prior embodiments are herein integrated into the single removable assay cartridge 208 which is replaceable and the cartridge 208 is represented by both a used cartridge 208a illustrated as being removed and a new, fresh, or unused cartridge 208b shown as being inserted into the bracelet 202 for the next use. As shown in further detail, each cartridge 208 includes on the bottom side thereof centering pins 210 that mate with holes 212 in the bracelet 202. In some embodiments of the cartridge 208, at least one of the pins 210 may be implemented to electrically connect the cartridge 208 to the bracelet 202. Such electrical connections enable the cartridge to be powered as desired by a battery that may be supplied in the bracelet and for the cartridge to provide electronic signals to the CPU 206 which carry test result information that may then be transmitted by the transmit electronics 155 as discussed above and in further detailed herein below. Further as shown, the bracelet 202 may be advantageously provided with a pair of barb-tipped detents 214 that mate with slots 216 so that the cartridge 208 may thereby be secured for use in a corresponding socket, opening, recess, or cavity 218 formed in the bracelet 202 as illustrated. Thus after an initial use and test performed while situated in the bracelet as described, the used cartridge 208a may thereafter be removed and disposed of according to applicable safety standards as illustrated and listed in method step 220 of FIG. 4B. Then for subsequent continued use of the bracelet 202, a fresh assay cartridge 208b may be inserted into the socket 218 as shown and recited at method step 222.

FIG. 4C-1 is a perspective pictorial view of a cartridge holder 224 and exemplary replaceable assay cartridges 208 each thereof shown with the surface pad 150 including the sneeze or cough pad 156 and the finger-wipe pad 158 for use in a personal wellness bracelet 202 of the type illustrated and discussed above in conjunction with FIG. 4B. As illustrated, the cartridge holder 224 includes individual receptacles for securing an individual cartridge 208 therein with each such receptacle including a hole 225 so that in use, a user of the cartridge and bracelet may easily use one of their fingers to push on the bottom of the cartridge to release the cartridge from the receptacle for placement in the socket 218 of the bracelet 202 as discussed above. As shown in FIG. 4C-1, the exemplary holder 224 includes, by way of example, five corresponding cartridges 208 as packaged therein for market distribution, sales, and readiness for end use in a bracelet, and as would be understood by those skilled in the art of product packaging for medical supplies, given the disclosures hereof, the packaged assembly of the five representative cartridges 208 with the holder 224 would be further packaged in a hygienic, sterile, or sealed manner with preferably see-through, clear, or otherwise suitable materials such that the packaged item may then be safely displayed and sold in a retail setting for end user direct purchase.

FIG. 4C-2 is a view similar to FIG. 4C-1 presenting an alternate embodiment of the replaceable assay cartridges 208 for use in a personal wellness bracelet of the type illustrated in FIG. 4B showing each cartridge thereof including only a finger-wipe pad 158 for collecting biological material according to certain sample collection aspects of the inventions hereof. Here the finger wipe pad 158 is formed and utilized as discussed above and such cartridges are similarly assembled with the holder 224 and then packaged for sale as also discussed just above in connection with the cartridges of FIG. 4C-1. Further mechanical, biological, and bio-chemical particulars of these exemplary removable and replaceable assay cartridges 208 as implemented according to various additional aspects, characteristics, and functionalities of corresponding and related embodiments of the inventions discussed above are herein provided below in further detail in conjugation with FIGS. 25A and 25D.

And next with regard to use of the bracelet 202 of FIG. 4B, there is provided in FIG. 4D a block diagram showing the principal steps of a certain preferred method of using such a health and wellness bracelet device as exemplified by the bracelet 202. Here similarly as above in the methods discussed in conjunction with FIGS. 3E and 3K for using the patch devices 148 and 183, the user of the present bracelet 202, which may be a student attending school during the school day or an office worker at the office during the work day, coughs, sneezes, or wipes their finger on the surface pad of the bracelet device 202 as illustrated at step 226. Next at step 228, reagents in the assay cartridge 208 perform a test on the biological material received from the cough, sneeze, or finger wipe as deposited therein via the receptor cells 160 of the cough or sneeze pad 156 or the finger-wipe dimplets 184 (FIG. 3F-2), then at step 230, as with the method above described in connection with FIG. 3E, positive or negative results are determined for a specific test, then next at step 232 as with the corresponding method step in FIG. 3E, the transmitter electronics 155 (FIG. 4B) report the test results to a remote receiver such as the receivers 106 shown in FIG. 1E or any other such receiver as may be implemented in the student's or worker's smart phone, tablet, or laptop computer as used at school during the school day or at a work location during the work day. Finally in this embodiment of the bracelet 202, at step 233, the used cartridge 208a in FIG. 4B, may be removed from the bracelet 202 and a new cartridge 208b may be secured for next use in the socket 218 as discussed above.

Thus as described above in connection with FIGS. 4A to 4D in particular and the entirety hereof generally, one particular embodiment of the present invention is directed to a wellness bracelet for use in detecting a disease comprising i) a band for supporting a plurality of components, ii) an assay cartridge including a surface pad, the surface pad configured to receive biological material from a user of the bracelet and the assay cartridge configured to perform a diagnostic test on the biological material, iii) a central processing unit (CPU) implemented within the band and the CPU operatively connected to the assay cartridge to receive information from the diagnostic test performed on the biological material by the assay cartridge, and iv) transmit electronics implemented within the band and operatively connected to the central processing unit, the transmit electronics configured to transmit a results signal including at least some of the information from the diagnostic test performed by the assay cartridge. In one specific embodiment of this wellness bracelet, the assay cartridge is removable so that when a first assay cartridge is fully depleted, the first assay cartridge may be removed from the bracelet and a new second assay cartridge is then positioned in place of the first. In any of the embodiments hereof, the results signal may be transmitted to a remote receiver, to a display provided on the band, or to both. And in connection therewith, there is also provided a method of using a wellness bracelet for detecting a disease, the method comprising the steps of i) depositing biological material into a first assay cartridge provided in association with the bracelet, ii) performing a diagnostic test on the biological material deposited in the assay cartridge, iii) obtaining a result from the diagnostic test performed on the biological material, iv) transmitting the result from the diagnostic test to a remote receiver, removing the first assay cartridge from the bracelet, and providing a second assay cartridge in place of the first assay cartridge.

FIG. 4E-1 is a perspective schematic view of a non-invasive fever-detection bracelet 234*a* according to yet another particular embodiment hereof which includes an alternate implementation of temperature sensing functionalities discussed above in conjunction with the fever patch of FIG. 2A. The fever-detection bracelet 234*a* (or for purposes of brevity hereinafter, "fever bracelet" or "fever-bracelet") similarly includes the temperature sensor 132, the processor 134, and the transmit electronics 155. And given the illustrated form-factor, the fever-bracelet 234*a*, as with the bio-bracelet 202 of FIG. 4A, includes a band 203 that is connectable by use of a clasp 204 to enable placement on the wrist of a user in a manner similar to other jewelry-type bracelets or personal time keeping pieces such as wrist watches as is well known. Further, as may be alternatively desired by end-user consumers, the functionalities of the wearable fever-detection device of FIG. 4E-1 (and of FIG. 4E-2 discussed below in conjunction therewith) may be delivered in a form-factor such as a smart watch of the type currently commercially available in the market place or such a smart watch that is somewhat modified by a manufacture thereof to comport well with the inventions hereof. Thus two such suitable form-factors for the bracelets disclosed herein including the wearable fever-detection devices of FIGS. 4E-1 and 4E-2 as well as those discussed above and herein below in further detail, include the "jewelry-type" and the "smart-watch-type".

With continuing reference to FIG. 4E-1, the transmit electronics 155 are preferably configured for long-range communication. Thus here in the embodiments of the fever-bracelets of FIGS. 4E-1 and 4E-2, and as may be desired with other bracelets disclosed herein, the bracelet is provided with long-range communication functionality such that the bracelet may communicate automatically with a designated second party's mobile phone or other personal wireless mobile device such as a tablet or laptop computer, or where otherwise desired a personal desk-top computer. Thus as illustrated at method step 207*b*, FIGS. 4E-1 and 4E-2, when deployed for use, the transmit electrons 155 of the fever-bracelets 234*a* and 234*b*, respectively, may be configured to automatically transmit a fever signal including a fever message or notification to an authorized second party so that the designated second party may provide needed assistance to the bracelet user. And as above, as discussed in conjunction with the bio-brackets 202, this communication functionality implemented in the fever-bracelets 234*a* and 234*b* may be initiated via a local WiFi system to then send the fever message or signal 207*b* for subsequent dispatch over the Internet or alternatively, the fever message or signal 207*b* may be dispatched directly over a commercially available cellular network system such as the 5G systems currently being deployed extensively. Thus when deployed in use, when the second party is a parent or other guardian at work or home at some extended distance from the bracelet user, this bracelet-to-second-party communication may be facilitated through various intermediate nodes in a communications network existing between the bracelet and the second party's cell phone, smart phone, tablet, or other personal wireless device as would be well understood by those skilled in the relevant arts of wireless telecommunications given their appreciation of the inventions disclosed herein.

FIG. 4E-2 is a perspective schematic view of an augmented embodiment of the fever-bracelet of FIG. 4E-1 showing a fever-bracelet 234*b* including a display monitor 235 for posting a fever indicator viewable by the bracelet user. Thus in this manner, when the transmit electronics 155 transmit the fever signal 207*b* to a designated second party, preferably concurrent therewith, the display monitor 235 flashes or otherwise posts or displays readable indicia to the bracelet user that a fever has been detected by their fever bracelet.

Non-invasive bracelet-fever detection may comprise sensors for monitoring additional symptoms of respiratory distress such as low oxygen level or rapid heart rate, as discussed above in connection with FIGS. 2A and 2B.

Thus as described above in particular in connection with FIG. 4E-1 and FIG. 4E-2 and in view generally of the entirety hereof, the present invention is yet further directed to a fever-detection bracelet for detecting an elevated body temperature indicative of a fever in a user thereof, the fever-detection bracelet comprising i) a band for supporting a plurality of components, the band being wearable by a bracelet user, ii) a temperature sensor implemented at least partially within the band, the temperature sensor configured to detect a body temperature above a predetermined threshold indicative of the bracelet user having a fever, iii) a processor implemented within the band and operatively connected to the temperature sensor to receive from the temperature sensor an indication the bracelet user having developed a fever, and iv) transmit electronics implemented within the band and operatively connected to the processor, the transmit electronics configured to transmit a fever notification to a pre-selected information user. In one embodiment thereof, the bracelet user is a school-aged child and the information user is a parent or other guardian of the school-aged child and alternatively thereto, when the bracelet user is a school-aged child the information user may be an authorized member of a school attended by the school-aged child and in any of the above cases, the school-aged child may be a high school student. And for even further application, the bracelet user may be a university student and the information user is a parent or other guardian of the university student, an authorized member of university health services, or both parent or other guardian of the university student and an authorized member of university health services. And in further embodiments, any of these fever-detection bracelets may further advantageously include a monitor implemented at least partially within the band, the monitor configured to display a fever message to the bracelet user when the transmit electronics transmit the fever notification to the pre-selected information user.

Thus in view of the above, those skilled in the arts of care-taking would appreciate in view of the disclosures hereof, that one important aspect of these inventions is to provide a patch or bracelet user with second party attention. Thus in some applicable situations, the patch or bracelet user is too young, too busy, or perhaps too old, to provide themselves with needed attention so herein as may be implemented and deployed, the patches and bracelets are pre-authorized to automatically communicate with certain selected or otherwise designated second parties to provide such a patch user or bracelet user with care and attention as may be warranted, desired, or otherwise necessary for the benefit of all stakeholders engaged therewith.

Now moving on to FIG. 5, there is shown that in some embodiments, a patch 236 according to any the inventions described herein above or below as worn by a user such as a child 238 at school can communicate with a monitor 240 through a communication link 242 that includes one or more intermediate devices 244, similar to the example disclosed in reference to FIG. 8B of Appendix 1 as referenced above. More particularly, the communication link 242 of FIG. 5 can include a first communication link 245*a* between the patch 236 and one or more intermediate devices 244, and a second communication link 245*b* between the intermediate device (s) 244 and the monitor 240.

FIG. 6A shows that in some embodiments, the present invention further provides a system 246*a* that can be configured to monitor a plurality of children each wearing a patch having one or more features as described herein and as discussed herein below in conjunction with the system 246*b* of FIG. 9. More particularly, as illustrated in FIG. 6A, the system 246*a* can be configured to monitor a group of children (e.g., 238*a*, 238*b*, 238*c*, 238*d*) with respective patches (236*a*, 236*b*, 236*c*, 236*d*) and a monitor 240.

In the example of FIG. 6A, a given patch can include a unique identifier, such as the RFID tag 116 discussed above in FIG. 1B, that allows the patch to be uniquely identified among patches that are otherwise similarly configured. Thus, the patch 236*a* can include a unique identifier; the patch 236*b* can include a unique identifier; the patch 236*c* can include a unique identifier; and the patch 236*d* can include a unique identifier. And as would be understood by those skilled in the art of high volume manufacturing, such unique patch identifiers may be extended from thousands to tens of millions of deployed system patches by manufacturing methods suitable for such like.

In some embodiments, the system 246*a* of FIG. 6A can be configured such that a communication link between a given patch and the monitor 240 includes a unique identifier information associated with that patch. Thus, a communication link 242*a* can include a unique identifier information associated with the patch 236*a*; a communication link 242*b* can include a unique identifier information associated with the patch 236*b*; a communication link 242*c* can include a unique identifier information associated with the patch 236*c*; and a communication link 242*d* can include a unique identifier information associated with the patch 236*d*. It will be understood that each of the foregoing communication links may or may not include an intermediate device and that such communication links may be extended to any desired number for a given system of patches.

Based on the examples of FIGS. 5 and 6A, those skilled in the relevant arts may appreciate that one or more patches and one or more related systems can be implemented to monitor the well being of a child, even if the child is away (e.g., at school) from a caregiver such as a parent.

For example, and referring to FIG. 5, suppose that a child wears a patch having one or more features as described herein (e.g., applied by a parent), and provided with a portable communication device such as a mobile phone. When the child is at school, the patch can sense one or more conditions indicative of an illness such as a flu or cold. For the purpose of description, flu is used as an example illness; however, it will be understood that other illnesses can also be monitored.

When a symptom of a flu (e.g., fever) is detected by the patch, or by use of the patch, the patch can communicate with the mobile phone functioning as an intermediate device (244 in FIG. 5), and the intermediate device can notify a monitoring device (240 in FIG. 5) (e.g., a mobile phone with or nearby a parent). Such a notification provided to the monitoring device can be a simple qualitative notice (e.g., "fever detected"), can include some quantitative information (e.g., "fever at 101 degrees detected"), or some combination thereof.

Based on the foregoing notification, the parent can take an appropriate action, such as picking up the child from school to thereby better care for the child, as well as to reduce the likelihood of the child spreading the illness to other children.

In another example, and referring to FIG. 6A, suppose that a group of children are provided with patches having one or more features as described herein. Such children can gather at, for example, a school. Such a school 100 is depicted as illustrated above in FIGS. 1A and 1C as well as below in FIG. 9 as discussed in further detail in conjunction therewith, and the system 246*a* can be implemented to include some or all of such a school 100.

FIG. 6B shows diagrammatically, that in some embodiments, a system 246*b* of can include a plurality of patches 236 that can communicate with each other, and/or with an external device. For example, a first group of patches 248*a* and a second group 248*b* are shown to be included in the system 246*b*, and generally in communication with an external device 250. More particularly, the first group 248*a* is shown to include four example patches 236*a*, 236*b*, 236*c*, 236*d*, and the second group 248*b* is shown to include three example patches 236*e*, 236*f*, 236*g*. Such first and second groups 248*a* and 248*b* of patches can be grouped based on, for example, physical proximity/separation, different functionalities, grade level, or any other desired grouping depending on the institutional setting, community group, employee groupings, or other such sub-divided congregations of people who may be closely engaged with each other during a given period of time.

In some embodiments, within a given group, each of the plurality of patches can communicate directly with the external device 250, through a representative patch, or some combination thereon. For example, for the first group 248*a*, the patches 236*a* and 236*b* are shown to have a communication link 252*a*; the patches 236*a* and 236*c* are shown to have a communication link 252*d*; the patches 236*c* and 236*d* are shown to have a communication link 252*c*; and the patches 236*c* and 236*b* are shown to have a communication link 252*b*. Further, the patch 236*b* is shown to be a representative communication member and be in communication over a group link 254*a* with the external device 250. Thus here, for example, the patch 236*b* may be worn by a teacher and the remaining patches in the group 248*a* each assigned to a respective student in the teacher's class room.

In another example, for the second group 248*b*, the patches 236*e* and 236*f* are shown to have a communication link 252*e*; and the patches 236*f* and 236*g* are shown to have a communication link 252*f*. Further, the patch 236*e* is shown to be a representative communication member and be in communication a group link 254*b* with the external device 250. In some embodiments of these systems, the communication links between the patches within a given group can be based on, for example, relative proximity/distance among the users wearing the respective patches, some hierarchy of the users and/or patches, or some combination thereof. In some embodiments, the communication links between the patches can be configured as a mesh network, or be based on such a network. And as would be readily apparent to those skilled in the relevant arts in view of the disclosure hereof and the above discussion, the number of patches in groups 248*a* and 248*b*, while shown as including four and three patches respectively for exemplary purposes, is not limited to such a number but may include any desired number of patches from groups in the tens, to hundreds, to thousands, to tens or event hundreds of thousands with all such each being assigned in a one-to-one corresponding manner to members in a common group. Thus such common groups in application may advantageously include i) students at a school, ii) children at a day care center, iii) residents at a long-term care facility, iv) employees at a work place such as at a single office location, a factory, or an entire office building or a large corporate campus such as those found in major cities or suburban areas around the world, v) students, faculty, and staff at a university or sub-divisions of universities such as dormitories, living houses such as a fraternities or sororities, and university work groups such as labs or all students entering a library to study, vi) sports teams when playing each other, for example, professional baseball where group 248*a* would represent one team and group 248*b* represent the other team or group 248*a* would represent all the players on the field and group 248*b* the professional umpire crew (as perhaps being from two different unions) such that, for example, when a batter hits a single and is thus in close proximity with the first baseman of the opposing team, their respective patches may be in commutation with each other directly or independently in communication with an external device such as the external device 250 of FIG. 6B, vii) private and government employees across multiple work places such as at offices and/or factories at different geographical locations across a city, state, country, or globally worldwide as represented by the two groups of patches 248*a* and 248*b* connected to a common external device 250 which groups in turn can be easily extended from two as shown to any desired number of separate groups being in total count in the tens, to hundreds, to even thousands of groups as may be desired at normal operating times and extended in scope during urgent times such as during a worldwide pandemic involving a highly contagious pathogen with a high rate of mortality, or viii) any other such desired grouping or interconnected multiple groupings so implemented in view of the disclosures hereof to promote community health and wellness and to thereby mitigate transmission of contagion and assist in preventing further spread of a disease.

Thus as indicated, in some embodiments hereof, a system of patches as described herein can provide system level information that may not be available from an individual patch as deployed by a single user for personalized health and wellness, as desirable and beneficial as such may be. Thus as such, when the individual patches and/or bracelets hereof are in communication in a network with other users as described, such a system level application deployed, for example, for community testing and contact tracing as discussed below in further detail in connection with FIGS. 19A to 19D may provided substantial social benefit as well as immense health care cost savings across local, state, national, and international budgets with the further benefit of keeping economic activity well functioning at such local, state, national, and international levels so that governmental shelter-in-place orders to combat the onset of a pandemic may become a thing of the past.

Thus as described above in conjunction with FIGS. 5 to 6B in particular and generally in view of the entirety hereof, another principal embodiment of the present invention is directed to a system of diagnostic patches for controlling the spread of a disease in a community of individuals, the system comprising i) a first group of patches, each patch in the first group worn by a respective individual user associated with the first group of patches and each patch in the first group configured to communicate with other patches in the first group when in proximity with each other, ii) a second group of patches, each patch in the second group worn by a respective individual user associated with the second group of patches and each patch in the second group configured to communicate with other patches in the second group when in proximity with each other, iii) an external device configured to receive an information signal from at least one patch in the first group of patches and from at least one patch in the second group of patches, iv) a first representative patch being among the patches in the first group of patches, the first representative patch configured to communicate with the external device, and v) a second representative patch being among the patches in the second group of patches, the second representative patch configured to communicate with the external device so that at least some information from at least some of the patches in the first group is communicated to the external device by the first representative patch and at least some information from at least some of the patches in the second group is communicated to the external device by the second representative patch. In this system, the patches in the first group may be advantageously configured to communicate with the patches in the second group and the patches in the second group may be configured to communicate with the patches in the first group. Further according to this embodiment, the at least some information from at least some of the patches in the first and second groups is proximity information determined by the system when two patches from a common group are within a predetermined distance from each other. And further as may be advantageously implemented, the at least some information from at least some of the patches in the first and second groups is health information received by the system from a respective patch of a respective individual user.

With reference next to FIG. 7A, there is shown a block diagram presenting the principal steps of a mandatory use case scenario of the devices disclosed herein that may be deployed by health officials during the outbreak of a serious life-threatening pandemic to control the spread thereof in the interests of saving lives. The method of FIG. 7A, for example, could be applied as a requirement to all the schools in a city-wide school district by city or state health officials during the onset of a potential serious epidemic such as was the case in New York City during the COVID-19 pandemic of 2020. While the cost of implementing such a mandatory use case application may be considered high by some estimations, the inventors hereof believe that such a cost would be far out weighted by at least four significant benefits of this method. First, the risk of spreading such a disease would be substantially reduced for children at school and thus when they returned home from the school day, their respective household members would have a correspondingly reduced risk factor for contracting the diseased from their school-aged child. Secondly, with such a required method as presented in FIG. 7A implemented city-wide across an entire school district, teachers and school staff would similarly have a correspondingly reduced risk factor for contracting the diseased from their students. Thirdly, school children could avoid the type of interruption to their continuing education that was experienced by hundreds of thousands of students which occurred, for example, during the COVID-19 pandemic of 2020. And fourthly, all of the prior three benefits each would contribute to reducing the burden on the health care system. Thus with the above benefits as their motivation, the inventors hereof describe in further detail the mandatory use case scenario of FIG. 7A wherein at step 256 medical authorities declare an epidemic. Here in this embodiment, the epidemic declared is a flu epidemic as shown. Next at step 258, school authorities apply a fever patch to all school children entering the school, preferably before the school day starts as illustrated above in FIG. 1C. The fever patch applied may preferably be of the type discussed above in conjunction with FIG. 2A. Then during use during the school, if a student with the patch applied develops a fever, as shown at step 260, the patch detects fever in the student as described above. Then at step 262 when fever is detected in a respective student wearing such a fever patch according to the inventions hereof, the patch transmitter 136 (FIG. 2A) sends a fever signal along with the student's identification to a remote receiver such as one of the receivers 106 discussed in conjunction with FIGS. 1A and 1E. Next at step 264 of FIG. 7A, the receiver interacts with school medical server 104 (FIG. 1A) and thus alerts that a particular student has developed a fever during the school day. Next at step 266, the school's medical server is programmed in this embodiment to send a wellness signal alert or fever signal to the student's parent's cell phone or other guardian's cell phone so that the student may be promptly picked up at school and then taken to the student's family doctor's office. In an alternate embodiment of step 266, the school server may send the fever signal to the health and wellness station 102 (FIG. 1A), with prior parental approvals on record when desired, so that a medical professional may attend to the student accordingly initially at school. This alternate embodiment of step 266 requires sufficient resources maintained at the wellness station 102 throughout the school day to attend to all incoming students, such resources being perhaps at public expense, private expanse, or some sharing of public and private expense, such that parents would have sufficient comfort with reliance thereon. In yet an alternate variation of step 266 of FIG. 7A, the school medical server 102 may be programmed to send a fever signal to both the health and wellness station 102 as maintained by the school as well as the parent's or other guardian's cell phone, smart phone, tablet, or other personal wireless device by email, text, or other desired medium.

Thus as discussed above in conjunction with FIG. 7A, one preferred method of the present inventions is directed to a method of reducing the spread of disease at a school including school-age children, teachers, and authorized medical professionals, the method comprising the steps of i) declaring a flu epidemic, the declaring step performed by authorized medical authorities, ii) applying a fever patch to each student before entering the school, the applying step performed by an attending school medical professional, iii) detecting fever in a respective student, the detecting step performed by the respective student's patch, iv) sending a fever signal to a receiver with identification of the respective student, the sending a fever signal step performed by the respective student's patch, v) interacting with a school medical server, the interacting step initiated by the receiver directing the fever signal to the school medical server, and vi) sending a student pick-up message to the parent or guardian of the respective student, the sending the student pick-up message performed by the school medical server. In this method, may be advantageously maintained at the school or alternatively maintained at a location other than the school such as a central office location of a corresponding school district.

Referring now to FIG. 7B, there is shown a block diagram presenting the principal steps of another mandatory use case scenario wherein use and reporting is confined between parent and child to promote wellness in a social group such as the one here shown including school mates and teachers. Further here in this use case scenario, the patch deployed by school officials, considered to be at public expense under this scenario, is preferably of the type 148 discussed above in FIG. 3B including the surface pad 150 having preferably both the cough and sneeze pad 156 and the finger-wide pad 158, and where cost or other use variables may determine, such as type of illness to be addressed, size of school district, and time of year, the patch herein deployed may preferably include only the cough and sneeze pad 156 or alternatively only the finger-wipe pad 158 as shown and discussed above in conjunction with FIGS. 3F-1 and 3F-2. This method starts with the step 256, as above in FIG. 7A, where wherein at step 256 medical authorities declare an epidemic. Here in this embodiment, like above as with the method discussed in FIG. 7A, the epidemic declared may be a flu epidemic or may be any other serious epidemic or pandemic such as was experience worldwide in 2020 with COVID-19. Next at step 268, school authorities apply an illness-detection patch to all school children entering the school, preferably before the school day starts as illustrated above in FIG. 1C. The illness-detection patch applied may preferably be of the type discussed above in conjunction with either of FIGS. 3F-1 and 3F-2. Then during the school day, as shown at step 269, the student uses the cough or sneeze pad and/or the finger wipe pad as per the teachings hereof as the student would be so advised by school health officials and their teachers when the patch is applied and as would also be so taught in school prior thereto during routine health and wellness instruction received at school as a part of the regular school curriculum. Then, if a student with the patch applied comes in contact with a contagion, without showing symptoms, such as one that causes the flu, COVID-19, or any other severe illness under consideration at the time of deployment, as shown at step 270, the patch detects the illness in the student as described above. Then at step 272 when an illness is detected in a respective student wearing such an illness-detection patch according to the inventions hereof, the patch transmit electronics 155 (FIG. 3A) sends an illness signal along with the student's identification to a remote receiver such as one of the receivers 106 discussed in conjunction with FIGS. 1A and 1E. Next at step 264 as above with the method of FIG. 7A, the receiver interacts with school medical server 104 (FIG. 1A) and thus alerts that a particular student has developed an illness during the school day. Next at step 274, the school's medical server is programmed in this embodiment to send a wellness signal alert or illness signal to the cell phone of the parent of the student or other guardian's cell phone so that the student may be promptly picked up at school and then taken to the student's family doctor's office or when the situation warrants placed into self-quarantine at home under the parent's supervision.

Thus as discussed above in conjunction with FIG. 7B, another preferred method of the present inventions is directed to a method of reducing the spread of disease at a school including school-age children, teachers, and authorized medical professionals, the method comprising the steps of i) declaring an epidemic or pandemic, the declaring step performed by authorized medical authorities, ii) applying an illness-detection patch to each student before entering the school, the applying step performed by an attending school medical professional, iii) instructing each student how to use the illness-detection patch, the instruction step performed by an authorized educational instructor, iv) detecting an illness in a respective student, the detecting step performed by the respective student's illness-detection patch, v) sending an illness signal to a receiver with identification of the respective student, the sending an illness signal step performed by the respective student's illness-detection patch, vi) interacting with a school medical server, the interacting step initiated by the receiver directing the illness-detection signal to the school medical server, and vii) sending a student pick-up message to the parent or guardian of the respective student, the sending the student pick-up message performed by the school medical server. In one embodiment hereof, the school medical server is maintained at the school and in an alternate embodiment thereof, the school medical server is maintained at a location other than the school where such other location may preferably be at a central office location of a corresponding school district. 46. And according to one preferred embodiment of the instructional aspects of this method, the authorized educational instructor is an attending school medical professional. In this embodiment, the instruction step is performed by the attending school medical professional at the time the illness-detection patch is applied to the respective student. Alternatively, the authorized educational instructor may preferably be a school teacher. In this case, the instruction step may be performed by the school teacher during routine health and wellness instruction received at the school as a part of a regular school curriculum.

With reference next to FIG. 8A-1, there is shown a block diagram presenting the principal steps of a voluntary use case scenario of the devices disclosed herein that may be deployed by parents and their school-aged children during flu season to promote the health and wellness of individuals and community groups. Here at step 276, the school-aged child is permitted by their parent or other guardian to carry a personal mobile device during the school day. Such mobile device may be a smart phone, a table, a bio-bracelet of the type disclosed herein and in commonly-assigned related bio-bracelet patents including, for example, U.S. Pat. No. 9,113,024 titled Personal Diagnostic Devices Including Related Methods And Systems as filed on Sep. 2, 2004 which claimed priority to U.S. Provisional Application No. 60/510,769 filed on Oct. 11, 2003 and U.S. Provisional Application No. 60/500,102 filed on Sep. 3, 2003, or a smart watch of the type currently commercially available in the market place or such a smart watch that is somewhat modified by a manufacture thereof to comport well with the inventions hereof. Next at step 278, the parent or other guardian applies to their child a fever patch 126 of the type discussed above in connection with FIG. 2A. The fever patch 126 is preferably applied at home by the parent or other guardian just before leaving the house in the morning usually before the school day beings. The at step 280, the child attends school in the usual manner. The during the school day, if the child develops a temperature above a set threshold, the fever patch detects the fever in the child as illustrated at step 282. Next at step 284a, after the patch detects a fever in the child at step 282, the patch communicates with the child's mobile device, as per step 284a, and then next at step 285 as illustrated, the child's mobile device, as permitted for use at school, directly notifies the parent or other guardian that their child has developed a fever during the day at school. With such a notice receive by the parent or other guardian of the school-aged child, the parent or guardian may then go to the school directly to attend to their child as shown at step 286. Alternatively, as shown at step 287, the parent may call the school upon receiving the notification from step 285 and request the school to have their medical team attend to their child in a school run facility such as the health and wellness station 102 discussed above in FIG. 1A.

Thus with regard to FIG. 8A-1, one aspect of the present invention is directed to a method of monitoring a child's health by a parent or other guardian using a fever patch while the child attends school, the method comprising the steps of i) permitting the child to carry a personal mobile device while at school, ii) applying a fever patch to the child before the child attends school for a selected period of time, iii) having the child attend school for regular activities during the selected period of time, iv) detecting fever in the child while attending school, the detecting step performed by the child's fever patch, v) sending a fever signal to the child's personal mobile device, the sending a fever signal step performed by the child's fever patch, and vi) sending a fever message to the parent or guardian of the child, the sending the fever message performed by the child's mobile device. In one embodiment thereof, when the parent or guardian receives the fever message, the parent or guardian goes to the school to attend to the child and in an alternate embodiment of the step, when the parent or guardian receives the fever message, the parent or guardian calls the school so that the school provides medical care for the child.

FIG. 8A-2 is a block diagram presenting the principal steps of a voluntary use case scenario of the bracelet devices disclosed herein that may be deployed by parents and students to detect fever during flu season to promote the health and wellness of individuals and community groups. The steps of the method of FIG. 8A-2 follow those in the method of FIG. 8A-1 with the alternative that here in the method of this FIG. 8A-2, steps 278b, 282b, and 284b are performed by the bracelet rather than performed by a patch as above in FIG. 8A-1.

Thus alternatively according to the steps of FIG. 8A-2, another aspect of this invention is directed to a method of monitoring a child's health by a parent or other guardian using a fever-detection bracelet while the child attends school, the method comprising the steps of i) permitting the child to carry a personal mobile device while at school, ii) providing the child with a fever-detection bracelet before the child attends school for a selected period of time, iii) having the child attend school for regular activities during the selected period of time, iv) detecting fever in the child while attending school, the detecting step performed by the child's fever-detection bracelet, v) sending a fever signal to the child's personal mobile device, the sending a fever signal step performed by the child's fever-detection bracelet, and vi) sending a fever message to the parent or guardian of the child, the sending the fever message performed by the child's mobile device. In one embodiment hereof, when the parent or guardian receives the fever message from the child's mobile device, the parent or guardian goes to the school to attend to the child. Alternatively, when the parent or guardian receives the fever message from the child's mobile device, the parent or guardian calls the school so that the school may provide medical care for the child.

FIG. 8A-3 is a block diagram presenting the principal steps of a voluntary use case scenario of a bracelet device disclosed herein that may be deployed by parents and students to detect fever in the student where the bracelet communicates automatically with the parent or other guardian. Here in this method, the bracelet is provided with long-range communication functionality such that the bracelet may communicate automatically with parent or guardian's mobile phone. This communication may be via the school's WiFi system, for example, when the parent may be at the school for teacher assistance community service and when the parent or other guardian is at work or home at some extended distance from their child's school, this student-bracelet-to-parent-phone communication may be facilitated through various intermediate nodes in a communications network existing between the student's bracelet and the parent's cell phone, smart phone, tablet, or other personal wireless device as would be well understood by those skilled in the relevant arts of wireless telecommunications given their appreciation of the inventions disclosed herein. Thus with particular reference now to FIG. 8A-3, at a first step 278c, the parent provides their child with a fever bracelet 234a or 234b of the type discussed above in connection with FIGS. 4E-1 and 4E-2, respectively. Then as with the corresponding steps in the methods of FIGS. 8A-1 and 8A-2, the child attends school at step 280. Then during the school day, in the event the attending school-aged child develops a fever with a body temperature elevating above a certain predetermined threshold, the bracelet detects the fever condition at step 282c. Next at step 284c, the child's bracelet automatically notifies the parent's cell phone that their child has developed a fever while at school. This notification may be in the form of any suitable notification such as a text message or other such alert notification. Then after receiving the notification of step 284c, as with the corresponding steps discussed above in conjunction with the methods of FIGS. 8A-1 and 8A-2, the parent or guardian of the school-aged child may go to the school directly to attend to their child as shown at step 286. Alternatively, as shown at step 287, the parent or guardian may call the school upon receiving the notification from step 2884c and request the school to have the school's medical personnel attend to their child in a school run facility such as the health and wellness station 102 discussed above in FIG. 1A.

Thus with continuing regard to FIG. 8A-3, there is provided another embodiment of this invention which is more particularly directed to a method of monitoring a child's health by a parent or other guardian using a fever-detection bracelet while the child attends school, this particular method comprises the steps of i) providing the child with a fever-detection bracelet before the child attends school for a selected period of time, ii) having the child attend school for regular activities during the selected period of time, iii) detecting fever in the child while attending school, the detecting step performed by the child's fever-detection bracelet, and iv) sending a fever message to the parent or guardian of the child, the sending the fever message performed by the child's fever-detection bracelet. In this method, when the parent or guardian receives the fever message directly from the child's fever-detection bracelet, the parent or guardian may go to the school to attend to the child. Alternatively, when the parent or guardian receives the fever message from the child's fever-detection bracelet, the parent or guardian may call the school so that the school provides medical care for the child.

FIG. 8B is a block diagram presenting the principal steps of a voluntary use case scenario of the patch and bracelet devices disclosed herein having a cough pad, a sneeze pad, and/or a finger-wipe pad according to certain embodiments of the present inventions as may be deployed by parents with their school-aged children during a serious epidemic or as may otherwise be desired under parental discretion. Here at step 276, as above in the method of FIGS. 8A-1 and 8A-2, a school-aged child is permitted by their parent or other guardian to carry a personal mobile device during the school day. Such mobile device may be a smart phone, a table, a bio-bracelet of the type disclosed herein and in related commonly-assigned bio-bracelet issued patents and pending applications and including, for example, the above referenced U.S. Patent Application No. 62/972,654 filed on Feb. 11, 2020 titled Wearable Patches for Sports, or a smart watch of the type currently commercially available in the market place or such a smart watch that is somewhat modified by a manufacture thereof to comport well with the inventions hereof. Next at step 288, the parent or other guardian applies to their child an illness or disease detection patch 148 of the type discussed above in connection with FIG. 3A or alternatively an illness detection bracelet 202 discussed in conjunction with FIG. 4A. The illness detection patch 126 or illness detection bracelet 202 is preferably applied to the child at home by the parent or other guardian just before leaving the house in the morning usually before the school day beings. Then at step 280, as above in the method of FIGS. 8A-1 and 8A-2, the child attends school in the usual manner. The during the school day, if the child contracts a virus with a resulting cough or sneeze, the surface pad of the patch or bracelet as illustrated at step 290 may be use for depositing bio-material from the cough, sneeze, or finger-wipe as discussed above. In addition, when desired, the finger-wipe pad 158 may be used in an off-body patch as discussed above with regard to FIGS. 3H, 3I, and 3J. Next here in the method of FIG. 8B, at step 284a, as above in the method of FIG. 8A, after the patch detects an illness with the child at step 290, the patch communicates with the child's mobile device, as per step 284a, and then next at step 285 as illustrated, the child's mobile device, as permitted for use at school, directly notifies the parent or other guardian that their child has contracted a virus during the day at school. Alternatively, at step 284b, when the parent provides a bracelet 202 as shown in FIG. 4A, then as per step 284b, the bracelet communications with the child's mobile device, and then similarly at step 285, the child's mobile device, as permitted for use at school, directly notifies the parent or other guardian that their child has contracted a virus. And further, as shown at step 284c, when the transmit electronics 155 of a bracelet of the type shown in FIG. 4A are advantageously provided with long-range transmit capability, then as shown at step 284c, the bracelet may communicate directly with the parent's cell phone by sending an illness signal directly from the bracelet to the parent's cell phone. With such an automated notice receive by the parent or guardian of their school-aged child, by any of steps 284a, 284b or 284c, the parent or other guardian may then go to the school directly to attend to their child as shown at step 286. Or alternatively, as shown at step 287, the parent may call the school upon receiving the notification from step 285 or step 284c and request, or otherwise give permission to, school authorities to have the school's medical team attend to their child in a school run facility such as the health and wellness station 102 discussed above in FIG. 1A.

Thus with particular reference to FIG. 8B, according to a first principal embodiment hereof, the present invention is directed to a method of monitoring a child's health by a parent or other guardian using a disease-detection patch while the child attends school, the method comprising the steps of i) permitting the child to carry a personal mobile device while at school, ii) applying a disease-detection patch to the child before the child attends school for a selected period of time, iii) having the child attend school for regular activities during the selected period of time, iv) detecting an illness in the child while attending school, the detecting step performed by the child's disease-detection patch, v) sending an illness signal to the child's personal mobile device, the sending an illness signal step performed by the child's disease-detection patch, and vi) sending an illness message to the parent or guardian of the child, the sending the illness message performed by the child's mobile device. Similarly with this embodiment, when the parent or guardian receives the illness message from the child's mobile device, the parent or guardian may go directly to the school to attend to the child and as an alternative to this step, the parent or guardian may call the school so that the school provides medical care for the child.

With continuing reference to FIG. 8B, according to a second principal embodiment hereof, the present invention is further directed to a method of monitoring a child's health by a parent or other guardian using a disease-detection bracelet while the child attends school, this method comprising the steps of i) permitting the child to carry a personal mobile device while at school, ii) providing the child with a disease-detection bracelet before the child attends school for a selected period of time, iii) having the child attend school for regular activities during the selected period of time, iv) detecting an illness in the child while attending school, the detecting step performed by the child's disease-detection bracelet, v) sending an illness signal to the child's personal mobile device, the sending an illness signal step performed by the child's disease-detection bracelet, and vi) sending an illness message to the parent or guardian of the child, the sending the illness message performed by the child's mobile device. Similarly as to the above, when the parent or guardian receives the illness message from the child's mobile device, the parent or guardian may either go to the school to attend to the child or alternatively call the school so that the school provides medical care for the child.

And with still continuing reference to FIG. 8B, according to a third principal embodiment hereof, the present invention is yet further directed to a method of monitoring a child's health by a parent or other guardian using a disease-detection bracelet while the child attends school, this particular method comprising the steps of i) providing the child with a disease-detection bracelet before the child attends school for a selected period of time, ii) having the child attend school for regular activities during the selected period of time, iii) detecting an illness in the child while attending school, the detecting step performed by the child's disease-detection bracelet, and v) sending an illness message to the parent or guardian of the child, the sending the illness message performed by the child's disease-detection bracelet. And as similar to the above first and second embodiments of the methods shown and described with reference to FIG. 8B, here with this third principal embodiment thereof, when the parent or guardian receives the illness message from the child's disease-detection bracelet as show at step 284c, the parent or guardian goes to the school to attend to the child as shown at step 286 while alternatively when the parent or guardian receives the illness message from the child's disease-detection bracelet, as per step 284c, the parent or guardian calls the school so that the school provides medical care for the child as shown at step 287.

As would be readily apparent to those skilled in the relative arts, the methods discussed above in conjunctions with FIGS. 8A-1 to 8B are not limited to school-aged children and thus may be readily applied to high-school aged students and their parents as well as university students and their parents. Further, the addressed institutional setting may be readily extended from a school building or university campus to other such where children and students congregate for sport, recreation, or other forms of education such as summer camps for sports, recreation, or education as well as community youth programs and summer travel groups.

Next with reference to a certain application hereof, FIG. 8C-1 shown a block diagram presenting the principal steps of a voluntary use case scenario relating to promoting attendance for university students. Here in this embodiment, as shown at step 292, a university student applies a fever patch to their self. The fever patch deployed here may be of the type shown in FIG. 2A, fever patch 126, and may be provided to the student by the university, or provided to the student by a parent or other guardian of the student, or self-procured by the university student upon their initiative so as to promote health and wellness on their university campus. Next as shown at step 294, the patch pairs with the student's mobile phone. At step 296, the student downloads onto their mobile phone a university approved attendance and wellness app that may be uniquely provided by the university or otherwise generally available for any university to deploy with their registered students. Then at step 298, the student develops a fever with a body temperature above a pre-determined threshold, which may be set at 100 degrees Fahrenheit or 100.5 degrees Fahrenheit. Next at step 300, the fever patch reports a fever signal to the student's personal mobile phone and then promptly upon receipt thereof, at step 302, the university app as previously downloaded onto the student's phone reports to an attendance software system that the student has developed a fever. In this preferred embodiment of the present method, the attendance software system is maintained at the university registrar's office for purposes of central processing and student data security. Then at step 304, preferably under authority of the registrar's office, the university registrar or their duly designated appointee, reports an excused absence to the student's professors. And as further indicated at step 304, the excused absence notification is preferably dispatched by automated email as facilitated by the records maintained by the registrar's office. As also shown in FIG. 8C-1, this embodiment may continue with the illustrated follow-up steps to be preformed in conjunction with the university's student health center.

Next, as may be preferred by the student, the student's parents, or both the student and their parents after discussion and agreement, and as further provided by implemented infrastructure and process at the university, the method of FIG. 8C-1 may continue with additional steps relating to medical follow-up. Thus when so deployed by student acceptance and university provision, at step 306, the student enrolls in a university health support program. In this manner, when the student uses a fever patch or fever bracelet as per steps 292 to 304, the university medical services department may then efficiently be in contact with the student preferably through the registrar's office. Thus after the registrar's office receives an illness message from the student's cell phone at step 302, then in addition to reporting an excused absence to the student's professors at step 304, the registrar's office also sends a notification to student health services, as shown at step 308a, that a certain particular student has a possible illness that may require further attention. Then as a follow-up, student health services sends an appointment invitation to the student over the university network as shown at step 310a, and as is common now, the student accepts the appointment invite which is then confidently scheduled on their calendar. Then at step 312a, a medical professional from the university's student health services department conducts an interview or virtual examination of the student by video conference thus providing a telemedicine option for student's on campus. The video teleconference may be readily facilitated by any suitable software program for providing such as are currently available in the market place or where desired the university may preferably otherwise developed their own university proprietary version of same by engaging students or professors or both students and professors from their computer science department to develop an in-house telemedicine video conferencing system that is secure and proprietary to that particular university. Further the medical interview so long as suitably socially-distance, my be performed alternatively by text exchange with the student, emails exchange with the student, or by a traditional telephone call as may be preferred by the parties thereto and the costs for same.

With continuing reference to FIG. 8C-1, and as an alternative to the medical follow-up provided by student health services on campus, at step 306, the student may preferably elect to have the registrar's office contact their private doctor in their home town. Thus in this method, as shown at step 308*b*, the university registrar sends the illness notification to the student's family doctor at their home town. One additional advantage here is that the home town medical practice may have confidential records for the student from the time of their birth and thus a long-time family doctor may be better informed to advise the student than a new doctor on campus that the student has not yet been engaged with. Thus a further advantage here is that the student may be more comfortable with having a telemedicine session from their dorm room with their long-time family doctor or private doctor than with a newly assigned university doctor. Thus after the private medical practice in the home town of the student received the illness message from the registrar at step 308*b*, the private doctor's office at step 310*b* makes a telemedicine appointment with the student while the student is still residing on campus. Then at step 312*b*, a personal doctor from the student's home town interviews the student over a private telemedicine system while the student remains on campus.

Thus with particular reference to FIG. 8C-1 the present invention is further directed to a method of taking attendance at university, comprising applying a diagnostic patch to a student, pairing the applied patch to a mobile device carried by the student, downloading university wellness and attendance software on to the student mobile device, detecting a medical condition in the student with the applied patch, reporting the medical condition to the university using the wellness and attendance software on the student device, and in response to the reporting, logging an excused absence with the student's professors. In this method, the medical condition may be an elevated body temperature above a certain threshold temperature indicative of a fever.

In an extended embodiment of this method, there is also provided the step of providing follow-up health support to the student wherein the step of providing the follow-up health support to the student may comprise the further steps of having the student enroll in a follow-up health support program, sending an illness notification to student health services after the reporting of the medical condition to the university, arranging a medical appointment with the student, and conducting a medical interview with the student in a predetermined socially-distanced manner. And here, the step of conducting the medical interview with the student in a predetermined socially-distanced manner, may be performed by video conference as between dorm room and student health service, for example, or performed remotely by telephone, texting, or email.

In another embodiment illustrated in FIG. 8C-1, a fever patch or fever bracelet of the type discussed above in conjunction with FIGS. 2A and 4E, respectively, may be utilized and thus as such the present invention also provides more particularly a method of taking attendance at university where this particular method comprise applying a wearable fever-detection device to a student, pairing the applied wearable fever-detection device to a mobile device carried by the student, downloading university wellness and attendance software on to the student mobile device, detecting a fever in the student with the applied wearable fever-detection device, reporting the fever to the university using the wellness and attendance software on the student device, and in response to the reporting, logging an excused absence with the student's professors. Here, as indicated above, the wearable fever-detection device may be a fever patch 132 (FIG. 2A) configured to detect a body temperature above a certain threshold temperature inductive of the student having a fever or alternatively, the wearable fever-detection device may be a fever bracelet 234*a* or 234*b* (FIGS. 4E-1 and 4E-2, respectively) configured to detect a body temperature above a certain threshold temperature inductive of the student having a fever. And as above in the prior embodiment hereof, this method may include the further step of providing follow-up health support to the student where, in one embodiment thereof, this step of providing the follow-up health support to the student may preferably comprise the further steps of having the student enroll in a follow-up health support program, sending an illness notification to student health services after the reporting of the medical condition to the university registrar's office, arranging a medical appointment with the student, and conducting a medical interview with the student in a predetermined socially-distanced manner. And similarly, as above in the prior principal embodiment hereof, here in this method, the step of conducting the medical interview with the student in a predetermined socially-distanced manner may be performed by video conference as between the student's dorm room and university health services, for example, or otherwise performed remotely by telephone, texting, or email.

And as an alternative to the university's student health department as the provider of the follow-up medical attention, the present invention further provides that as a part of step 306 where the student enrolls in a follow-up health support program, the student may select among the university program, a private program, a public program, or any desired combination thereof. Thus with continuing reference to FIG. 8C-1, the present invention is further directed to providing follow-up health support to a student utilizing a wearable fever-detection device according to the above wherein this providing of the follow-up health support comprises the further steps of i) having the student enroll in a follow-up health support program, ii) sending an illness notification to a private doctor selected by the student after the reporting of the medical condition to the university, iii) arranging a medical appointment with the student, and iv) conducting a medical interview with the student in a predetermined socially-distanced manner. In this method wherein the student utilizes the wearable fever-detection device, the step of conducting the medical interview with the student may be performed remotely by video conference by the private doctor from the student's home town area while the student remains on campus, or the medical interview with the student may be performed remotely by telephone call with the private doctor from the student's home town area while the student remains on campus, or still as an alternative thereto this step of conducting the medical interview with the student may be performed remotely by texting with the private doctor from the student's home town area while the student remains on campus, or yet again as an alternative to any of the above, the step of conducting the medical interview with the student may be performed remotely by email initiated by the private doctor from the student's home town area while the student remains on campus.

Now with continuing reference to FIG. 8C-1, as would be apparent to those of skill in the relevant arts in view of the disclosures hereof, the above methods are not necessary limited to wearable fever-detection devices but may be readily extended to include wearable disease-detection devices such as the non-invasive disease detection patch 148 discussed above in connection with FIGS. 3A to 3K and the non-invasive disease-detection bracelet 202 discussed above in connection with FIGS. 4A to 4D. Thus as such, the present invention is yet further directed to a yet another method of taking attendance at university, where this particular embodiment comprises applying a wearable disease-detection device to a student, pairing the applied wearable disease-detection device to a mobile device carried by the student, downloading university wellness and attendance software on to the student mobile device, detecting an illness in the student with the applied wearable disease-detection device, reporting the illness to the university using the wellness and attendance software on the student device, and in response to the reporting, logging an excused absence with the student's professors. In one specific embodiment thereof, the wearable disease-detection device is a disease-detection patch including a surface pad configured to receive biological material from the student and therein, the surface pad is in fluid communication with an assay processing assembly configured to test the biological material for a pathogen inductive of the student having an illness. Alternatively, the wearable disease-detection device may be a disease-detection bracelet including a surface pad configured to receive biological material from the student. And similarly, the surface pad of the bracelet is advantageously in fluid communication with an assay processing assembly configured to test the biological material for a pathogen inductive of the student having an illness. And in either the patch or bracelet embodiment hereof, the principal alternate disease-detection method just above may similarly further include the step of providing follow-up health support to the student wherein such a step of providing the follow-up health support to the student comprises the further steps of having the student enroll in a follow-up health support program, sending an illness notification to student health services after the reporting of the medical condition to the university, arranging a medical appointment with the student, and conducting a medical interview with the student in a predetermined socially-distanced manner such as by remote video conference or by telephone, texting, or email.

Thus with continuing reference to FIG. 8C-1 where the student elects the private health care program at step 306 so that at step 308*b* the university sends the illness notification to the student's family doctor practicing at a home town location, the present invention is further directed to providing follow-up health support to a student utilizing a wearable disease-detection device according to the above wherein this providing of the follow-up health support, as with utilization of a fever-detection device, comprises the further steps of i) having the student enroll in a follow-up health support program, ii) sending an illness notification to a private doctor selected by the student after the reporting of the medical condition to the university, iii) arranging a medical appointment with the student, and iv) conducting a medical interview with the student in a predetermined socially-distanced manner. In this method wherein the student utilizes the wearable disease-detection device, the step of conducting the medical interview with the student may be performed remotely by video conference by the private doctor from the student's home town area while the student remains on campus, or the medical interview with the student may be performed remotely by telephone call with the private doctor from the student's home town area while the student remains on campus, or still as an alternative thereto this step of conducting the medical interview with the student may be performed remotely by texting with the private doctor from the student's home town area while the student remains on campus, or yet again as an alternative to any of the above wherein the student utilizes the wearable disease-detection device, the step of conducting the medical interview with the student may be performed remotely by email initiated by the private doctor from the student's home town area while the student remains on campus.

Next in FIG. 8C-2, there is shown a block diagram of the principal system elements related to performing the steps of the methods discussed above in conjunction with FIG. 8C-1. The elements of FIG. 8C-2 thus represent the principal infrastructure components to building out the university network and intranet from an IT development perspective. Thus as a roadmap thereto, the inventors hereof propose that, where and when feasibly, every university student has a fever patch or fever bracelet made available to them and that the cost thereof is covered by their parents, their university, or otherwise covered by public funding, particularly at time needed to preserve student attendance and participation on campus and to correspondingly maintain normal university semester operations during an epidemic or worldwide pandemic such as COVID-19, where hundreds of thousands of university students were required to vacate campuses and implement distance learning from home. And also where feasible, desired, and implemental or practicable, each student may have made available to them a disease-detection patch or disease-detection bracelet. Thus like the school-aged children discussed above, university student's similarly could avoid the type of impactful interruption to their continuing education that was experienced by these hundreds of thousands of university students worldwide during the COVID-19 pandemic of 2020 when such a system as disclosed herein is implemented by health officials who determine that such preservation of campus life by use of a fever-detection patch or a fever-detection bracelet or a disease-detection patch or a disease-detection bracelet would be in the common best interests of all stakeholders involved. Thus as shown in FIG. 8C-2, such an improved university infrastructure and student health services system would include as initial principal components an ample availability of any of the fever-patches, fever-bracelets, disease-patches, or disease-bracelets, or any combination thereof, as deployed across the student body as well as professors and all other employees of the university as may be desired. Thus at system nodes 314 and 316, such a supply of fever patches or bracelets is provided at node 314 and a corresponding supply of disease-detection patches or bracelets is provided at system node 316. Then as applied to the students on campus, and as would be applied analogously to professors and other employees of the university with regard to their respective employee identification cards, the system of FIG. 8C-2 pairs each respective student's ID card as shown at node 318, see FIG. 1D above for example, with each patch or bracelet as worn by that respective student which pairing is further paired with that respective student's mobile phone as shown at system node 320. Then as another principal component of this system, the university attendance and wellness app is made available to all students on campus as represented at system node 322 for downloading on to their phones as described above. Then at system node 324, the university IT department is engaged to coordinated functionality between the university registrar's student data base and the university wellness app as provided at node 322 to each student for use on their phone. Next as represented by a sample student schedule 326 for a particular semester, the present system relies on each student's acceptance of such an institutionalized program so as to promote their personal health and wellness as well as the overall health and wellness of the university community in which they are living and studying. Then for system build-out as represented in FIG. 8C-2, the university IT department is further engaged at system node 328 to provide the required functionality to the university email system such that as described above at method step 304 shown in FIG. 8C-1, the student professors may receive an email with an excused absence as shown at system node 330 and in addition thereto, such an email including a fever notification or illness notification can be further directed to student health services as shown at system node 332 and further to a private family medical practice at the student home town as shown at system node 334 so that in the alternative, the student's regular personal doctor while practicing in their home town may provide the telemedicine interview with the student rather than the student health medical profession from the university as show in method step 312b above.

Thus as described above with particular reference to FIG. 8C-2 specifically and the entirety of this disclosure generally, another principal embodiment of this present invention is directed to a system for taking attendance of university students attending classes on campus and providing follow-up medical attention when a student develops a fever, the system comprising i) a plurality of wearable fever-detection devices distributed across the students on campus, each wearable fever-detection device having a unique identification that is paired with a student when placed in service by the student, ii) attendance and wellness software provided by the university for downloading onto a personal mobile phone carried by the student, the attendance and wellness software configured to process a fever signal received by the phone from the wearable fever-detection device placed in service when the student develops an elevated body temperature above a predetermined threshold temperature, iii) a data base maintained by the university, the data base having a record of the student's classes and configured to operatively engage the attendance and wellness software as downloaded onto the student's phone, and iv) a notification system maintained by the university, the notification system operatively engaged with the data base and configured to send an excused absence message to the student's professors and a fever message to a selected health care provider when the student has the elevated body temperature. In this embodiment, the selected health care provider may be a student health provider maintained by the university or alternatively, a private health care provider located in a home town area of the student. And further herein, the wearable fever-detection device placed in service by the student may be a fever-detection patch or a fever-detection bracelet.

And as for detection of an illness, the present invention further provides a system for taking attendance of university students attending classes on campus and providing follow-up medical attention when a student develops an illness, this system comprising i) a plurality of wearable illness-detection devices distributed across the students on campus, each wearable illness-detection device having a unique identification that is paired with a student when placed in service by the student, ii) attendance and wellness software provided by the university for downloading onto a personal mobile phone carried by the student, the attendance and wellness software configured to process an illness signal received by the phone from the wearable illness-detection device placed in service when the student develops an illness thereby detected, iii) a data base maintained by the university, the data base having a record of the student's classes and configured to operatively engage the attendance and wellness software as downloaded onto the student's phone, and iv) a notification system maintained by the university, the notification system operatively engaged with the data base and configured to send an excused absence message to the student's professors and an illness message to a selected health care provider when the student has the detected illness. And in similar fashion, as with the university fever-detection system provided above, in this particular embodiment for illness detection, the selected health care provider may be a student health provider maintained by the university or a private health care provider located in a home town area of the student while the wearable disease-detection device placed in service by the student may be a disease-detection patch or a disease-detection bracelet.

Referring again to FIG. 9, now in more detail and in further view of the above, suppose that the school 100 includes a plurality of classrooms (e.g., Classrooms A-D) and a common area (e.g., school office, cafeteria, gymnasium, etc.). Also suppose that substantially all of the students in the school 100 are wearing respective patches voluntarily, by mandatory requirement, or some combination thereof.

For example, suppose that during a flu season, flu epidemic is present at or near a community associated with the school. Medical authorities can declare such a flu epidemic, such as described above at step 256 of the methods discussed in conjunction with FIGS. 7A and 7B, and in response, school authorities can apply a flu-symptom detecting patch to each child entering the school as illustrated above in FIG. 1C.

In some embodiments, a patch worn by a given child can provide an identifying information associated with that child as illustrated above in FIG. 1D. Such identifying information can be implemented by, for example, programming of the patch during application to the respective child by utilizing the RFID tag or circuit 116 associated with the patch as shown and described above in connection with FIGS. 1B and 1D.

And with continuing reference to FIG. 9, in some embodiments according to the present disclosure, the foregoing identifying information can include a student identifier and a classroom identifier. Thus, a student in Classroom A can be identified as an i-th student in classroom A. And continuing in such embodiments as further implemented, each classroom can be provided with a monitor such as the monitor 240 of FIG. 6A. Accordingly, as illustrated in FIG. 9, Classroom A is shown to include Monitor A, Classroom B is shown to include Monitor B, Classroom C is shown to include Monitor C, and Classroom D is shown to include Monitor D. A common area such as Common Area 336 may or may not be as large as a classroom. Thus, one or more monitors can be provided for such an area, such as here in FIG. 9 shown as Monitor 1 and Monitor 2 in the Common Area 336.

In the example of FIG. 9, children wearing respective patches are depicted as $\{S(1,A), S(2,A), \ldots, S(N_A,A)\}$ for students in Classroom A with $N_A$ students; $\{S(1,B), S(2,B), \ldots, S(N_B,B)\}$ for students in Classroom B with $N_B$ students;

$\{S(1,C), S(2,C), \ldots, S(N_C,C)\}$ for students in Classroom C with $N_C$ students; $\{S(1,D), S(2,D), \ldots, S(N_D,D)\}$ for students in Classroom D with No students: and so forth for any additional classrooms as may be applicable in any such school building. Since students in Classroom A are most likely to spend majority of their time in Classroom A, their condition such as for fever or other conditions indicating an illness or onset of an illness as sensed or detected by respective patches or bracelets can be monitored by Monitor A. Similarly, students of Classroom B can have their health condition sensed by respective patches or bracelets with same monitored by Monitor B and so forth for Classroom C, Classroom D, and any additional such. It will be understood that Monitor A may or may not communicate with a patch worn by a student of Classroom A, that Monitor B may or may not communicate with a patch worn by a student of Classroom B, and so forth for the additional classrooms in the school.

In the example of Common Area 336, Monitor 1, for example, can monitor a student from any classroom. Accordingly, students associated with the Common Area 336 are depicted as $\{S(1,x), S(2,x), \ldots, S(N,x)\}$ where x indicates classroom identifier, and N is the total number of students among the classrooms. For example, i-th student from Classroom D can be identified as S(i,D).

Configured in the foregoing manner, a given patch or bracelet can sense a flu symptom if such a symptom arises in the corresponding student. Information associated with such sensed flu symptom can be transmitted to one or more of the monitors.

In some of the embodiments hereof, some or all of such individual information can be forward to a school health professional, such as may be resident in the school at a station such as the health and wellness station 102 of FIG. 1A, to allow appropriate action to be taken with respect to the corresponding student. For example, a parent can be notified as discussed above in the methods of FIGS. 7A to 8B, and the student can be moved to a nurse's office or wellness station 102 for care and to reduce likelihood of further spreading of flu or other detected illness.

FIG. 9 illustrates that in some further embodiments in addition to those discussed above in FIGS. 6A and 6B, the system 246c as implemented in a school 100 can include an analyzer 338 implemented on, for example, one or more computing devices, within the school 100, outside of the school 100, or some combination thereof where such computing devices may include the school medical server 104 as discussed above in FIGS. 1A, 1C, 1D, and 1E. Such an analyzer 338 as shown here in FIG. 9 as part of the system 246c, can be configured to receive and analyze data from some or all of the monitors including Monitor A to D as well as Monitor 1 and 2, as illustrated.

For example, FIG. 10 shows a flu symptom summary 340 that can be generated by the analyzer 338 of FIG. 9, and provided to a medical and/or administrative professional. In some embodiments, such a summary 340 can be generated one or more times during school hours. For example, if a summary is generated during each period, one can see if there is an increase in the number of students exhibiting symptoms, and appropriate actions can be taken.

In the example of FIG. 10, Classroom A shows a distribution of temperatures of students measured by respective fever patches or fever bracelets. Such a distribution shows that most of the students in Classroom A have temperatures in a normal range, and relatively few have temperatures in a portion of a temperature range indicative of a flu symptom. In Classroom B, all of the students are shown to have temperatures within a normal range. In Classroom C, significant number of students 342 are shown to have temperatures in the flu symptom range. In Classroom D, only a few students in are shown to have temperatures in the flu symptom range. In the Common Area 336, significant number of students 344 are shown to have temperatures in the flu symptom range. Further analysis can be performed to determine classroom information for such students. For example, a correlation analysis can show that most of such students 344 detected in the Common Area 336 are indeed from Classroom C. Based on such a summary, a more specific action can be taken.

It is noted that while various examples are described herein in the context of flu, one or more features of the present disclosure can also be implemented to monitor other health conditions. Such health conditions can include, for example, chickenpox, infectious mononucleosis, measles, meningitis, mumps, pneumonia, polio, rheumatic fever, rubella, whooping cough, hepatitis A, fever, scarlet fever, and other such currently known or later discovered contagious, infectious, or communicable diseases.

It is also noted that one or more features of the present disclosure can allow not only detection of an illness among a group of children, but also prevention of spread of such an illness. In some embodiments, a patch having one or more features as described herein can be implemented an a relatively low cost; accordingly, large number of such patches can be utilized with a large number of children for widespread use (e.g., in a school setting). Accordingly, a cost effective way of reducing spread of communicable illnesses can be implemented.

In some embodiments, a patch having one or more features as described herein can be configured to detect one or more conditions indicative of an illness such as a flu, and/or one or more conditions likely to promote likelihood of such an illness overcoming a person's immune system. The latter can include a condition internal to the person's body (e.g., bio-molecular levels in blood detected by an assay component) and/or a condition external to the body (e.g., temperature; presence of virus in air, in droplets and/or on a surface detected by a surface detector) that can directly or indirectly affect spreading of the flu. Such one or more internal and/or external conditions can be detected in an invasive manner and/or in a non-invasive manner such as disclosed, discussed, and applied herein.

With reference next to FIG. 11A, there is shown a diagrammatic pictorial view of a two-device fever detection system 346 implemented for maintaining social distancing according to additional aspects of the present invention. The fever detection system 346 includes a first personalized wearable fever-detection device 348a as utilized by a first person and a second personalized wearable fever-detection device 348b as utilized by a second person. As illustrated, Person One carries a personal mobile device here shown as a mobile phone 350a and similarly Person Two carries their personal mobile phone 350b. In a similar manner to the fever patch 126 of FIG. 2A discussed above, the personalized wearable fever-detection devices 348a and 348b may both advantageously include the temperature sensor 132, the processor 134, the transmitter 136, and also further include a receiver 352. The transmitter 136 as herein illustrated may include a single antenna 353a for transmitting to the mobile phone 350a and for also transmitting a signal to the second person fever detection device 348b. Alternatively, the transmitter 136 may advantageously include the antenna 353a for transmitting a signal to the phone 350a and a second antenna 353b that may be dedicated to sending a device-to-device signal from the Person One fever detection device 348*a* to the second person fever detection device 348*b*. Thus in this manner, the fever-detection device 348*a* of Person One may be in two-way communication with the fever-detection device 348*b* of Person Two so that when Person Two has a detected elevated temperature indicative of a fever, the fever-detection device 348*b* of Person Two sends a message to the fever-detection device 348*a* of Person One which, in turn, sends a proximity message to the mobile phone 350*a* of Person One so that Person One may keep a safe social distance from Person Two here indicated as, for example, six feet or two meters.

Thus according to another principal aspect hereof as discussed in conjunction with FIG. 11A above, the present invention is further directed to a two-device fever detection system for maintaining social distancing, the system comprising i) a first fever detection device wearable by a first person and when deployed in use paired with a first mobile device carried by the first person, ii) a second fever detection device wearable by a second person, the second fever detection device including a second person transmitter configured to broadcast a fever signal when the second person has a detected fever, and iii) a first person receiver and transmitter implemented in the first fever detection device, the first person receiver configured to receive the fever signal from the second person transmitter and the first person transmitter configured to send a fever notification to the first mobile device so that when the second person has a detected fever and the fever detection devices are in proximity to each other, the first person may practice social distancing from the second person. In one embodiment of this system, the first person transmitter is further configured to broadcast a fever signal when the first person has a detected fever and in another the system further includes a second person receiver implemented in the second fever detection device, the second person receiver configured to receive the fever signal from the first person transmitter. And similarly therein, the second fever detection device when deployed in use is paired with a second mobile device carried by the second person and then in this embodiment, the second person transmitter may be advantageously further configured to send a fever notification to the second mobile device so that when the first person has a detected fever and the fever detection devices are in proximity to each other, the second person may practice social distancing from the first person. In any of these systems, the first fever detection device may be implemented in a fever patch configuration or alternatively in a fever-detection bracelet configuration. And similarly, the second fever detection device may be implemented in a fever patch configuration or alternatively in a fever-detection bracelet configuration.

Turning now to FIG. 11B, there is shown a diagrammatic pictorial view of another two-device fever detection system 354 implemented for maintaining social distancing and conducting contact tracing in accordance with additional principal aspects of the inventions illustrated therein. In this system 354, there is similarly provided a first personalized wearable fever-detection device 356*a* as utilized by a first person and a second personalized wearable fever-detection device 356*b* as utilized by a second person. As illustrated, Person One carries a personal mobile device here shown as the mobile phone 350*a* and similarly Person Two carries their personal mobile phone 350*b*. In a similar manner to the fever detection device 348*a* of FIG. 11A discussed above, the personalized wearable fever-detection devices 356*a* and 356*b* here in the system 354 of FIG. 11B both include the temperature sensor 132, the processor 134, the transmitter

136, the receiver 352, and in addition thereto are further provided with the RFID tag 116 and GPS functionality 358 as similarly disclosed in commonly assigned U.S. Patent Publication US 2019/0254601 titled Bio-Patch And Related Methods For Detecting Fertility Condition In Cows. And as would be understood by those skilled in the art of location and proximity devices in view of the disclosure hereof, the GPS functionality 358 may include a simple GPS interface that interacts with the full GPS unit typically provided in the mobile phones currently readily available and in common use worldwide so that such GPS components need not be redundantly duplication in the devices 356*a* and 356*b* so as to keep the cost and complexity thereof within desired design parameters. And similarly as to the devices 348*a* and 348*b* discussed above in conjunction with FIG. 11A, the transmitter 136 as herein illustrated in this system 354 may include a single antenna 353*a* for transmitting to the mobile phone 350*a* and for also transmitting a signal to the second person fever detection device 356*b*. Alternatively, the transmitter 136 may advantageously include the antenna 353*a* for transmitting a signal to the phone 350*a* and a second antenna 353*b* that may be dedicated to sending a device-to-device signal from the Person One fever detection device 356*a* to the second person fever detection device 356*b*. Thus in this manner, the fever-detection device 356*a* of Person One may be in two-way communication with the fever-detection device 356*b* of Person Two so that when Person Two has a detected elevated temperature indicative of a fever, the fever-detection device 356*b* of Person Two sends a message to the fever-detection device 356*a* of Person One which, in turn, sends a proximity message to the mobile phone 350*a* of Person One so that Person One may keep a safe social distance from Person Two here indicated as, for example, six feet or two meters. And as further provided in this system 354 at the election of Person One and/or Person Two, either or both of the mobile phones 350*a* and 350*b* may be in communication with a central reporting station 360 when one or the other of Person One or Person Two has been determined to be running a fever. In this manner, with the RFID tag 116 and GPS functionality 358, a duly appointed or elected medical professional may be in direct communication with Persons One and Two with regard to the benefits of community tracing. As illustrated, the central reporting station 360 may be a private or public facility including, for example, alternative implementations in an office building such as for all working members entering a multi-floor office building as found in major cities around the world, or a sports stadium, or implemented as a part of the HR function across all locations of a single employer, or selectively reported only to a personal doctor of either Person One or Two, and/or reported publicly to city, county, state or national health officials as shown.

Thus according to the particulars of FIG. 11B, the present invention is further directed to a two-device fever detection system for maintaining social distancing and conducting contact tracing, this system comprising i) a first fever detection device wearable by a first person and when deployed in use paired with a first mobile device carried by the first person, the first mobile device including a contact reporting functionality, ii) a second fever detection device wearable by a second person, the second fever detection device including a second person transmitter configured to broadcast a second person identification signal, iii) a first person receiver and transmitter implemented in the first fever detection device, the first person receiver configured to receive the identification signal from the second person transmitter and the first person transmitter configured to send a fever notification to the first mobile device when the first person has a detected fever, and iv) a central reporting station configured to receive a community tracing signal from the first mobile device, the community tracing signal including health information about the first person and identification information about the second person being in proximity to the first person within a pre-selected distance. In this system, the community tracing signal may be initiated by the contact reporting functionality associated with the first mobile device so that an authorized person at the central reporting station is thereby activated to communicate with the second person about being in proximity to the first person and advise about any health concerns associated therewith. Alternatively, the community tracing signal may be initiated by the first person so that an authorized person at the central reporting station is thereby activated to communicate with the second person about being in proximity to the first person and advise about any health concerns associated therewith. Similarly here in this system, the first person transmitter may be further configured to broadcast a fever signal when the first person has a detected fever and where further desired, a second person receiver may be advantageously implemented in the second fever detection device, the second person receiver configured to receive the fever signal from the first person transmitter. Thus therein, the second fever detection device when deployed in use may be paired with a second mobile device carried by the second person and where further desired, the second person transmitter may be further configured to send a fever notification to the second mobile device so that when the first person has a detected fever and the fever detection devices are in proximity to each other, the second person may practice social distancing from the first person. And similarly in this system, the first fever detection device may be implemented in a fever patch configuration or in a fever-detection bracelet configuration and also, the second fever detection device may be implemented in a fever patch configuration or in a fever-detection bracelet configuration. Regarding the contact tracing aspects hereof, as desired upon implementation, the authorized person at the central reporting station may be a i) medical professional associated with an office building, ii) a medical professional associated with a sports stadium, iii) a medical professional associated with the HR department of a private employer, iv) a personal doctor associated with the second person, v) a public health official at a city level, vi) a public health official at a county level, vi) a public health official at a state level, or vii) a public health official at a national level.

Next with reference to FIG. 12A, there is illustrated a diagrammatic pictorial view of a two-device disease detection system 362 implemented for maintaining social distancing according to additional aspects of this invention. The disease detection system 362 includes a first personalized wearable disease-detection device 364a as utilized by a first person and a second personalized wearable disease-detection device 364b as utilized by a second person. As illustrated, Person One carries a personal mobile device here shown again as the mobile phone 350a and similarly Person Two carries their personal mobile phone 350b. In a similar manner to the fever-detection device 348a of FIG. 11A, the personalized wearable disease-detection devices 364a and 364b both include the processor 134, the transmitter 136, and the receiver 352, and in addition thereto a disease detection assay assembly 366 such as any of those discussed in the commonly assigned U.S. Pat. No. 9,133,024 referenced above. And similarly as to the devices 348a and 348b discussed above in conjunction with FIG. 11A, the transmitter 136 as herein illustrated in this system 362 may include the single antenna 353a for transmitting to the mobile phone 350a and for also transmitting a signal to the second person disease detection device 364b. Alternatively, the transmitter 136 may advantageously include the antenna 353a for transmitting a signal to the phone 350a and a second antenna 353b that may be dedicated to sending a device-to-device signal from the Person One disease detection device 364a to the second person disease detection device 364b. Thus in this manner, the disease-detection device 364a of Person One may be in two-way communication with the disease-detection device 364b of Person Two so that when Person Two has a detected illness, the disease-detection device 3364b of Person Two sends a message to the disease-detection device 364a of Person One which, in turn, sends a proximity message to the mobile phone 350a of Person One so that Person One may keep a safe social distance from Person Two here indicated as, for example, six feet or two meters.

Thus according to the particulars of FIG. 12A, the present invention is yet further directed to a two-device disease detection system for maintaining social distancing, this system comprising i) a first disease detection device wearable by a first person and when deployed in use paired with a first mobile device carried by the first person, ii) a second disease detection device wearable by a second person, the second disease detection device including a second person transmitter configured to broadcast an illness signal when the second person has a detected disease, and iii) a first person receiver and transmitter implemented in the first disease detection device, the first person receiver configured to receive the illness signal from the second person transmitter and the first person transmitter configured to send an illness notification to the first mobile device so that when the second person has a detected illness and the disease detection devices are in proximity to each other, the first person may practice social distancing from the second person. In this system, the first person transmitter may be further configured to broadcast an illness signal when the first person has a detected disease and where further desired, a second person receiver may be implemented in the second disease detection device, the second person receiver configured to receive the illness signal from the first person transmitter. Here also, the second disease detection device when deployed in use may then be paired with a second mobile device carried by the second person and where further desired, the second person transmitter is further configured to send an illness notification to the second mobile device so that when the first person has a detected disease and the disease detection devices are in proximity to each other, the second person may practice social distancing from the first person. And similarly here, the first disease detection device may be implemented in a disease-detection patch configuration or in a disease-detection bracelet configuration while also the second disease detection device may be implemented in a disease-detection patch configuration or in a disease-detection bracelet configuration.

Now turning next to FIG. 12B, there is presented a diagrammatic pictorial view of another two-device disease detection system 368 here as implemented for both maintaining social distancing and conducting contact tracing in accordance with principal aspect of the inventions illustrated therein. In this system 368, there is similarly provided a first personalized wearable disease-detection device 370a as utilized by a first person and a second personalized wearable disease-detection device 370b as utilized by a second person. As illustrated, Person One carries a personal mobile device here shown as the mobile phone 350*a* and similarly Person Two carries their personal mobile phone 350*b*. In a similar manner to the disease detection device 356*a* of FIG. 11B discussed above, the personalized wearable disease-detection devices 370*a* and 370*b* here in the system 368 of FIG. 12B both include the processor 134, the transmitter 136, the receiver 352, the RFID tag 116 and the GPS interface 358 as well as the disease detection assay assembly 366 of FIG. 12A above. And similarly as to the devices 348*a* and 348*b* discussed above in conjunction with FIG. 11A, the transmitter 136 as herein illustrated in this system 368 may include a single antenna 353*a* for transmitting to the mobile phone 350*a* and for also transmitting a signal to the second person disease detection device 370*b*. Alternatively, the transmitter 136 may advantageously include the antenna 353*a* for transmitting a signal to the phone 350*a* and a second antenna 353*b* that may be dedicated to sending a device-to-device signal from the Person One disease detection device 370*a* to the Person Two disease detection device 370*b*, Thus in this manner, the disease-detection device 370*a* of Person One may be in two-way communication with the disease-detection device 370*b* of Person Two so that when Person Two has a detected illness, the disease-detection device 370*b* of Person Two sends a message to the disease-detection device 370*a* of Person One which, in turn, sends a proximity message to the mobile phone 350*a* of Person One so that Person One may keep a safe social distance from Person Two here indicated as, for example, six feet or two meters. And as further provided in this system 368 in similar manner to the system 354 above in FIG. 11B at the election of Person One and/or Person Two, either or both of the mobile phones 350*a* and 350*b* may be in communication with the central reporting station 360 when one or the other of Person One or Person Two has been determined to have a detected illness. In this manner, with the RFID tag 116 and GPS functionality 358, a duly appointed or elected medical professional may be in direct communication with Persons One and Two with regard to the benefits of community tracing. And as illustrated, similarly here in system 368 the central reporting station 360 may be a private or public facility including, for example, alternative implementations in an office building such as for all working members entering a multi-floor office building as found in major cities around the world, or a sports stadium, or implemented as a part of the HR function across all location of a single employer, or selectively reported only to a personal doctor of either Person One or Two, and/or reported publicly to city, county, state or national health officials as shown.

Thus according to the particulars of FIG. 12B, the present invention is also directed to a two-device disease detection system for maintaining social distancing and conducting contact tracing, this system comprising i) a first disease detection device wearable by a first person and when deployed in use paired with a first mobile device carried by the first person, the first mobile device including a contact reporting functionality, ii) a second disease detection device wearable by a second person, the second disease detection device including a second person transmitter configured to broadcast a second person identification signal, iii) a first person receiver and transmitter implemented in the first disease detection device, the first person receiver configured to receive the identification signal from the second person transmitter and the first person transmitter configured to send an illness notification to the first mobile device when the first person has a detected illness, and iv) a central reporting station configured to receive a community tracing signal from the first mobile device, the community tracing signal including health information about the first person and identification information about the second person being in proximity to the first person within a pre-selected distance. Also here, the community tracing signal may be initiated by the contact reporting functionality associated with the first mobile device so that an authorized person at the central reporting station is thereby activated to communicate with the second person about being in proximity to the first person and advise about any health concerns associated therewith. Alternatively, the community tracing signal may be initiated by the first person so that an authorized person at the central reporting station is thereby activated to communicate with the second person about being in proximity to the first person and advise about any health concerns associated therewith. Similarly in this system, the first person transmitter may be further configured to broadcast an illness signal when the first person has a detected illness and when desired, a second person receiver may be implemented in the second disease detection device, where the second person receiver is then configured to receive the illness signal from the first person transmitter. And for further advantage, the second disease detection device when deployed in use may be paired with a second mobile device carried by the second person. In this manner, the second person transmitter then may be further configured to send an illness notification to the second mobile device so that when the first person has a detected illness and the disease detection devices are in proximity to each other, the second person may practice social distancing from the first person. And like the system above, also here, the first disease detection device may be implemented in a disease-detection patch configuration or in a disease-detection bracelet configuration while similarly, the second disease detection device may be implemented in either a disease-detection patch configuration or in a disease-detection bracelet configuration. And also like the prior system above, regarding the contact tracing aspects hereof as desired upon implementation, the authorized person at the central reporting station according to this system may be a i) medical professional associated with an office building, ii) a medical professional associated with a sports stadium, iii) a medical professional associated with the HR department of a private employer, iv) a personal doctor associated with the second person, v) a public health official at a city level, vi) a public health official at a county level, vi) a public health official at a state level, or vii) a public health official at a national level.

As would become apparent to those artisans endeavoring in the arts related hereto in view of the disclosures hereof including the above discussed patches and bracelets as well as the various components thereof and the processes, methods, and systems disclosed therewith along with the teachings, implementations, and indications expressed herein, many, various, and sundry applications may be further advantageously placed into practice for the health and wellness benefits of individuals and the various communities in which they live, work, study, and socialize. Thus as such, the inventors hereof provide several such additional applications herein below in view of the above disclosures.

Thus now with fresh reference to FIG. 13A, there is presented a flow diagram of a method 372 of self-testing and reporting for a member of a working population using a wearable health detection device according to the present invention. In a preferred embodiment of the method 372, a start-at-home step 374 initiates the method 372 as would be typical for a member of a work force preparing to start their work day. Next at step 376, the work force member applies a wearable health detection device which may be of any of those provided above. Then at step 378, the device prefer-ably automatically reports to the employer, typically their HR department, that the device has tested the worker and the worker is cleared for reporting to their work location. If the report from the device at step 370 is a detected health condition that would indicate the worker should stay at home for medical reasons, then the worker would stay at home and seek suitable medical attention. Next at step 380 after the worker has received clearance for reporting to work, the worker attends work activities in the usual manner and the wearable health detection device continues to oper-ate in its intended manner to monitor the health and wellness of the worker. Then at step 382, the device provides infor-mation to the worker to keep social distance from co-workers and if the worker becomes ill during the work day, the device reports to company HR so that the worker may return home for attention and care or otherwise have the company provide same to any desired level of support. And in this manner, steps 382 and 384 provided sufficient infor-mation to the employer such that contact tracing with co-workers may be performed so that any such co-workers may be tested for good health and wellness.

Thus according to FIG. 13A, the present invention is further directed to a method of self-testing and reporting for a member of a working population using a wearable health detection device, the self-testing and reporting method com-prising the step of i) applying a wearable health detection device to an individual of a work group employed by an employer, ii) first reporting to the employer a health status of the employed individual allowing clearance for entering a work location, the first reporting step initiated by the wearable health detection device, iii) having the employed individual attend to work activities while the wearable health detection device continues to operate, and iv) follow-up reporting to the employer when the wearable health detection device detects a change in health status of the employed individual while attending work activates at the work location, the follow-up reporting step initiated by the wearable health detection device. Thus as such, this method may be implemented wherein the wearable health detection device is a fever patch, or a fever bracelet, or a disease-detection patch, or a disease-detection bracelet. Accordingly, when practicing any of these methods, when the wearable health detection device detects a negative change in health status of the employed individual associated therewith, the wearable health detection device initiates a stay-distant signal to co-workers in the work group so that the co-workers in the work group may thereby maintain proper social distance from the employed individual with the detected negative change in health status. Then here in this implementation, the stay-distant signal may be received by an authorized representative of the employer and then re-directed to all other members in the work group or alterna-tively the stay-distant signal may be first or only broadcast to all other members in the work group from the wearable health detection device of the employed individual with the detected negative change in health status, and then if further desired also directed to the authorized representative of the employer.

Next as per following the above, FIG. 13B is a flow diagram of a method 386 of self-testing and reporting for a member of a student population using a wearable health detection device according to the present invention. In a preferred embodiment of the method 386, a start-at-dorm step 388*a* initiates the method 386 as would be typical for a university student preparing to start their school day on campus, and as would be readily apparent to any in view hereof, since a percentage of university students live "off-campus", this method may initiate with a start-at-student-residence step 388*b*. Next at step 390, the student applies a wearable health detection device which may be of any of those provided above. Then at step 392, the device prefer-ably automatically reports to the university, typically their registrar's office, that the device has tested the student and that the student is cleared for reporting to their activities on campus such as attending classes, using the library to study, using the fitness facilities for exercise and recreation, or attending organized sport activities on campus. If the report from the device at step 392 is a detected health condition that would indicate that the student should stay sheltered in their dorm room or other residence for medical reasons, then the student would stay in their dorm room and seek suitable medical attention from the university health services, their parents, their private doctor, a public doctor, or any desired combination thereof. Next at step 394 after the student has received clearance for reporting to school activates on campus, the student attends school activities in the usual manner and the wearable health detection device continues to operate in its intended manner to monitor the health and wellness of the student. Then at step 396, the device pro-vides information to the student to keep social distance from fellow students, classmates, and professors, as provided above, and if the student becomes ill during the school day, the device reports to the registrar's office as provided above, so that the student may return to their dorm or other residence for attention and care or otherwise have the university provide same to any desired level of support. And in this manner, steps 396 and 398 provided sufficient infor-mation to the registrar such that contact tracing with fellow students, classmates, and professors may be performed so that any such students, classmates, and professors may be tested for good health and wellness.

Thus according to FIG. 13B, the present invention is further directed to a method of self-testing and reporting for a member of a student population using a wearable health detection device, this self-testing and reporting method comprising the steps of i) applying a wearable health detec-tion device to a student attending classes at a university, ii) first reporting to the university a health status of the student allowing clearance for attending group activities on campus, the first reporting step initiated by the wearable health detection device, iii) having the student attend to group activities on campus while the wearable health detection device continues to operate, and iv) follow-up reporting to the university when the wearable health detection device detects a change in health status of the student while attending group activities on campus, the follow-up report-ing step initiated by the wearable health detection device. Thus similarly as with the method discussed above in connection with FIG. 13A, this method of FIG. 13B may be implemented wherein the wearable health detection device deployed by the student is a fever patch, or a fever bracelet, or a disease-detection patch, or a disease-detection bracelet. Accordingly, when practicing any of these methods, when the wearable health detection device detects a negative change in health status of the student associated therewith, the wearable health detection device initiates a stay-distant signal to fellow students and other university members so that all university members may thereby maintain proper social distance from the student with the detected negative change in health status. Then here in this implementation, the stay-distant signal may be received by an authorized representative of the university and then re-directed to all other members in the university population or alternatively the stay-distant signal may be first or only broadcast to all other members in the university population from the wearable health detection device of the student with the detected negative change in health status, and then if further desired also directed to the authorized representative of the university.

Turning next to FIG. 14A, there is shown a perspective schematic view of a fluidic patch device 400a according to a particular embodiment hereof which includes micro needles 402 to draw a blood sample into the patch for diagnostic testing according to certain fluid-flow embodiments of the present inventions. As with the device discussed above in connection with FIG. 12B, the fluidic patch device 400a hereof in FIG. 14A may be deployed in a multi-device system herein shown for simplicity of illustration in a two-device disease detection system 404 implemented for both maintaining social distancing and conducting contact tracing in accordance with principal aspects of the inventions hereof. In this system 404, as similar to the above discussed, there is similarly provided a first personalized wearable disease-detection device 400a as utilized by a first person and a second personalized wearable disease-detection device 400b as utilized by a second person. As illustrated, Person One carries a personal mobile device here shown as the mobile phone 350a and similarly Person Two carries their personal mobile phone 350b. In a similar manner to the disease detection device 370a of FIG. 12B discussed above, the personalized wearable disease-detection devices 400a and 400b here in the system 404 of FIG. 14B both include the processor 134, the transmitter 136, the receiver 352, the RFID tag 116 and the GPS interface 358 as well as the disease detection assay assembly or bio-assay 366 of FIG. 12B above. And similarly as to the devices 370a and 370b discussed above in conjunction with FIG. 12B, the transmitter 136 as herein illustrated in this system 404 may include the single antenna 353a for transmitting to the mobile phone 350a and for also transmitting a signal to the second person disease detection device 400b. Alternatively, the transmitter 136 may advantageously include the antenna 353a for transmitting a signal to the phone 350a and a second antenna 353b that may be dedicated to sending a device-to-device signal from the Person One disease detection device 400a to the Person Two disease detection device 400b, Thus in this manner, the disease-detection device 400a of Person One may be in two-way communication with the disease-detection device 400b of Person Two so that when Person Two has a detected illness, the disease-detection device 400b of Person Two sends a message to the disease-detection device 400a of Person One which, in turn, sends a proximity message to the mobile phone 350a of Person One so that Person One may keep a safe social distance from Person Two, for example, six feet or two meters. And as further provided in this system 404 in similar manner to the system 368 above in FIG. 12B at the election of Person One and/or Person Two, either or both of the mobile phones 350a and 350b may be in communication with the central reporting station 360 when one or the other of Person One or Person Two has been determined to have a detected illness. In this manner, with the RFID tag 116 and GPS functionality 358, a duly appointed or elected medical professional may be in direct communication with Persons One and Two with regard to the benefits of community tracing. And as illustrated, similarly here in system 404 the central reporting station 360 may be a private or public facility including, for example, alternative implementations in a school population including younger school-aged children and their teachers, a university population including university students and professors, or in an office building such as for all working members entering a multi-floor office building as found in major cities around the world, or a sports stadium, or implemented as a part of the HR function across all location of a single employer, or selectively reported only to a personal doctor of either Person One or Two, and/or reported publicly to city, county, state or national health officials as shown.

FIG. 14B is a perspective cut-away pictorial view of the patch device 400 of FIG. 14A showing internal assemblies of micro-fluidic circuits, assay results detectors, and electronic signal processing components according to the teaching hereof. In particular, micro-needles 402 are each shown in fluidic proximity to a corresponding reservoir opening 403 to initially receive an initial amount of biological fluid from its corresponding micro-needle. The additional structures, elements, and functionalities thereof are provided in further detailed discussion in the above-referenced and incorporated commonly assigned U.S. Pat. No. 9,133,024 and thus as such will not be repeated here as a courtesy to our readers. And notwithstanding same, those skilled in the relevant arts may appreciate in view of the disclosures herein may be readily adapted to provide a wide variety of useful biological assays and then deployed in a multi-user system for benefit to society to provide social distancing and contract tracing during a pandemic like the COVID-19 pandemic of 2020.

FIG. 15A is a perspective schematic view of a fluidic patch device 406 according to another particular embodiment hereof which includes a flow-through needle assembly 408 to continuously provide blood sample into the patch for diagnostic testing according to certain related fluid-flow embodiments of the present inventions. As disclosed in commonly assigned U.S. Provisional Patent Application 62/700,981 filed on Jul. 20, 2018 titled Bio-Patch Having Artificial Capillaries To Provide Continuous Blood Flow, the patch 406 of FIG. 15A includes at least one artificial capillary, tubule, or lancet such that in use there is provided a continuous flow of blood through the patch as illustrated. And as with any of the above patch devices discussed above, the patch device 406 of FIG. 15A may be advantageously deployed in a multi-user system to provide social distancing and contract tracing according to the teachings and disclosures herein provided.

With reference now to FIG. 15B, there is presented a perspective cut-away pictorial view of the patch device 406 of FIG. 15A showing internal assemblies of micro-fluidic circuits, assay results detectors, and electronic signal processing components according to the teaching hereof. FIG. 15B shows an example of a patch 406 having a plurality of layers configured to provide a fluidic analysis functionality. As described herein, such an analysis functionality can be configured to analyze a sampled fluid such as blood for detecting a wide variety of diseases. In particular, flow-through needle 408 is in fluid communication with an exemplary fluidic circuit 409 to initially receive an initial amount of biological fluid from the flow-through micro-needle 408.

In the example of FIG. 15B, as provided in further detail in the above referenced and incorporated commonly assigned U.S. Pat. No. 9,133,024 and U.S. Provisional Application 62/700,981, the patch 406 can include a sample acquisition layer, a fluid processing layer, a results detection layer, and a wash buffer reservoir layer. Some or all of such layers can be configured to support a fluidic circuit that may include a sample metering chamber, a capture chamber, an analysis chamber, a waste chamber, and a wash buffer reservoir. Such chambers or reservoirs may be operatively connected to each other and may include one or more vents to prevent air blockages with the fluidic circuit. The connections and flow between chambers and reservoirs may be controlled by, for example, melt plugs, detent pressure valves, melt valves, and pinch valves in any desired combination to allow controlled movement of the samples and buffers between the different chambers and reservoirs. In an example configuration, the capture zone may be provided with several waste cambers disposed around the periphery thereof to aid in the collection of waste fluids.

A COVID-19 related application according to a specific assay embodiment hereof includes detecting an antibody to COVID-19. Antibodies start developing 1 to 3 weeks after infection, while some people are asymptomatic, it is thus important to monitor whether a person has antibody against COVID-19 even though at this time there is insufficient conclusive data to establish immunity against reinfection in all cases, but antibody testing can help determine the proportion of a population previously infected with SARS-CoV-2 and provide information about populations that may be immune and potentially protected. Also, these people can help in identifying proteins that are critical for fighting and clearing the virus, which may be useful in vaccine development. Thus in the present assay as adapted herein, the biological material is a sample of blood/serum. Antibody testing for COVID-19 is known, antibodies used in these known/approved assays can be used in an immunoassay on the patch. The two major antigenic targets of SARS-CoV-2 virus against which antibodies are detected are spike glycoprotein (S) and nucleocapsid phosphoprotein (N). While S protein is essential for virus entry and is present on the viral surface, N protein is the most abundantly expressed immunodominant protein that interacts with RNA. Multiple forms of S protein—full-length (S1+S2) or partial (S1 domain or receptor binding domain)—are used as antigens.

Referring with particularity next to FIGS. 15C and 15D, there is depicted a series of related cross-sectional side views showing the progression of a sample through the fluidic processing circuit 409 of the patch device 406 illustrated in FIGS. 15A and 15B as implemented to perform a SAR-COV-2 (COVID 19) antibody test. In this implementation of the patch 406, a blood sample 537 is withdrawn via the flow-through microprobe 408. There may be multiple collection sites, and/or multiple inlet ducts, and/or multiple reservoirs as described in further detail in commonly assigned and incorporated U.S. Pat. No. 9,133,024. Additionally, there may be several microprobes 408 that extract blood and direct the sample into micro-fluidic circuits in the patch as disclosed in commonly assigned and incorporated U.S. Provisional Application 62/891,279.

With reference now specifically to FIG. 15C, there is shown in further detail a fluidic circuit 409 for analysis of anti-Covid-19 antibody. The circuit 409 includes a melt valve 538, a sample metering chamber 540, vent ports 542 having filter material 544, and a biocompatible membrane subdivided into different sections including a cell capture or separation pad 546, a reagent pad 548, a capture and sample analysis pad 550, and an adsorbent pad 552. Reagents required for the assay are preloaded into the reagent pad 548. These reagents may include a signal agent 554 made from a micro-particle and a target molecule binding agent such as protein A that binds specifically to the Fc region of an antibody. Capture agents 556 having affinity to COVID-19 antibodies in the sample are located in the analysis pad 550. The capture agents 556 are preferably bound to the analysis pad 550 such that when the target antibody moves through the analysis pad 550 and binds to the capture agent 556, it is held in place by the capture agent for analysis. Preferred capture agents for COVID-19 include the spike glycoprotein (S) and nucleocapsid phosphoprotein (N).

Preferably about 10 to 30 µl of blood are withdrawn. The microprobes are preferably coated with anticoagulant to prevent blood clotting. When the melt plug 538 is opened, blood in the microprobe 408 enters the sample collection chamber 540 (FIG. 15C). Once the sample reaches a desired volume, chamber 540 is fluidly isolated by closing melt plug 538. After metering the sample, a second melt plug 558 is opened and the metered sample is allowed to move into the biocompatible membrane where cells are separated from the sample in pad 546. The sample then continues to move through the biocompatible membrane through the reagent pad 548 where the signal agent 554 binds to the Fc portion of the anti-Covid-19 antibodies 410 in the sample. This complex then moves into the analysis pad 402 where the anti-Covid-19 antibodies 560, having attached thereto a signal agent 554, bind to the capture agents 556 on the analysis pad 550. An incident beam of electromagnetic radiation 562 emitted by a light source or EM emitter 563 is then directed through pad 550 onto a detector 564 which measures the modified light transmitted through pad 550. The light source 563 and the detector 564 utilized in this embodiment of the patch may be preferably of the micro-wire emitter and detector type. The presence and amount of anti-Covid-19 antibodies is then analyzed by determining the difference between the intensity of the transmitted light energy before and after the sample is introduced into the analysis pad 550 and comparing the difference with a sample having a known amount of antibody. And for purposes of clarity and application, herein in connection with the various embodiments of the present emitters and detectors, the terms light energy, light radiation, EM energy, or EM radiation are used when the desired wavelength may include wavelengths outside the visible range and the term visible light is used when the EM energy is desired or preferred to be of a wavelength within the visible range.

Now continuing with the assay assemblies of FIGS. 15C and 15D as described above, the blood or cell separation is mediated via the cell separation pad 546 that will separate RBC and WBC from the plasma or serum. In a typical operation, a blood fluid sample (10-30 µl) is withdrawn from the collection tubule and from there is drawn by capillary action through the cell separation pad. As the sample migrates through the filter, the fibrous network material making up the cell separation pad retards the movement of particulate matter, including blood cells, acting to partially remove blood cells from the sample.

Because the clinically significant concentration range of specific antibodies is very small, antibody titers are commonly determined via immunoassay techniques. In an alternative embodiment to the sandwich immunoassay and related method described above, the assay may be implemented as a competitive assay between pre-loaded labeled anti-Covid-19 antibodies and the anti-Covid-19 antibodies in the sample for a limited number of binding sites on the antibody coated analysis pad 550. A variety of labels or signal agents is known and can be implemented in the present invention. Micro-particles may be used as described in commonly assigned U.S. Pat. No. 9,133,024, and fluorogenic materials useful in a fluoroimmunoassay (FIA) described in U.S. Pat. No. 3,940,475 to Gross may also be used as an alternate signal agent. Another alternative signal agent includes enzyme labels coupled to antibodies or antigens used to perform an enzyme immunoassay (EIA) as illustrated in U.S. Pat. No. 3,654,090 to Schuurs et al. As used herein, the expression labeled substance, label, marker, tracer, or the equivalent, includes any of those known labels. By way of non-limiting example, enzyme labels such as Horse radish peroxidase or alkaline phosphatase which produce a detectable signal can be used in this assay.

The biocompatible membrane is preferably formed from conjugate pads or membrane strips that are commercially available. Membrane strips with good release efficiency are preferred which facilitate the migration of labeled Covid-19 antibodies into the analysis pad. By way of non-limiting example, hydrophilic polyethersulfone membranes can be used for this purpose. The movement of serum through this layer will allow the migration of labeled Covid-19 antibodies to the analysis pad.

And as with the flow-through patch of FIGS. 15A and 15B, the inflow disease-detection patch 400 of FIGS. 14A and 14B may advantageously include the micro-fluidic circuit assembly of FIGS. 15C and 15D to perform a SAR-COV-2 (COVID 19) antibody test for each individual member within an addressed population as desired and deployed.

Thus in view of FIGS. 15A to 15D, the present invention if further directed to a wearable health detection patch for determining the presence of antibodies in a user thereof after becoming ill with an infectious disease, the patch including i) a fluidic circuit for processing a sample of blood from the user, ii) a micro-needle with an inlet and outlet allowing continuous blood flow from the user into said fluidic circuit, iii) an assay strip in fluid communication with said fluidic circuit, said assay strip including a cell capture pad, a reagent pad, and an analysis pad for capturing a specific target antibody with a capture agent, iv) a detector for detecting results obtained on said analysis pad, v) an electronic processor connected to said detector, said processor generating an electronic signal including information regarding the presence of antibodies captured on the analysis pad, and iv) a transmitter for wirelessly transmitting said electronic signal to a personal network device associated with the user. And as indicated above, this patch may be deployed across an addressed population to allow users thereof testing positive for certain antibodies to return to regular activates in the absence of a vaccine for the infectious disease associated therewith.

FIG. 16A is a perspective schematic view of a fluidic patch device 410 according to yet another particular embodiment hereof which includes an absorption pad assembly 412 to continuously provide body perspiration transfer into the patch for diagnostic testing according to certain related fluid-flow embodiments of the present inventions. This patch device 410, as with those discussed herein above, may also be advantageously deployed in a multi-user system for social distancing and contract tracing such as the systems discussed above in conjunction with any of FIGS. 6A, 6B, 9, 10, 11A, 11B, 12A, 12B, and 14A and with the methods associated therewith as may be particularly adapted to comport therewith. FIG. 16B is a perspective cut-away pictorial view of the patch device 410 of FIG. 16A showing internal assemblies of micro-fluidic circuits, assay results detectors, and electronic signal processing components according to the teaching hereof for applications of social distancing and contact tracing and as discussed in further detail as to structures and functionality thereof in the above referenced and incorporated U.S. Provisional Application 62/972,654.

Turning now to FIGS. 17A and 17B, there is shown an enlarged detail schematic representation of a single microfluidic circuit 416 which may be employed in conjunction with the personal fluidic patches of the present invention. The micro-fluidic circuit 416 shown in FIGS. 17A and 17B includes the sample collection chamber 418 which may be formed by the reservoir openings 403 and inlet formations 409 as discussed above in conjunction with FIGS. 14B and 15B. As represented in FIGS. 17A and 17B, the sample collection chamber 418 is in fluid communication with a first fluid channel 420 which in turn is fluidly connected to a fluidic chamber 422 which is in fluidic communication with a second fluid channel 424 which is next in fluid communication with a reaction zone 426. As discussed in further detail for the various assay implantations in the above referenced and incorporated, and commonly assigned U.S. Pat. No. 9,133,024, a wide variety of assays may be conducted within the reaction zone 426. The reaction zone 426 may be in fluid communication with at least one waste or collection chamber 428. To promote flow control within the fluidic circuit 416 illustrated in FIGS. 17A and 17B, the circuit may include micro-valves 430 which may be implemented in a wide variety of different configurations. Additional details regarding the valving and fluid control elements and methods utilized in the various embodiments hereof are presented and discussed in the above U.S. Pat. No. 9,133,024 in connection with specific assay implementations therein described in further detail. The particular embodiment shown in FIG. 17A includes an assay results detector 432 which may be employed to advantage as discussed and described in the above referenced, incorporated, and commonly assigned U.S. Pat. No. 9,133,024 with regard to specific embodiments therein provided and disclosed.

FIG. 17B is a view similar to FIG. 17A further illustrating an optical emitter 434 and an optical detector 436. In order to detect and image manifest results of a number of different types of assays, the assay results detector 432 of FIG. 17A may be implemented as the optical detector 436 which then may be employed in combination with the optical emitter 434 of FIG. 17B. The various optical and electrochemical phenomena that may be detected with the optical detector 438 of FIG. 17B or generally the results detector 432 of FIG. 17A are presented below in Table 1. Further detailed explanation relating thereto may be found in "Point of Care Testing", 2nd edition, edited by Christopher Price, Andrew St John, and Jocelyn Hicks, 2004.

TABLE 1

| Signal Generation | Types |
| --- | --- |
| Optical Detection | Absorbance, Reflectance, Transmission, Fluorescence, Luminescence, Turbidimetry and Nephelometry |
| Electrochemical Signals | Amperometric, Impedimetric, Potentiometric |
| Optical Motion | Light Scattering, Paramagnetic Particles, Interference Pattern, Image Analysis |
| Surface Interrogation | Optical Interference, Pattern Recognition, Surface Enhancement, Diffraction, Ellipsometry, Surface Plasmon Resonance |

The optical emitter 434 and optical detector 436 may be embodied in a variety of different optical devices or formats including for example, but not limited to, charged coupled devices (CCD), fiber optics, nano-wires, micro-wires, semiconductor light emitting and/or detecting materials, or other suitable light emitting and detecting materials or devices.

FIG. 18 is a diagrammatic representation of an example of an emitter and detector assembly 438 employing graphene electrodes 440*a* and 440*b* to emit visible or ultra-violet light onto captured bio-material 442 in a disease-detection device of the present invention and provide detection of the photonic energy after a light-matter interaction between the captured bio-material and the emitted light. As illustrated here in FIG. 18, after the light-matter interaction, wherein the light or photonic energy or electro-magnetic (EM) energy may be visible light, or otherwise in the ultra-violet range, or alternatively in the infrared range as desired for a specific embodiment thereof, the detector 440*b* directs its output to a processor for analyses of the incident energy captured thereof to provide useful information about the captured bio-material 442. For example, the emitter and detector assembly 438 may be used in conjunction with the antibody and infections disease assays described in conjunction with FIGS. 15 and 25, respectively, and more particularly according to the teachings hereof, the electromagnetic waves from the emitter 440*a* can be directed through the sample analysis pads 550 (FIGS. 15C and 15D) or 586 (FIGS. 25C and 25D) and the signal resulting beam of electromagnetic radiation, after it passes through the sample analysis pads 550 or 585, is detected by the graphene detector 440*b*; various types of signals and signal intensities can be detected by this graphene detector system including, for example, quantifying micro-particles and cells in the sample analysis pad, detecting color change and intensity, identifying and quantifying different cells and different size micro-particles, detecting and quantifying fluorescence, providing an image of the analytes in the analysis pad (like an electron microscope) and other forms of detection know to those skilled in the art.

Thus in view of FIG. 18, the present invention is further directed to a detection assembly for use in a wearable disease detection device, the detection device including i) an emitter including a graphene electrode formed from a single layer of atoms implemented to emit a selected wavelength of electromagnetic energy, ii) a detector including a graphene electrode formed from a single layer of atoms implement to detect at least a part of the energy emitted by the emitter, iii) a capture zone positioned between the emitter and the detector, the capture zone implemented to capture targeted biological material from a user indicative of a health status of a the user, and iv) a processor electronically associated with the detector to process incident energy on the detector after emitted energy interaction with any targeted biological material captured in the captured zone. And as such, this detection assembly may be advantageously implemented in any of the disease detection devices herein disclosed.

FIG. 19 is a pictorial view of various principal elements encompassing the inventions hereof as viewed from a broad system perspective which may be deployed during an epidemic or pandemic across large populations such as in schools, universities, cities, or even across entire states including cantons, provinces, or prefectures as a common term may apply, or otherwise deployed in countries nationwide in official efforts to mitigate the deleterious effects on individual and community physical health and mental wellness as well as to further mitigate the corresponding harm to the economies of states and nations as experienced by hundreds of millions of people during the worldwide COVID-19 pandemic in the years 2020 and 2021. In particular, FIG. 19 shows three illustrative personal diagnostic devices including a wearable patch 446 which is herein presented as illustrative of all the patch devices discussed in the entirety hereof, a bracelet 448 which is herein presented in this FIG. 19 as illustrative of all the bracelet devices discussed in the entirety hereof, and a wearable two-piece bio-patch and bio-bracelet system 450 including a patch element 452 and a bracelet element as disclosed in commonly assigned U.S. Provisional Application 63/057,860 as filed on Jul. 28, 2020 and titled Integrated Bio-Patch And Bio-Bracelet Systems which is hereby incorporated herein by reference. FIG. 19 also presents an illustrative number of intermediate network devices that may be implemented according to the teaching hereof to advantageously interact with the various personal diagnostic devices hereof including the above discussed fever patches and fever bracelets, the above discussed sneeze patches and sneeze bracelets, the above discussed cough patches and cough bracelets, and the above discussed finger-wipe patches and finger-wipe bracelets, as represented generally here in FIG. 19 by the patch 446, the bracelet 448, and the two-piece patch and bracelet device 450. These network devices include, but may not be limited to, a desk-top personal computer 456, a personal lap-top computer 458, a personal smart phone 460, an electronic tablet 462, and a personal digital patient diagnostic device 464. The systems of the present inventions, as illustrated here in FIG. 19, are deployed for the benefit of a user of a personal diagnostic device in a user physical environment such as the home 466. The home 466 is herein presented as illustrative of all the user physical environments discussed in the entirety hereof including schools, universities, and places of employment including office buildings, factories, warehouses, meat packing plants, poultry processing facilities, and similar places of employment as well as places of sports and entertainment such as sports stadiums and arenas, movie theaters, concert halls, bowling alleys, amusement parks, and race car venues, as well as other social or community gathering places including restaurants, places of worship, and health clubs. Thus when the systems hereof are deployed beyond individual home use, substantial benefits accruing there-from are delivered across the addressed communities and populations at large for the betterment of the common good and public health. And as further represented in FIG. 19, the user physical environment represent by the home 466 is, according to the teachings hereof, equipped with a receiver and CPU system comprising part of a smart home environment. This in this manner, any of the personal diagnostic devices herein described as represented by the patch 446, the bracelet 448, and two-piece patch and bracelet assembly 450, may be in communication with any of the intermediate devices 456, 458, 460, 462, and 464 which in turn may be in communication with the receiver and CPU system 468. Alternatively, any of the illustrative personal diagnostic devices 446, 448, and 450, may be in direct communication with the receiver and CPU system 468 as may be desired and thus implemented as a part of the user physical environment infrastructure. As further illustrated here in FIG. 19, the receiver and CPU assembly 468 may be in further communication with a central reporting authority 470 which in the case of home use may be the homeowners personal doctor's office or in the case of an epidemic or pandemic, may include school medical personal, private or public health care organizations, private or public doctor's offices, university registrar offices or university student health services departments, or public health authorities such as city, state, or national health officials including the U.S. Centers for Disease Control and other national counterparts thereof as well as international health organizations such as the World health Organization (WHO).

FIGS. 20A to 20C present skyline outlines of certain populous cities that have had experiences with prior pandemics that may better benefit from the inventions hereof when confronting future pandemics. In cities with such large populations living and working in largely vertical environments with millions of users on public transportation daily, the inventions hereof may be deployed in service of public health and wellness so that widespread harm to physical health and mental wellness may be mitigated in support of keeping leaning activities in schools and universities as well as maintaining robust economic activities desired levels by avoiding the need for extensive lockdowns, shutdowns, stay-at-home, or shelter-in-place orders, and such like imposed to various levels and effect such as during the worldwide COVID-19 worldwide pandemic of 2020 and 2021.

FIG. 21 is a perspective view of a box of packaged testing and contact tracing patches 472 including RFID tags 116 in accordance with certain aspects of the present inventions which may be deployed within populous city environments during an epidemic, pandemic, or other infectious outbreak. As with the box of patches 110 discussed above in connection with FIG. 1B for use in school deployment, the box of patches 472 includes several individual patches 474. Here however, the patches 474 may be advantageously deployed with further functionalities directed to community testing, contract tracing, and social distancing as discussed above and herein further below. And while the box of patches 110 of FIG. 1B is directed to schools with populations of a few hundred students to a few thousand students at most, the illustrative boxes of patches here discussed in connection with FIG. 21 are deployed to deliver millions of patches within cities and across nations at large.

Thus the inventors hereof and their associates are developing cost-effective methods of manufacturing these patches in volumes of hundreds of millions so like the three principal vaccines deployed during the COVID-19 pandemic of 2020 and 2021, which cost of vaccine manufacturing, distribution, and administration worldwide will be at a guesstimated expense of untold hundreds of billions of dollars, the patches hereof may be similarly deployed worldwide. And as such, it is the hope of the inventors that with early coordination with assay developers, patches hereof may be more rapidly deployed at the outset of such a pandemic so as to better mitigate the spread of such a disease so at to avoid infection in tens of millions of people across the global population at large as was the case the COVID-19 pandemic wherein at the time of filing hereof, 107,379,255 cases were detected worldwide. And further, in the case of the fever patches hereof, that require no further assay development before deployment, the inventors thereof believe that with early, rapid, and global distribution thereof into user environments that have been equipped with the systems hereof, tens of millions of cases of an infections and untold numbers of deaths may be avoided while not requiring such sever economic shut-down as were experienced during the COVID-19 pandemic.

Thus in view of the above detailed discussion, FIG. 22A is now presented as a simplified block diagram 476*a* showing the reporting of pandemic information along a chain-of-command of health officials according to certain methods of the present invention. As illustrated in the block diagram 476*a*, the method presented in this FIG. 22A includes city health officials collecting wellness data on a city population at step 478, then at step 480, the city officials report their results to county officials. Next at step 482, county officials report their collected data from all their cities to state, provincial or prefecture officials. Then state, provincial, or prefecture officials report their data to national officials as illustrated at step 484. and finally here in the method of FIG. 22A, the national officials report their data to a world wellness body such as the WHO. Thus in view of the above disclosures, the present inventions are further directed to a method of collecting and reporting health data on a city population including the steps distributing a wearable health detection device to each resident within a selected percentage of a city population, activating a central reporting system maintained by city officials, receiving a health-wellness signal at the central reporting system from at least a threshold number of the total number of wearable health detection devices distributed by the city to its residents, and processing health information received by the central reporting system from the distributed wearable health detection devices to determine the prevalence of an illness within the city population. As discussed, this method may also include the steps of reporting the city health information to county officials so that county officials may process corresponding county health information, reporting the county health information to state officials so that state officials may process corresponding state health information, reporting the state health information to national officials so that national officials may process corresponding national health information, and reporting the national health information to international officials so that international officials may process corresponding worldwide health information. And under the teachings hereof, any one of these methods may be implemented wherein the wearable health detection device is a fever detection patch, a sneeze patch, a cough patch, a finger-wipe patch, a disease-detection patch, or any desired combination thereof.

FIG. 22B presents an augmented block diagram 476*b* showing additional input reporting of pandemic information at the different levels of the chain-of-command of FIG. 22A according to certain related methods of the present invention. Thus as shown, there are three principal organized inputs to the municipal level 478. These include employers reporting to city officials on the health condition of their employees at step 488, public universities and schools reporting to city officials on the health condition of their students at step 490, and designated city managers reporting to city health officials on the health condition of all essential city workers at step 488. In the case of employers, it may be desired that only employers having a threshold number of employees above a pre-determined minimum are selected or designated to participant is such employee health reporting programs. Similarly, at the state reporting level 484, state nursing homes may implement the devices and methods hereof to report to city officials on the health condition of their nursing-home residents at step 494. And in similar fashion, at the U.S. national level 486, before reporting internationally, U.S. military health officials report on the health condition of their members at step 496 and the Veterans Administration (VA) reports on the health condition of their constituency at step 498.

Thus in view of the discussion of the augment reporting illustrated in FIG. 22B, any of the methods of FIG. 22A may be supplement with additional reporting. Thus according hereto, the present invention is further directed to a method of distributing a wearable health detection device to each employee within a selected percentage an employer's workforce, activating an employer reporting system maintained by the employer, receiving a health-wellness signal at the employer reporting system from at least a threshold number of the total number of wearable health detection devices distributed by the employer to its employees, and processing health information received by the employer reporting system from the distributed wearable health detection devices to determine the prevalence of an illness within the employer's workforce. Next when desired, appropriate, or required, the employer reports to city officials on the health condition of its employees.

Similarly, the methods of FIG. 22A under the augmented flow chart of FIG. 22B as directed to application within city schools may further include the steps of distributing a wearable health detection device to each student within a selected percentage of a school's student population, activating a school reporting system maintained by school officials, receiving a health-wellness signal at the school reporting system from at least a threshold number of the total number of wearable health detection devices distributed by the school to its students, and processing health information received by the school reporting system from the distributed wearable health detection devices to determine the prevalence of an illness within the school's student population. Here also, when desired, appropriate, or required, the school reports to city officials on the health condition of its students.

And still in similar fashion, the methods of FIG. 22A under the augmented flow chart of FIG. 22B as directed to application within a university system may further include the steps of distributing a wearable health detection device to each student within a selected percentage of a university's student population, activating a university reporting system maintained by university officials, receiving a health-wellness signal at the university reporting system from at least a threshold number of the total number of wearable health detection devices distributed by the university to its students, and processing health information received by the university reporting system from the distributed wearable health detection devices to determine the prevalence of an illness within the university's student population. And like above, when desired, appropriate, or required, the university reports to city, county, or state officials on the health condition of its students.

Yet still in similar fashion, the methods of FIG. 22A under the augmented flow chart of FIG. 22B as directed to application within a nursing home may further include the steps of distributing a wearable health detection device to each person within a selected percentage of a nursing home's residents and staff members, activating a nursing home reporting system maintained by nursing home officials, receiving a health-wellness signal at the nursing home reporting system from at least a threshold number of the total number of wearable health detection devices distributed by the nursing home to its residents and staff members, and processing health information received by the nursing home reporting system from the distributed wearable health detection devices to determine the prevalence of an illness within the nursing home's residents and staff members. And here as well, when desired, appropriate, or required, the home reports to city, county, or state officials on the health condition of its residents and staff members. And like above in regard to the methods of FIG. 22A, the methods of FIG. 22B, under the teachings hereof, this method may be implemented wherein the wearable health detection device is a fever detection patch, a sneeze patch, a cough patch, a finger-wipe patch, a disease-detection patch, or any desired combination thereof.

With reference now to FIG. 23A, there is shown a pictorial representation illustrating use of the wellness patches of the present inventions to test, contact trace, and socially isolate members of a populous community 500. As discussed above, the populous community may include all or some percentage of students at a school or within a school system, all or some percentage of students at a university or within a university system, all or some percentage of employees employed by an employer, all or some percentage of residents with a city, all or some percentage residents and staff at a nursing home or within a nursing home system, or other such designated populous groups. Here to objective is to test for a contagious illness, contract trace and infected individuals' social contacts, and then isolate for recovery individuals that have become ill. Thus as illustrated, each individual in the populous group 500 is provided with a health-detection patch 502. The representative patch 502 may include any combination of the functionalities discussed herein and thus deployed accordingly across the selected population. In this implementation, when a patch 502 detects a possible health condition in a user thereof, the user voluntarily follows up with a medical check-up and if needed then voluntarily isolates them self in an effort to mitigate the spread of the detested contagious disease. When the representative patch 502 includes proximity functionality, then contract tracing may be advantageously achieved by such a deployed system as described above and in further detail herein below. And as seen during the COVID19 pandemic of 2020 and 2021, unless some form of mitigation strategy is implemented, such as social distancing and mask wearing, an infectious disease can spread relentlessly with deviating effects on public health worldwide and corresponding harm to the vibrancy of local, state, national, and international economies. Thus, the inventions hereof are proposed for deployment so that such devastating and costly harm including the corresponding negative effects on learning and study resulting from school and university disruption, may be substantially reduced or otherwise altogether avoided by reducing or stopping the spread of infection when implemented at the outset or upon the emergence of infectious diseases subsequent hereto.

Thus next turning to FIG. 23B, there is shown a pictorial representation illustrating patch-to-patch contact tracing according to certain methods of the present invention. Here as illustrated, a participating person 504a has applied a wearable health detection patch 502a that may also include GPS functionality according to the teachings hereof. As illustrated, the participating person 504a has tested positive and has been in proximity to participating persons 504b and 504i, and by their respective patches 502b and 502i, person 504b has not yet tested positive while person 504i has tested positive with a likelihood that person 504i was infected by person 504a. In similar fashion, person 504b is subsequently in contact with persons 504c and 504d, and in turn, persons 504c and 504d are respectively in contact with participating persons 504e and 504f, and persons 504g and 504h. And by their corresponding patches 502c, 502d, 502e, 502f, 502g, and 502h, each of participating persons 504c, 504d, 504e, 504f, 504g, and 504h have returned negative tests, as shown, as of the time of testing and contacting. Thus as illustrated, all of the persons in contact with person 504b are testing negative in the illustrative example because person 504b is negative notwithstanding person 504b proximity contact to person 504a who herein as tested positive.

In a similarly manner for tracing through person 504i who is illustrated as testing positive by contact with person 504a, subsequently contacted persons 504j, 504k, 5041, and 504n have tested positive as shown for purposes of exemplary illustration. Thus with application of the present devices and methods, in the case where person 504*i* tested positive before contacting persons 504*j*, 504*k*, 504l, and 504*n*, and person 504*i* then promptly self-isolated as per accepted social standards, persons 504*j*, 504*k*, 504l, and 504*n* would not have been infected by person 504*i* and geometric propagation of this branch of the spread of this illustrated disease would have stopped with the isolation of person 504*i* promptly upon testing positive after contact with infected person 504*a*. And similarly as illustrated, in the event person 504*a* self-isolated before contacting person 504*i*, persons 504*i*, 504*j*, 504*k*, 504l, and 504*n* would not have become infected in this example as illustrated here in FIG. 23B for purposes of discussing these mitigation aspects of the present inventions.

FIG. 23B thus first presents and illustrates a method of mitigating the spread of an infectious disease within an addressed population, this method including the steps of distributing a wearable health detection device to participating persons within a selected population, self-reporting a positive test result for an infectious disease to a respective participating person as determined by their corresponding health detection device, and self-isolating by the respective participating person upon receipt of the positive test result so that the infectious disease is not further propagated by the respective participating person within the addressed population. And as with the above, this mitigation method may be implemented wherein the wearable health detection device is a fever detection patch, a sneeze patch, a cough patch, a finger-wipe patch, a disease-detection patch, or any desired combination thereof.

And when GPS functionality is included in some or all of the patches deployed in an addressed population as illustrated FIG. 23B, there is also presented therein a method of contact tracing to mitigate the spread of an infectious disease within an addressed population, this further method of mitigating and contract tracing including the steps of i) distributing a wearable health detection device to participating persons within a selected population, ii) activating a GPS functionally in each of the distributed wearable health detection devices to determine locations visited by each participating person wearing a respective health detection device, iii) reporting a positive test for a respective participating person as determined by their corresponding health detection device, and iv) reviewing location information of participating persons to determine which participating persons were in proximity to the respective participating person with a positive test result. And similarly herein, this mitigation and contact tracing method with location functionality may be implemented wherein the wearable health detection device is a fever detection patch, a sneeze patch, a cough patch, a finger-wipe patch, a disease-detection patch, or any desired combination thereof.

Now moving next to FIG. 23C, there is shown a pictorial representation similar to FIG. 23B illustrating patch-to-phone contact tracing according to certain other methods of the present invention. In this deployment according to certain communications, infrastructure, and public health systems aspects of the present inventions, each member or person 506 of an addressed population carries a personal mobile phone 508, and is further provided with a wearable health detection device such as a health-detection patch 510 of the types herein discussed above. Thus as illustrated, person 506*a* carries a personal mobile smart phone 508*a*, and wears a patch device 510*a*. Similarly person 506*b* carries a personal mobile smart phone 508*b*, and wears a patch device 510*b* an so on down to person 506*o* as shown. Thus in deployment of this system and corresponding personal and public methods, in the case where person 506*a* receives a health warning on the mobile phone 508*a*, as diagnosed by the patch 510*a*, person 506*a* may choose to promptly self-isolate to protect the health of the community. In this case scenario, since person 506*a* promptly self-isolates, no other persons from 506*b* to 506*i* and thus indirectly down the line to persons 508*c*, 508*d*, 508*j*, 508*k*, 508*e*, 508*f*, 508*g*, 508*h*, 508*l*, 508*m*, 508*n*, and 508*o* would be in contact with person 506*a*, and thus could not be infected by person 506*a* in the case where person 506*a* was diagnosed with a contagious or infections disease. In addition, in the case where all of the members of this addressed population, or alternately some percentage thereof, choose to activate a GPS tracking function on their mobile phones 508 which may be provided with or without proximity functionality, and allow health reporting to a central reporting node in the system such as reporting node 512, then as discussed above, a person's school as represented herein at infrastructure node 514 and discussed above in detail, university 516, doctor's office 518, or employer 520 may be engaged on the provide side in the interests of both personal health care as well as public health. And further, as discussed above generally and in particular with regard to FIG. 22B, in this addressed population in FIG. 23C, some or all members may elect to share their health information directly or indirectly with public health officials at the city, county, state, or federal level as represented by infrastructure node 522.

Thus as illustrated and described in detail throughout the entirety hereof and in particular in conjunction with FIG. 23C, the present invention is further directed to an infrastructure system for contact tracing and mitigating the spread of an infectious disease within an addressed population including i) a plurality of personal mobile phones distributed across the addressed population, each mobile phone uniquely associated with a specific corresponding member of the population and implemented to receive a personalized health signal from the specific corresponding member and report at least some health information concerning the health condition of the specific corresponding member, ii) a plurality of wearable health detection devices distributed across the addressed population, each of the wearable health detection devices uniquely associated with a specific corresponding member of the population and implemented to send a respective personalized health signal to the personal mobile phone of the specific corresponding member, and iii) a reporting node implemented to receive health information from each of the plurality of personal mobile phones distributed across the addressed population. As implemented, this system may be advantageously deployed further so that a percentage of the plurality of personal mobile phones distributed across the addressed population include tracking functionally over time so that proximity among members of the population may be determined in the interests of public health during the outbreak of an infectious disease.

FIG. 23D is a pictorial representation similar to FIGS. 23B and 23C presenting a combination of patch-to-patch, patch-to-bracelet, and patch-to-phone contact tracing and mitigation methods according to certain additional teachings of the present invention. Here in this addressed population patches, mobile phones, and bracelets are deployed according to certain further aspects and objective of the present inventions herein disclosed. Thus as herein illustrated, person 524*a* is carrying a personal mobile phone 526*a* and wearing a health detection bracelet 528*a*, while person 524*i* is wearing a patch 530*i* which is in proximity communication with the phone 526*b* as carried by person 524*b* in this illustrated population. In this example, person 524*i* may not be carrying a phone 526 and is not wearing a bracelet 528. As such, person 524*i*'s patch 530*i* is providing proximity communication to other persons devices in this population. And as with the population discuss in connection with FIG. 23C, person 524*c*, here in the population illustrated in FIG. 23D, is carrying a phone 526*c* and wearing a patch 530*c*. Thus in this manner, a greater sized population may be address in a more cost effective and varied manner. In practice of this multi-device deployment, including the illustrated combination of patch-to-patch, patch-to-bracelet, and patch-to-phone contact tracing and mitigation, the central reporting node 512 may be engaged by any percentage of communicating devices in the system the carrying person's school node 514, university node 516, doctor's office 518, or employer 520 interests of both personal health care as well as public health and may also report directly or indirectly to public health officials at the city, county, state, or federal level by infrastructure node 522 as discussed above.

Thus as provided in FIG. 23D, this invention is further directed to a multi-device system for contract tracing and mitigating the spread of an infectious disease within an addressed population including i) a plurality of personal mobile phones distributed across a percentage of the addressed population, each mobile phone uniquely associated with a specific corresponding member of the population and implemented to receive a personalized health signal from the specific corresponding member and report at least some health information concerning the health condition of said specific corresponding member, ii) a plurality of wearable health detection devices distributed across the addressed population, each of the wearable health detection devices uniquely associated with a specific corresponding member of the population and implemented to send a respective personalized health signal to a receiving device in the system, and iii) a reporting node implemented to receive aggregated community health information from a percentage of the plurality of personal mobile phones distributed across the addressed population. And in augment fashion to the system above, this multi-device system may be deployed wherein a percentage of the plurality of personal mobile phones and a percentage of the plurality of wearable health detection devices distributed across the addressed population each include tracking functionally over time so that proximity among members of the population may be determined in the interests of public health during the outbreak of an infectious disease.

FIG. 24 is a pictorial representation of using patches of the present for community anti-body testing. Thus to facilitate return to normal activities before the distribution of a vaccine, those members of an addressed population 532 who have contracted an infectious disease and recovered therefrom, as established by applicable medical science, may safely return to work, school, or university. As such, the various health detections hereof may be readily adapted by those of skill in the art to test for selected anti-bodies and with such at hand, then the various systems hereof deployed to report accordingly on anti-body health protection of individual members of the community for safe return to normal activities.

FIG. 25A is an exploded perspective pictorial view of the principal elements of the surface pad 150 of an embodiment of the replaceable assay cartridge 208 illustrated in FIG.

4C-1 including the surface pad 150 herein comprised of the sneeze or cough pad 156 as illustrated herein exclusive of the finger-wipe pad 158 which is herein optional for use and as such thus implemented in FIG. 25B for further and distinct discussion. Here in this embodiment of the cartridge 208, there is provided the results indicators 162, the micro-fluidic circuits 164, the assay results detectors 166, and the collection chambers 190 as discussed above. Also shown are the slots 216 in the bottom housing as utilized to secure the cartridge in a bracelet application as discussed above in connection with FIGS. 4*b* and 4D. The cartridge 208 is further herein provided with a mesh or membrane 580 which is permeable to fluids and sample material so that they easily flow into a collection pad 582 which is show as including an assay strip 584. The mesh or membrane 580 is preferably formed of a suitable material that allows for in-flow of buffer and sample material and may preferably be on the order of nanometers to micrometers in thickness.

FIG. 25B is an exploded perspective pictorial view of the principal elements of the finger-wipe pad 158 of the replaceable assay cartridge 208 illustrated in FIG. 4C-2 including the finger-wipe pad 158 implemented for on-body or off-body use as discussed above in detail in conjunction with FIGS. 3B to 4C-2. Here in this finger-wipe embodiment of the cartridge 208, there is similarly provided the results indicators 162, the micro-fluidic circuits 164, the assay results detectors 166, the collection chambers 190, and the slots 216 as well as the membrane 580, the collection pad 582, and assay strip 584. Further shown here in FIG. 25B, are the dimplets 184 as discussed above.

Next as illustrated in further detail in FIGS. 25C and 25D, impregnated or immobilized on an analysis pad 586 (nitro-cellulose or borosilicate paper matrix) are antibody capture agents 588 against, for example, Corona virus or SARS-COV-2 590. By way of non-limiting example, antibodies against Corona virus's spike glycoprotein (S) or nucleocapsid phosphoprotein (N) have proved suitable and are widely used for direct immunoassays for determining infection. Antibodies may be immobilized on a solid phase by a variety of methods known in the art, including covalent coupling, direct adsorption, physical entrapment and attachment to a protein-coated surface. For references describing this methodology, see Silman, I. H. and Katchalski, E. in Annual Review of Biochemistry, Vol. 35, p. 873 (1966); Melrose, G. J. H., in Review of Pure and Applied Chemistry, Vol. 21, p. 83, (1971); and Cuatrecasas, P. and Anfinsen, C. B., in Methods in Enzymology, Vol. 22, (1971).

As shown in FIG. 25C, once sample is collected in the sneeze or cough pad 156 or the finger-wipe dimplets 184, the user may add buffer into finger-wipe dimplets 184 or sneeze or cough pad 156 which will allow wicking movement of the sample into the collection chamber 190 then into the receiving end 591 of the assay strip 584 as shown as integrated in the collection pad 582 in this specific embodiment hereof. The sample then moves into the reagent pad 592 where sample and a signal agent 594 mix where the signal agent 594 binds to the analyte (Corona Virus) 590, if present.

Moving next to FIG. 25D, the tagged or labeled analyte 590 then moves to the capture or analysis pad 586, where the labeled analyte 590 binds to the capture agent 588. After capture, the analysis pad 586 may be washed to remove unbound signal agents and analytes. The wash process can be initiated by a time-controlled opening of a plug connecting a wash reservoir within the microfluidic circuits 164 to the analysis pad. In an enzyme assay implementation wherein the signal agent 594 is an enzyme, a chromagen substrate that reacts with the enzyme to produce a detectable reaction or signal may be mixed with the wash buffer. The wash buffer will elute unbound enzyme-labeled analytes while concomitantly allowing the bound enzyme to catalyze substrate cleavage. The wash buffer will be drained into an adsorbent pad 596. Then like above in the antibody assay analysis discussed in connection with FIGS. 15C and 15D, the incident beam of electromagnetic radiation 562 emitted from the emitter 563 is then directed through the analysis pad 586 and into the photo detector 564. The amount of light detected by the photo detector 564 is then analyzed to determine the presence of SARS-COV-2 in the sample.

The amount of enzyme-labeled analyte can be quantified by optical detection (absorbance, reflectance, transmittance or fluorescence) and from there the presence of sample analyte will be derived and results displayed in the results indication 162 (FIGS. 25A and 25B). The concentration of analyte can also be computed using a pre-established standard curve.

One of skill in the art can easily envision various applications of the replaceable assay cartridge 208 described in conjunction with these FIGS. 25A to 25D where multiple analytes can be detected and quantified, using the appropriate capture probe and signal agents, including several infectious disease agents all at once, including, for example influenza, swine flu, bird flu, Ebola, Marburg, SARS, MERS, SARS-COV-2, and such like.

Thus in view of FIGS. 25A to 25D, the present invention is further directed to a cartridge assembly for detecting the presence of an infectious disease, the cartridge assembly including i) a surface pad implemented to receive deposited biological material from a user thereof, ii) a collection pad in fluid communication with said surface pad, iii) an assay strip in fluid communication with said collection pad, said assay strip including a receiving end for receiving at least some of said deposited biological material, a reagent pad, and an analysis pad including capture agents implemented to bind to an infectious disease-causing particle after said infectious disease-causing particle has bonded to a signal agent, and iv) a detector for detecting results obtained on said analysis pad. The detector of his cartridge assembly may be advantageously implemented as the detection assembly of FIG. 18. And here in this cartridge assembly as discussed above, the surface pad may be implemented in association with a cough pad, a sneeze pad, a finger-wipe pad or any desired combination thereof.

And as understood by those skilled in the arts of animal husbandry and veterinary sciences, the inventions hereof may be readily adapted to detecting infectious diseases in animals, and in particular animals entering the food supply of humans. Thus for illustrative purposes, FIG. 26 represents such an adaptation showing a plurality of pork hogs 534 each wearing an animal health detection patch 536. As such, the above-mentioned commonly assigned patent publication relating to bovine fertility including a common inventor herewith filed as U.S. application Ser. No. 16/278,145 on Feb. 17, 2019 titled Bio-Patch And Related Methods For Detecting Fertility Condition In Cows is hereby incorporated herein by reference in its entirety. And as would be further understood by those of skill in the veterinary arts, the inventions hereof as adapted for use in live stock may be further adapted to house pets such as our beloved cats and dogs.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any one computing device described herein. In such distributed embodiments, the functions of the one computing device are distributed (e.g., over a network) such that some functions are performed on each of the distributed computing devices.

Some embodiments may be described with reference to equations, algorithms, and/or flowchart illustrations. These methods may be implemented using computer program instructions executable on one or more computers. These methods may also be implemented as computer program products either separately, or as a component of an apparatus or system. In this regard, each equation, algorithm, block, or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flow-chart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation(s), algorithm(s), and/or block(s) of the flowchart(s).

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

Unless the context clearly requires otherwise, throughout the description and the claims, the words "comprise," "com-prising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list. The word "exemplary" is used exclusively herein to mean "serving as an example, instance, or illustration." Any implementation described herein as "exemplary" is not necessarily to be construed as preferred or advantageous over other implementations.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A two-device fever detection system for maintaining social distancing, the system comprising:
   a first fever detection device wearable by a first person and when deployed in use paired with a first mobile device carried by the first person;
   a second fever detection device wearable by a second person and when deployed in use paired with a second mobile device carried by the second person, the second fever detection device including a second person transmitter configured to broadcast a fever signal when the second person has a detected fever, the second fever detection device including a sample analysis pad and a graphene detector configured to determine when the second person has a detected fever based on an analysis of a captured bio-material of the second person on the sample analysis pad, the second fever detection device implemented in a fever patch configuration or a fever-detection bracelet configuration to be wearable and removable by the second person; and
   a first person receiver and transmitter implemented in the first fever detection device, the first person receiver configured to receive the fever signal from the second person transmitter and the first person transmitter configured to send a fever notification to the first mobile device so that when the second person has a detected fever and the first and second mobile devices are in proximity to each other, the first person may practice social distancing from the second person.

2. The system according to claim 1 wherein the first person transmitter is further configured to broadcast a fever signal when the first person has a detected fever.

3. The system according to claim 2 further including a second person receiver implemented in the second fever detection device, the second person receiver configured to receive the fever signal from the first person transmitter.

4. The system according to claim 3 wherein the second person transmitter is further configured to send a fever notification to the second mobile device so that when the first person has a detected fever and the first and second mobile devices are in proximity to each other, the second person may practice social distancing from the first person.

5. The system according to claim 1 wherein the first fever detection device is implemented in a fever patch configuration.

6. The system according to claim 1 wherein the first fever detection device is implemented in a fever-detection bracelet configuration.

* * * * *